(12) United States Patent
Ismagilov et al.

(10) Patent No.: US 9,808,798 B2
(45) Date of Patent: Nov. 7, 2017

(54) FLUIDIC DEVICES FOR BIOSPECIMEN PRESERVATION

(71) Applicants: University of Chicago, Chicago, IL (US); California Institute of Technology, Pasadena, CA (US)

(72) Inventors: Rustem F. Ismagilov, Altadena, CA (US); Qichao Pan, Chicago, IL (US); Stefano Begolo, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 387 days.

(21) Appl. No.: 13/868,009

(22) Filed: Apr. 22, 2013

(65) Prior Publication Data

US 2013/0280725 A1    Oct. 24, 2013

Related U.S. Application Data

(60) Provisional application No. 61/636,426, filed on Apr. 20, 2012.

(51) Int. Cl.
*G01N 21/75* (2006.01)
*B01L 3/00* (2006.01)
(Continued)

(52) U.S. Cl.
CPC ......... *B01L 3/5027* (2013.01); *B01L 3/50273* (2013.01); *B01L 3/502738* (2013.01);
(Continued)

(58) Field of Classification Search
CPC ....... B01L 2200/027; B01L 2200/0605; B01L 2200/0673; B01L 2200/0678; B01L 2300/045; B01L 2300/0681; B01L 2300/0803; B01L 2300/0816; B01L 2300/0864; B01L 2300/0867; B01L 2300/0874; B01L 2400/0406;
(Continued)

(56) References Cited

U.S. PATENT DOCUMENTS 1,489,762 A    4/1924    Ernest et al.
1,926,276 A    9/1933    Forbes
(Continued)

FOREIGN PATENT DOCUMENTS

EP    1110084 B1    7/1999
JP    2003-533681 A    11/2003
(Continued)

OTHER PUBLICATIONS

Abrams, et al. "Development of a microfluidic device for detection of pathogens in oral samples using upconverting phosphor technology (UPT)." Annals of the New York Academy of Sciences. 2007, 1098.1: 375-388.
(Continued)

*Primary Examiner* — Dennis M White
(74) *Attorney, Agent, or Firm* — Fenwick & West LLP

(57) ABSTRACT

The present invention relates to fluidic devices for preparing, processing, storing, preserving, and/or analyzing samples. In particular, the devices and related systems and methods allow for preservation or storage of samples (e.g., biospecimen samples) by using one or more of a bridge, a membrane, and/or a desiccant.

28 Claims, 47 Drawing Sheets

(51) Int. Cl.
  *B01L 7/00* (2006.01)
  *G01N 33/543* (2006.01)

(52) U.S. Cl.
  CPC ... *B01L 3/502715* (2013.01); *B01L 3/502784* (2013.01); *B01L 7/52* (2013.01); *B01L 2200/027* (2013.01); *B01L 2200/0605* (2013.01); *B01L 2200/0673* (2013.01); *B01L 2200/0678* (2013.01); *B01L 2300/045* (2013.01); *B01L 2300/0681* (2013.01); *B01L 2300/0803* (2013.01); *B01L 2300/0816* (2013.01); *B01L 2300/0864* (2013.01); *B01L 2300/0867* (2013.01); *B01L 2300/0874* (2013.01); *B01L 2400/0406* (2013.01); *B01L 2400/0487* (2013.01); *B01L 2400/065* (2013.01); *B01L 2400/0644* (2013.01); *G01N 33/54366* (2013.01); *Y10T 436/143333* (2015.01); *Y10T 436/2525* (2015.01)

(58) Field of Classification Search
  CPC .............. B01L 3/5027; B01L 3/50273; B01L 3/502738; B01L 3/502715; B01L 2400/0487; B01L 2400/0644; B01L 2400/065; B01L 3/502784; B01L 7/52; Y10T 436/143333; Y10T 436/2525; G01N 33/54366
  See application file for complete search history.

(56) References Cited

U.S. PATENT DOCUMENTS

| | | | |
|---|---|---|---|
| 2,541,413 A | 2/1951 | Gorey | |
| 2,895,547 A | 7/1959 | Braski | |
| 4,001,527 A | 1/1977 | Hulshizer | |
| 4,021,626 A | 5/1977 | Becker | |
| 4,036,006 A | 7/1977 | Effenberger et al. | |
| 344,922 A | 7/1986 | Rebentisch | |
| 4,912,376 A | 3/1990 | Strick | |
| 5,026,113 A | 6/1991 | Dicarlo et al. | |
| 5,114,208 A | 5/1992 | Ikeda et al. | |
| 5,160,853 A | 11/1992 | Simon et al. | |
| 5,234,809 A | 8/1993 | Boom et al. | |
| 5,256,571 A | 10/1993 | Hurley et al. | |
| 5,582,988 A | 12/1996 | Backus et al. | |
| 5,590,687 A | 1/1997 | Vaughan | |
| 5,688,651 A | 11/1997 | Solomon | |
| 5,805,947 A | 9/1998 | Miyamoto et al. | |
| 5,926,660 A | 7/1999 | Salvas et al. | |
| 6,070,610 A | 6/2000 | Owler | |
| 6,120,733 A | 9/2000 | Goodman et al. | |
| 6,300,138 B1 | 10/2001 | Gleason et al. | |
| 6,325,172 B1 | 12/2001 | Langridge et al. | |
| 6,354,172 B1 | 3/2002 | Piacenza et al. | |
| 6,426,230 B1 | 7/2002 | Feistel | |
| 6,528,641 B2 | 3/2003 | Lader | |
| 6,645,717 B1 | 11/2003 | Smith et al. | |
| 6,718,742 B1 | 4/2004 | Baker | |
| 6,861,601 B2 | 3/2005 | Heien | |
| 6,914,137 B2 | 7/2005 | Baker | |
| 6,949,575 B2 | 9/2005 | Barta et al. | |
| 7,003,104 B2 | 2/2006 | Lee | |
| 7,129,091 B2 | 10/2006 | Ismagilov et al. | |
| 7,136,688 B2 | 11/2006 | Jung et al. | |
| 7,251,142 B2 | 7/2007 | Lui | |
| 7,319,004 B2 | 1/2008 | Harper et al. | |
| 7,329,485 B2 | 2/2008 | Zlotnick | |
| 7,352,655 B2 | 4/2008 | Hjelmeland | |
| 7,375,190 B2 | 5/2008 | Cheng et al. | |
| 7,579,565 B2 | 8/2009 | Dosari | |
| 7,629,165 B2 | 12/2009 | Wyatt et al. | |
| 7,655,470 B2 | 2/2010 | Ismagilov et al. | |
| 7,767,447 B2 | 8/2010 | Breidenthal et al. | |
| 7,780,336 B2 | 8/2010 | Breidenthal et al. | |
| 7,871,813 B2 | 1/2011 | Wyatt et al. | |
| 7,901,939 B2 | 3/2011 | Ismagliov et al. | |
| 8,052,929 B2 | 11/2011 | Breidenthal et al. | |
| 8,211,367 B2 | 7/2012 | Wyatt et al. | |
| 8,221,705 B2 | 7/2012 | Breidenthal et al. | |
| 8,247,176 B2 | 8/2012 | Petersen et al. | |
| 8,263,883 B2 | 9/2012 | Heien | |
| 8,273,573 B2 | 9/2012 | Ismagilov et al. | |
| 8,304,193 B2 | 11/2012 | Ismagilov et al. | |
| 8,308,346 B2 | 11/2012 | Conus et al. | |
| 8,314,517 B2 | 11/2012 | Simard et al. | |
| 8,329,407 B2 | 12/2012 | Ismagilov et al. | |
| 8,480,976 B2 | 7/2013 | Breidenthal et al. | |
| 8,491,178 B2 | 7/2013 | Breidenthal et al. | |
| 8,574,833 B2 | 11/2013 | Jenison et al. | |
| 8,615,368 B2 | 12/2013 | Light, II et al. | |
| 8,637,250 B2 | 1/2014 | Jenison | |
| 8,784,745 B2 | 7/2014 | Nelson et al. | |
| 8,883,088 B2 | 11/2014 | Malik et al. | |
| 8,968,585 B2 | 3/2015 | Malik et al. | |
| 2002/0007686 A1 | 1/2002 | Kozak et al. | |
| 2003/0008320 A1 | 1/2003 | Baker | |
| 2003/0022243 A1 | 1/2003 | Kondejewski et al. | |
| 2003/0054395 A1 | 3/2003 | Baker | |
| 2003/0130499 A1 | 7/2003 | Baker | |
| 2003/0173284 A1 | 9/2003 | Baker | |
| 2004/0119070 A1 | 6/2004 | Roach et al. | |
| 2005/0003399 A1 | 1/2005 | Blackburn et al. | |
| 2005/0009582 A1 | 1/2005 | Vooi-Kia et al. | |
| 2005/0019792 A1 | 1/2005 | Mcbride et al. | |
| 2005/0042770 A1* | 2/2005 | Derand et al. | 436/180 |
| 2005/0053941 A1 | 3/2005 | Baker et al. | |
| 2005/0087122 A1 | 4/2005 | Ismagliov et al. | |
| 2005/0123445 A1 | 6/2005 | Blecka et al. | |
| 2005/0172476 A1 | 8/2005 | Stone et al. | |
| 2005/0221339 A1 | 10/2005 | Griffiths et al. | |
| 2005/0272169 A1* | 12/2005 | Griffin et al. | 436/514 |
| 2005/0276728 A1 | 12/2005 | Muller-Cohn et al. | |
| 2006/0003439 A1 | 1/2006 | Ismagilov et al. | |
| 2006/0024712 A1 | 2/2006 | Baker et al. | |
| 2006/0078888 A1 | 4/2006 | Griffiths et al. | |
| 2006/0078893 A1 | 4/2006 | Griffiths et al. | |
| 2006/0099567 A1 | 5/2006 | Muller-cohn et al. | |
| 2006/0154247 A1 | 7/2006 | Baker et al. | |
| 2006/0163385 A1 | 7/2006 | Link et al. | |
| 2006/0263780 A1 | 11/2006 | Baker et al. | |
| 2007/0003442 A1 | 1/2007 | Link et al. | |
| 2007/0052781 A1 | 3/2007 | Fraden et al. | |
| 2007/0092914 A1 | 4/2007 | Griffiths et al. | |
| 2007/0122809 A1 | 5/2007 | Stevenson et al. | |
| 2007/0155451 A1 | 7/2007 | Lee | |
| 2007/0172954 A1 | 7/2007 | Ismagilov et al. | |
| 2007/0184489 A1 | 8/2007 | Griffiths et al. | |
| 2007/0195127 A1 | 8/2007 | Ahn et al. | |
| 2008/0003142 A1 | 1/2008 | Link et al. | |
| 2008/0003693 A1 | 1/2008 | Torres | |
| 2008/0014589 A1 | 1/2008 | Link et al. | |
| 2008/0058039 A1 | 3/2008 | Lee et al. | |
| 2008/0166793 A1 | 7/2008 | Beer et al. | |
| 2008/0176209 A1 | 7/2008 | Muller et al. | |
| 2008/0268514 A1 | 10/2008 | Muller et al. | |
| 2009/0010804 A1 | 1/2009 | Withrow, III et al. | |
| 2009/0021728 A1 | 1/2009 | Heinz et al. | |
| 2009/0060797 A1 | 3/2009 | Mathies et al. | |
| 2009/0120865 A1 | 5/2009 | Chung et al. | |
| 2009/0127206 A1 | 5/2009 | Hogberg et al. | |
| 2009/0139992 A1* | 6/2009 | Breidenthal et al. | 220/501 |
| 2009/0215050 A1 | 8/2009 | Jenison | |
| 2009/0221096 A1 | 9/2009 | Torres | |
| 2009/0281250 A1 | 11/2009 | Desimone et al. | |
| 2010/0078077 A1 | 4/2010 | Ismagilov et al. | |
| 2010/0202926 A1 | 8/2010 | Lauks et al. | |
| 2010/0233026 A1 | 9/2010 | Ismagliov et al. | |
| 2010/0304387 A1 | 12/2010 | Jenison et al. | |
| 2011/0081363 A1 | 4/2011 | Whitney et al. | |
| 2011/0112503 A1 | 5/2011 | Ismagilov et al. | |
| 2011/0142734 A1 | 6/2011 | Ismagliov et al. | |
| 2011/0165037 A1 | 7/2011 | Ismagliov et al. | |
| 2011/0176963 A1 | 7/2011 | Kim et al. | |

(56) References Cited

U.S. PATENT DOCUMENTS

| | | |
|---|---|---|
| 2011/0176966 A1 | 7/2011 | Ismagilov et al. |
| 2011/0177586 A1 | 7/2011 | Ismagilov et al. |
| 2011/0318728 A1 | 12/2011 | Phan et al. |
| 2012/0028342 A1 | 2/2012 | Ismagilov et al. |
| 2012/0052572 A1 | 3/2012 | Whitney et al. |
| 2012/0077188 A1 | 3/2012 | Nelson et al. |
| 2012/0180882 A1 | 7/2012 | Malik et al. |
| 2012/0196944 A1 | 8/2012 | Baker |
| 2012/0197009 A1 | 8/2012 | Baker |
| 2012/0264132 A1 | 10/2012 | Ismagilov et al. |
| 2012/0329038 A1 | 12/2012 | Ismagilov et al. |
| 2012/0329171 A1 | 12/2012 | Ismagliov et al. |
| 2013/0101995 A1 | 4/2013 | Rustem et al. |
| 2013/0130226 A1 | 5/2013 | Lim et al. |
| 2013/0281316 A1 | 10/2013 | Ismagilov et al. |
| 2013/0288348 A1 | 10/2013 | Breidenthal et al. |
| 2013/0309679 A1 | 11/2013 | Ismagilov et al. |
| 2013/0331298 A1 | 12/2013 | Rea |
| 2014/0017730 A1 | 1/2014 | Hicke et al. |
| 2014/0038200 A1 | 2/2014 | Jenison et al. |
| 2014/0057277 A1 | 2/2014 | Malik et al. |
| 2014/0057278 A1 | 2/2014 | Madero et al. |
| 2014/0057279 A1 | 2/2014 | Malik et al. |
| 2014/0134619 A1 | 5/2014 | Jenison |

FOREIGN PATENT DOCUMENTS

| | | |
|---|---|---|
| WO | WO 99/29703 A2 | 6/1999 |
| WO | WO 00/13014 A1 | 3/2000 |
| WO | WO 01/03149 A1 | 1/2001 |
| WO | WO 01/88185 A2 | 11/2001 |
| WO | WO 02/48164 A2 | 6/2002 |
| WO | WO 03/046177 A1 | 6/2003 |
| WO | WO 03/101494 A1 | 12/2003 |
| WO | WO 2004/038363 A2 | 5/2004 |
| WO | WO 2005/012521 A1 | 2/2005 |
| WO | WO 2006/004611 A2 | 1/2006 |
| WO | WO 2006/096571 A2 | 9/2006 |
| WO | WO 2006/101851 A2 | 9/2006 |
| WO | WO 2007/030501 A2 | 3/2007 |
| WO | WO 2007/070832 A1 | 6/2007 |
| WO | WO 2007/081385 A2 | 7/2007 |
| WO | WO 2007/081386 A2 | 7/2007 |
| WO | WO 2007/081387 A1 | 7/2007 |
| WO | WO 2007/089541 A2 | 8/2007 |
| WO | WO 2007/089777 A2 | 8/2007 |
| WO | WO 2007/133710 A2 | 11/2007 |
| WO | WO 2007/146923 A2 | 12/2007 |
| WO | WO 2008/002267 A1 | 1/2008 |
| WO | WO 2008/063227 A2 | 5/2008 |
| WO | WO 2008/069884 A2 | 6/2008 |
| WO | WO 2008/079274 A1 | 7/2008 |
| WO | WO 2009/015390 A2 | 1/2009 |
| WO | WO 2009/048673 A2 | 4/2009 |
| WO | WO 2009/070640 A2 | 6/2009 |
| WO | WO 2009/070742 A2 | 6/2009 |
| WO | WO 2009/105648 A2 | 8/2009 |
| WO | WO 2009/149257 A1 | 12/2009 |
| WO | WO 2010/078420 A2 | 7/2010 |
| WO | WO 2010/111265 A1 | 9/2010 |
| WO | WO 2011/109762 A1 | 9/2011 |
| WO | WO 2013/123238 A1 | 8/2013 |

OTHER PUBLICATIONS

Bellisario, et al. Simultaneous measurement of thyroxin and thyrotropin from newborn dried blood-spot specimens using a multiplexed fluorescent microsphere immunoassay. Clin Chem. 2000, 46:1422-1424.

Boom, et al. "Rapid and simple method for purification of nucleic acids." Journal of clinical microbiology. 1990, 28.3: 495-503.

Britten, Frederick James. The watch & clock makers' handbook, dictionary and guide. Spon, 1896.

Cady, et al. "A microchip-based DNA purification and real-time PCR biosensor for bacterial detection." Sensors, Proceedings of IEEE. Oct. 24-27, 2004, 3:1191-1194. DOI: 10.1109/ICSENS.2004.1426391.

Cassol, et al. "Use of dried blood spot specimens in the detection of human immunodeficiency virus type 1 by the polymerase chain reaction." Journal of clinical microbiology. 1991, 29.4: 667-671.

Chu, et al. "A nanoporous silicon membrane electrode assembly for on-chip micro fuel cell applications." Microelectromechanical Systems Journal. 2006, 15.3: 671-677.

Cohen, et al. "Microfabrication of silicon-based nanoporous particulates for medical applications." Biomedical Microdevices, 2003. 5.3: 253-259.

De Jesus, et al. Development and evaluation of quality control dried blood spot materials in newborn screening for lysosomal storage disorders. Clin Chem. 2009. 55:158-164.

De Jong, et al. "New replication technique for the fabrication of thin polymeric microfluidic devices with tunable porosity." Lab on a Chip. 2005, 5.11: 1240-1247.

Desai, et al. "Nanoporous anti-fouling silicon membranes for biosensor applications." Biosensors & Bioelectronics, 2000, 15: 453-462.

Du, et al. "High-throughput nanoliter sample introduction microfluidic chip-based flow injection analysis system with gravity-driven flows." *Analytical chemistry*. 2005, 77.5: 1330-1337.

Fukaya, et al. "Evaluation of a series of imidazolium based ionic liquids as solvents for nucleic acids". AE1—Fourteenth International Symposium on Molten Salts Joint International Meeting, Oct. 3-Oct. 8, 2004. Abstract 2437.

Glasgow, David. Watch and clock making. Cassell, 1893.

Great Basin Corporation. Isothermal Amplification. Available at www.gbscience.com/technology/iso-amp. Accessed Jan. 6, 2014.

Great Basin Corporation. Sample-to-Result Molecular Diagnostics. Available at www.gbscience.com. Accessed Jan. 6, 2014.

Great Basin Corporation. Technology—Early appropriate treatment of infections is critical for good patient outcomes and to manage treatment costs. Available at www.gbscience.com/technology. Access Jan. 6, 2014.

Gulliksen, et al. "Parallel nanoliter detection of cancer markers using polymer microchips." Lab on a Chip. 2005, 5.4: 416-420.

Hong, et al. "A nanoliter-scale nucleic acid processor with parallel architecture." Nature biotechnology. 2004, 22.4: 435-439.

Huang, et al. "Counting low-copy number proteins in a single cell." Science. 2007, 315.5808: 81-84.

International search report and written opinion dated Jul. 25, 2013 for PCT/US2013/037658.

Kaigala, et al. "Automated screening using microfluidic chip-based PCR and product detection to assess risk of BK virus-associated nephropathy in renal transplant recipients." Electrophoresis. 2006, 27.19: 3753-3763.

Koh, et al. "Integrating polymerase chain reaction, valving, and electrophoresis in a plastic device for bacterial detection." Analytical Chemistry. 2013, 75.17: 4591-4598.

Lapizco-Encinas, et al. "An insulator-based (electrodeless) dielectrophoretic concentrator for microbes in water." Journal of microbiological methods. 2005, 62.3: 317-326.

Leamon, et al. "Overview: methods and applications for droplet compartmentalization of biology." Nature methods. 2006, 3.7: 541-543.

Li, et al. "Dried blood spot sampling in combination with LC-MS/MS for quantitative analysis of small molecules." Biomedical Chromatography. 2010. 24.1: 49-65.

Liu, et al. "A nanoliter rotary device for polymerase chain reaction." Electrophoresis 2002, 23 (2002): 1531-1536.

Macek, et al. "Papers, ready-for-use plates, and flexible sheets for chromotography." Chromatographic Reviews. 1971, vol. 15, No. 1, pp. 1-28 DOI: 10.1016/0009-5907(71)80007-8.

Madou, et al. Compact Disc Microfluidics. UC Irvine. Mmadou.eng.uci.edu/research_cd.html.

Martinez, et al. "FLASH: a rapid method for prototyping paper-based microfluidic devices." Lab on a Chip. 2008, 8.12: 2146-2150.

(56) References Cited

OTHER PUBLICATIONS

Martinez, et al. "Patterned paper as a platform for inexpensive, low-volume, portable bioassays." Angewandte Chemie International Edition. 2007, 46.8: 1318-1320.
Martinez, et al. "Simple telemedicine for developing regions: camera phones and paper-based microfluidic devices for real-time, off-site diagnosis." Analytical Chemistry. 2008, 80.10: 3699-3707.
Matsubara, et al. "Microchamber array based DNA quantification and specific sequence detection from a single copy via PCR in nanoliter volumes." Biosensors and Bioelectronics. 2005, 20.8: 1482-1490.
McDade, et al. "What a drop can do: dried blood spots as a minimally invasive method for integrating biomarkers into population-based research." Demography. 2007. 44.4: 899-925.
Merline, et al. "Microfluidic-assisted growth of colloidal crystals." Soft Matter. 2012, 8.13: 3526-3537.
Milham, Willis I. Time and Timekeepers. New York: MacMillan, 1945.
Ohji, et al. "Macroporous silicon formation for micromachining." Micromachining and Microfabrication. International Society for Optics and Photonics, 1997. 189-197.
Ottesen, et al. "Microfluidic digital PCR enables multigene analysis of individual environmental bacteria." Science. 200, 314.5804: 1464-1467.
Parker, et al. The use of the dried blood spot sample in epidemiological studies. J Clin Pathol. 1999. 52:633-639.
Petronis, et al. "Model porous surfaces for systematic studies of material-cell interactions." Journal of Biomedical Materials. 2003, Research Part A 66.3: 707-721.
Pichonat, et al. "Development of porous silicon-based miniature fuel cells." Micromech. Microeng. 2005, 15.9: S179-S184 doi:10.1088/0960-1317/15/9/S02.
Randall, et al. Permeation-driven flow in poly(dimethylsiloxane) microfluidic devices. Proc. Natl. Acad. Sci. 2005, 102:10813-10818.
Rea, et al. Point-of-Care Molecular Diagnostic Testing. Created Dec. 12, 2012 20:17. Published: Dec. 12, 2012. Published on IVD Technology. Available at http://www.ivdtechnology.com/print/3097. Accessed Jan. 6, 2014.
Segur, et al. "Viscosity of glycerol and its aqueous solutions." Industrial & Engineering Chemistry. 1951, 43.9: 2117-2120.
Shi, et al. "Ionic liquids promote PCR amplification of DNA." Chemical Communications . 2012, 48.43: 5325-5327.
Sia, et al. An integrated approach to a portable and low-cost immunoassay for resource-poor settings. Angew Chem Int Ed Engl. 2004, 43:498-502.
Vozzi, et al. "Fabrication of PLGA scaffolds using soft lithography and microsyringe deposition." Biomaterials. 2003, 24: 2533-2540.
Wang, et al. "Direct extraction of double-stranded DNA into ionic liquid 1-butyl-3-methylimidazolium hexafluorophosphate and its quantification." Analytical chemistry 79.2 (2007): 620-625.
Wang, et al. "Palladium—silver thin film for hydrogen sensing." Sensors and Actuators B: Chemical. 2007, 123.1: 101-106.
Williams, et al. "The use of dried blood spot sampling in the National Social Life, Health, and Aging Project." The Journals of Gerontology Series B: Psychological Sciences and Social Sciences. 2009. 64.suppl 1: i131-i136.
Wong, et al. "Electrokinetic bioprocessor for concentrating cells and molecules." Analytical chemistry. 2004, 76.23: 6908-6914.
Yang, et al. "High sensitivity PCR assay in plastic micro reactors." Lab on a Chip. 2002, 2.4: 179-187.
International search report and written opinion dated Aug. 14, 2013 for PCT Application No. US2013/037660.
Office action dated Apr. 6, 2015 for U.S. Appl. No. 13/868,028.
Begolo, S. et al., "A Microfluidic Device for Dry Sample Preservation in Remote Settings," Lab Chip, Nov. 21, 2013, pp. 4331-4342, vol. 13, No. 22.
Begolo, S. et al., "Supplementary Material for a Microfluidic Device for Dry Sample Preservation in Remote Settings from A Microfluidic Device for Dry Sample Preservation in Remote Settings," The Royal Society of Chemistry, Sep. 17, 2013, 18 pages, [Online] [Retrieved on Sep. 7, 2015] Retrieved from the Internet<URL:http://www.rsc.org/suppdata/lc/c3/c31c50747e/c31c50747e.pdf>.
Du, W. et al., "SlipChip," Lab Chip, Jan. 2009, pp. 2286-2292, vol. 9, No. 16.
European Extended Search Report, European Application No. 13777661.3, dated Sep. 21, 2015, 7 pages.
Li, L. et al., "Dead-End Filling of SlipChip Evaluated Theoretically and Experimentally as a Function of the Surface Chemistry and the Gap Size Between the Plates for Lubricated and Dry SlipChips," Langmuir, Jul. 20, 2010, pp. 12456-12471, vol. 26, No. 14.
Shen, F. et al., "Nanoliter Multiplex PCR Arrays on a SlipChip," Analytical Chemistry, Jun. 2010, pp. 4606-4612, vol. 82, No. 11.
Japanese Patent Office, Office Action for Japanese Application No. 2015-507251, dated Jan. 25, 2017, 8 Pages (with English translation).

\* cited by examiner

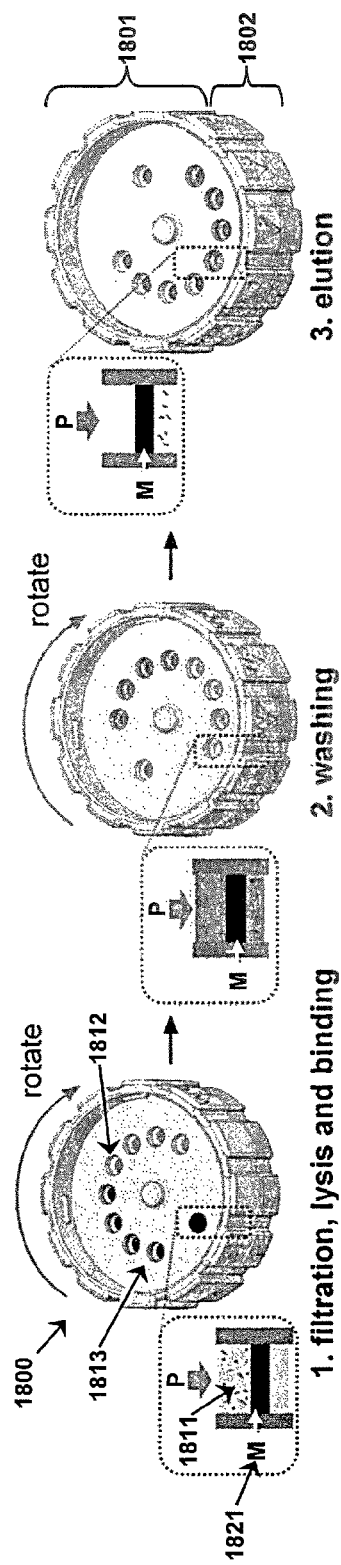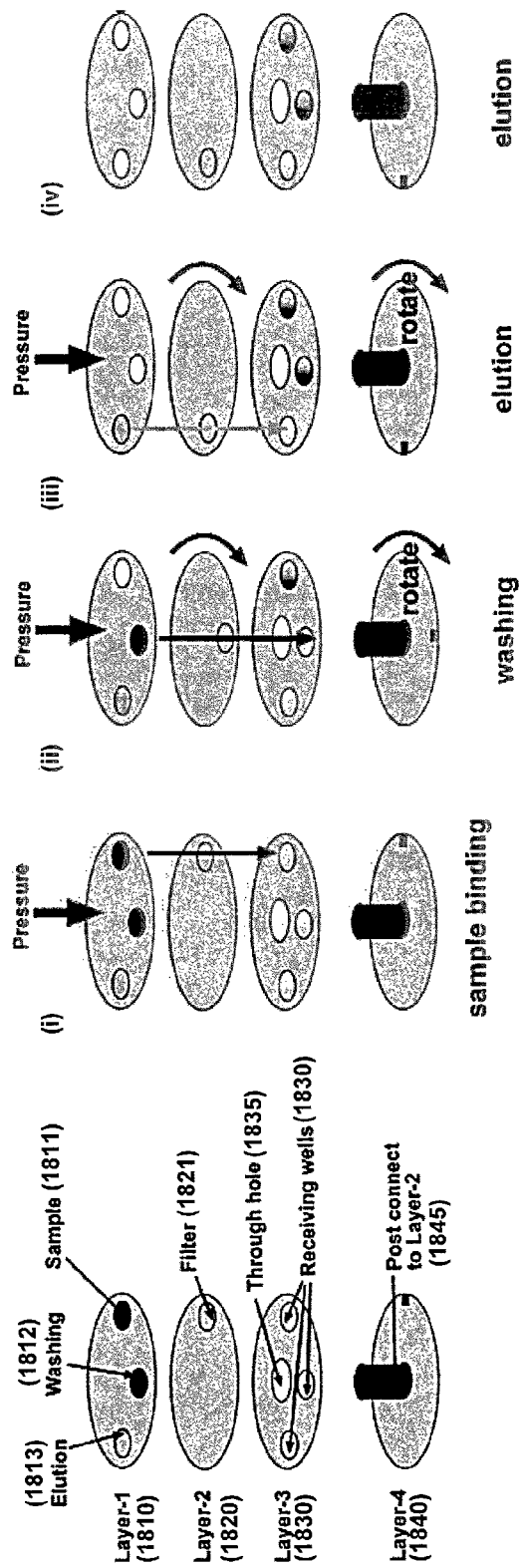
Figure 18A
Figure 18B

1. Drop in sample
2. Close the cap and turn
3. Get results

Concentrating by evaporation

A. Loading sample

B. Drying in progress

Drying region

C. Concentrated sample

FLUIDIC DEVICES FOR BIOSPECIMEN PRESERVATION

CROSS REFERENCE TO RELATED APPLICATION

This application claims benefit of U.S. Provisional Application No. 61/636,426, filed on Apr. 20, 2012, which is hereby incorporated by reference in its entirety.

STATEMENT REGARDING FEDERALLY SPONSORED RESEARCH

This invention was made with government support under Grant No. OD003584 and Grant No. EB012946 awarded by the National Institutes of Health and under Grant No. HR0011-11-2-0006 awarded by the Defense Advanced Research Projects Agency. The government has certain rights in the invention.

BACKGROUND OF THE INVENTION

The present invention relates to fluidic devices for preparing, processing, storing, preserving, and/or analyzing samples. In particular, such devices allow for multiple reactions to be performed while minimizing contamination.

Fluidic devices and systems are useful for conducting various types of reactions, diagnostics, and assays while minimizing sample volumes. If these devices can be simplified to operate with minimal power and/or electronic components, then such devices would particularly be useful in limited-resource settings (LRS) or in non-LRS environments that would benefit from simplified instrumentation. Current FDA-cleared LRS systems for proteins use lateral flow-type approaches such as dip-sticks, which are constrained by limitations in sensitivity, ability to quantify, and dynamic range. In addition, current LRS systems for nucleic acids provide only qualitative answers with low degree of multiplexing, and face challenges in sample preparation. Complex instrumentation is typically required for fluid handling in non-LRS diagnostic measurements, and even simple tasks such as formulation of samples for dry storage require fans and heaters. Accordingly, there is a need for fluidic devices and systems capable of manipulating small sample volumes while allowing for quantitative, multiplexed, and/or ultrasensitive diagnostics for various applications, including detection of nucleic acids or proteins.

SUMMARY OF THE INVENTION

The invention provides a fluidic device for preparing, processing, storing, preserving, and/or analyzing samples.

The invention features a device (e.g., a microfluidic device, e.g., for sample preparation, sample treatment, sample volume quantification, and/or sample analysis) including: a first layer including a plurality of first chambers; a second layer including at least one second chamber (e.g., a plurality of second chambers); and an intermediate layer disposed between the first and second layers, where the intermediate layer includes one or more capture regions, where at least one of the plurality of first chambers, at least one second chamber (e.g., at least one of the plurality of second chambers), and at least one of the one or more capture regions are able to be connected by relative movement.

In some embodiments, one or more capture regions include a filter, a matrix, a polymer, a charge switch material, or a membrane. In particular embodiments, the one or more capture regions are configured to connect two or more of the plurality of first chambers and at least one second chamber.

In further embodiments, the device includes a third layer including at least one third chamber (e.g., a plurality of third chambers), where the third layer is disposed beneath the second layer, and where at least one of the plurality of first chambers, at least one second chamber, at least one third chamber (e.g., at least one of the plurality of third chambers), and at least one of the capture regions are able to be connected by relative movement.

In some embodiments, the device (e.g., a microfluidic device, e.g., for sample preparation, sample treatment, sample volume quantification, and/or sample analysis) includes: a first layer including a plurality of first chambers; a second layer including at least one second chamber (e.g., a plurality of second chambers); and an intermediate layer disposed between the first and second layers, where the intermediate layer includes one or more capture regions, where at least one of the plurality of first chambers, at least one second chamber (e.g., at least one of the plurality of second chambers), and at least one of the one or more capture regions are able to be connected by relative movement.

The invention also features a device (e.g., a microfluidic device, e.g., for sample preservation, sample storage, sample treatment, and/or sample volume quantification) including: a first layer including a plurality of first chambers; and an intermediate layer disposed beneath the first layer, where the intermediate layer includes a membrane or one or more bridges. In some embodiments, at least one of the plurality of first chambers and the membrane or a bridge are able to be connected by relative movement. In other embodiments, at least two of the plurality of first chambers and the membrane or at least one of the one or more bridges are able to be connected by relative movement. In some embodiments, a device includes one or more reagents for the preservation of a sample.

In some embodiments, a device includes a second layer including at least one second chamber (e.g., a plurality of second chambers), where the intermediate layer is between the first layer and the second layer, and where at least one of the plurality of first chambers, at least one second chamber (e.g., at least one of the plurality of second chambers), and the membrane or at least one of the one or more are able to be connected by relative movement.

In other embodiments, a device (e.g., a microfluidic device, e.g., for sample preservation, sample storage, sample treatment, and/or sample volume quantification) includes: a first layer including a plurality of first chambers; an intermediate layer disposed beneath the first layer, where the intermediate layer includes a membrane or one or more bridges; a second layer including at least one second chamber (e.g., a plurality of second chambers); and one or more desiccants in at least one of the plurality of first chambers and/or one or more second chambers. In further embodiments, the intermediate layer is between the first layer and the second layer, and where at least one of the plurality of first chambers, at least one second chamber (e.g., at least one of the plurality of second chambers), and the membrane or at least one of the one or more are able to be connected by relative movement. In some embodiments, at least one of the plurality of first chambers and the membrane or a bridge are able to be connected by relative movement.

In some embodiments, a bridge is a channel. In other embodiments, a bridge is a chamber (e.g., a channel) in the intermediate layer, where relative movement connects the bridge to two or more first chambers. In yet other embodiments, a bridge is a chamber (e.g., a channel) in the intermediate layer, where relative movement connects the bridge to the first chamber and the second chamber. In some embodiments, a bridge is a chamber (e.g., a channel) in the intermediate layer, where relative movement connects the bridge to two or more second chambers.

In further embodiments, the device includes a third layer including at least one third chamber (e.g., a plurality of third chambers), where the third layer is beneath the second layer, and where at least one of the plurality of first chambers, at least one second chamber (e.g., at least one of the plurality of second chambers), at least one third chamber (e.g., at least one of the plurality of third chambers), and the membrane or at least one of the one or more bridges are able to be connected by relative movement.

The present invention also include devices having any combination of one or more features described herein. Accordingly, the invention features a device (e.g., a microfluidic device, e.g., for two or more of sample preservation, sample storage, sample preparation, sample treatment, sample volume quantification, and/or sample analysis) including: a first layer including a plurality of first chambers; and an intermediate layer disposed beneath the first layer, where the intermediate layer includes one or more capture regions, a membrane, or one or more bridges, where at least one of the plurality of first chambers and at least one of the following: one or more capture regions, a membrane, or one or more bridges, are able to be connected by relative movement. In some embodiments, at least one of the plurality of first chambers and at least one of the capture regions or the membrane or at least one of the one or more bridges are able to be connected by relative movement. In other embodiments, at least one of the plurality of first chambers, at least one of the capture regions, and the membrane or at least one of the one or more bridges are able to be connected by relative movement.

Accordingly, the invention also features a device (e.g., a microfluidic device, e.g., for two or more of sample preservation, sample storage, sample preparation, sample treatment, sample volume quantification, and/or sample analysis) including: a first layer including a plurality of first chambers; a second layer including at least one second chamber (e.g., a plurality of second chambers); and an intermediate layer disposed between the first and second layers, where the intermediate layer includes one or more capture regions, a membrane, or one or more bridges, where at least one of the plurality of first chambers and at least one second chamber (e.g., at least one of the plurality of second chambers) and at least one of the following: one or more capture regions, a membrane, or one or more bridges, are able to be connected by relative movement. In some embodiments, at least one of the plurality of first chambers and at least one of the capture regions or the membrane or at least one of the one or more bridges are able to be connected by relative movement. In some embodiments, at least one of the plurality of first chambers and at least one of the capture regions and the membrane or at least one of the one or more bridges are able to be connected by relative movement. In further embodiments, the device includes one or more layers, chambers, capture regions, membranes, and/or bridges, as described herein.

Accordingly, the invention features a device (e.g., a microfluidic device, e.g., for two or more of sample preservation, sample storage, sample preparation, sample treatment, sample volume quantification, and/or sample analysis) including: a first layer including a plurality of first chambers; a first intermediate layer disposed beneath the first layer, where the first intermediate layer includes one or more capture regions; a second intermediate layer disposed either between the first layer and the first intermediate layer or disposed beneath the first intermediate layer, where the second intermediate layer includes a membrane or one or more bridges, and where at least one of the plurality of first chambers and at least one of the following: one or more capture regions, a membrane, or one or more bridges, are able to be connected by relative movement. In some embodiments, at least one of the plurality of first chambers and at least one of the capture regions are able to be connected by relative movement. In some embodiments, at least one of the plurality of first chambers and the membrane or the bridge are able to be connected by relative movement. In some embodiments, at least one of the capture regions and the membrane or one or more bridges are able to be connected by relative movement. In further embodiments, the device includes a second layer including at least one second chamber (e.g., a plurality of second chambers), where the second layer is beneath the first intermediate layer or the second intermediate layer. In some embodiments, at least one second chamber (e.g., at least one of the plurality of second chambers) and at least one of the capture regions are able to be connected by relative movement. In some embodiments, at least one second chamber (e.g., at least one of the plurality of second chambers) and the membrane or bridge are able to be connected by relative movement.

The invention also features a system including a device (e.g., including a first layer including a plurality of first chambers and a through-hole that connects to at least one of the plurality of first chambers and an intermediate layer disposed beneath the first layer, or any device described herein); and a lid that encloses a cavity having volume $V_1$ and surrounds the through-hole, where closure of the lid encloses the cavity and exerts a pressure commensurate with a volume difference between the volume $V_1$ and an open system having volume $V_0$.

In some embodiments of the system, a device further includes a second layer including at least one second chamber (e.g., a plurality of second chambers), and the second layer is disposed beneath the intermediate layer.

In some embodiments, the lid further includes a buckle pump, a flexible membrane, or a pumping cup that interfaces with the through-hole.

In other embodiments, the system further includes a modified pipette tip, a modified syringe, or a porous sponge that interfaces with the through-hole for filling the plurality of first chambers or the plurality of second chambers, if present.

The invention also features a system including a device (e.g., including a first layer including a plurality of first chambers and a through-hole that connects to at least one of the plurality of first chambers and an intermediate layer disposed beneath the first layer, or any other device described herein); a housing system surrounding the device, where the housing system includes an access port that connects to the through-hole for inserting a sample; and a cap for enclosing the housing system, where closing the cap results in introducing the sample into the through-hole and/or results in relatively moving the first layer and/or the intermediate layer.

In some embodiments of the system, a device further includes a second layer including at least one second chamber (e.g., a plurality of second chambers), and the second layer is disposed beneath the intermediate layer.

In some embodiments, closing the cap results in introducing the sample into the device. In other embodiments, closing the cap results in relative movement (e.g., relatively moving the first layer and/or the intermediate layer). In yet other embodiments, closing the cap results in introducing the sample into the device and in relative movement.

In some embodiments, the cap encloses a cavity having volume $V_1$ and surrounds the through-hole, where closure of the cap encloses the cavity and exerts a pressure commensurate with a volume difference between the volume $V_1$ and an open system having volume $V_0$.

In further embodiments, the system includes a moving element (e.g., a spring mechanism, a rail system, or any described herein) configured to move the cap within the housing.

The invention also features a method of preparing and/or analyzing a sample, the method including: providing a device (e.g., any described herein, including those having one or more membranes, bridges, and/or capture regions) or a system (e.g., any described herein, including those having one or more of a cap, a lid, and/or an autonomous controller); introducing a test sample to the device or the system; and moving the first layer, the intermediate layer, and/or the second layer, if present, thereby resulting in sample preparation and/or sample analysis (e.g., where moving further optionally results in autonomous analysis of the sample).

In some embodiments, the methods further include capturing one or more analytes (e.g., any described herein) from the sample with the one or more capture regions. In other embodiments, the methods further include moving the intermediate layer to be connected by relative movement to at least one of the plurality of first chambers or at least one of the one or more second chambers. In yet other embodiments, the methods include washing one or more analytes into at least one of the plurality of first chambers or at least one of the one or more second chambers using a washing buffer (e.g., any described herein). In some embodiments, the methods include eluting one or more analytes into at least one of the plurality of first chambers or at least one of the one or more second chambers using an elution buffer (e.g., any described herein, such as an ionic liquid).

In some embodiments, sample preparation and/or sample analysis includes one or more of the following steps: partitioning the test sample into separate aliquots, filtering one or more of the aliquots, washing one or more of the aliquots, and/or quantifying the volume of one or more aliquots after partitioning, after filtering, or after washing.

In some embodiments, sample preparation includes filtering, lysing, binding, washing, eluting, assaying, and/or detecting the test sample. In other embodiments, sample preparation includes any steps described herein. In yet other embodiments, sample preparation includes nucleic acid extraction, nucleic acid purification, nucleic acid enrichment, concentrating of a nucleic acid, protein extraction, protein purification, protein enrichment, concentrating of a protein, cell separation, sample enrichment, nucleic acid amplification, nucleic acid detection, and/or protein detection.

The invention also features a method of storing and/or preserving a sample, the method including: providing a device (e.g., any described herein, including those having one or more membranes, bridges, and/or capture regions) or a system (e.g., any described herein, including those having one or more of a cap, a lid, and/or an autonomous controller); introducing a test sample to the device; and moving the first layer, the intermediate layer, and/or the second layer, if present, thereby resulting in sample storage and/or preservation (e.g., where moving further optionally results in autonomous storage and/or preservation of the sample). In some embodiments, moving results in sample analysis prior to the sample storage and/or preservation.

In some embodiments of the method, the device includes a desiccant (e.g., any described herein).

In some embodiments, sample storage and/or preservation includes one or more of the following steps: partitioning the test sample into separate aliquots, drying one or more of the aliquots, recovering one or more of the aliquots, and/or quantifying the volume of one or more aliquots after partitioning, before drying, after drying, or after recovering.

In some embodiments, sample storage and/or preservation includes filtering, lysing, dehydrating, rehydrating, binding, washing, eluting, assaying, and/or detecting the test sample. In other embodiments, sample storage and/or preservation includes nucleic acid extraction, nucleic acid purification, nucleic acid enrichment, concentrating of a nucleic acid, protein extraction, protein purification, protein enrichment, concentrating of a protein, cell separation, sample enrichment, nucleic acid amplification, nucleic acid detection, and/or protein detection.

In any of the devices, systems, and methods described herein, the sample (e.g., test sample) includes blood, plasma, serum, sputum, urine, fecal matter, sweat, spinal fluid, amniotic fluid, interstitial fluid, tear fluid, bone marrow, a swab, a tissue sample, a buccal mouthwash sample, an aerosol, a nucleic acid, a cell, a protein, and/or an enzyme, or any other sample described herein.

The invention also features a kit including one or more devices and/or systems described herein and a collector (e.g., for collecting a sample for use with the device or system, such as any described herein, including a lancet, a capillary, a needle, a syringe, a swab, a sample tube, or a microtube). In further embodiments, the kit further includes one or more substances either separate from the device or within the device. Exemplary substances include any described herein, including one or more of a sample, a washing buffer, an elution buffer, a lysis agent, a reagent, a dye, a desiccant, a stabilizer, a protein, a nucleic acid, a filter, a membrane, and/or a marker.

In any device, system, or method described herein, a layer (e.g., the intermediate layer) includes a membrane (e.g., a continuous membrane allowing for fluid communication through the entire surface of the membrane or a discontinuous (e.g., patterned) membrane having one or more regions that do not allow for fluid communication through the regions).

In any device, system, or method described herein, a layer (e.g., the first layer, the intermediate layer, or the second layer, if present) is planar or non-planar. In yet other embodiments, a layer (e.g., the first layer, the second layer, or the intermediate layer, or a portion thereof) is differentially wetted.

In any device, system, or method described herein, the device further includes a deformable layer (e.g., between the first layer and the intermediate layer and/or between the second layer and the intermediate layer). In some embodiments, the device further includes a coating (e.g., on one or more of the first layer, the intermediate layer, the second layer, or the deformable layer, if present). In particular embodiments, the coating includes a fluoropolymer (e.g., any described herein).

In any device, system, or method described herein, a layer (e.g., the first layer, the second layer, and/or the intermediate layer) translates longitudinally and/or rotates axially.

In any device, system, or method described herein, the device includes more than two layers (e.g., three, four, five, six, seven, or more layers having one or more features, such as any described herein).

In any device, system, or method described herein, the device further includes a lubricant (e.g., between the first layer and the intermediate layer and/or between the second layer and the intermediate layer and/or between the second layer and the third layer, if present). Exemplary lubricants include a hydrocarbon, a fluorous substance, an ionic liquid, a non-Newtonian fluid, a lubricating powder or bead, or an immiscible fluid (e.g., as described herein).

In some embodiments, one or more of the plurality of first chambers, one or more of the plurality of second chambers, or the one or more capture regions includes a sample, a washing buffer, an elution buffer, a lysis agent, a reagent, a dye, a desiccant, a stabilizer, a protein, a nucleic acid, a filter, a membrane, or a marker (e.g., any described herein).

In some embodiments, one or more of the plurality of first chambers or one or more of the plurality of second chambers is a well, a microchannel, or a duct.

In any device, system, or method described herein, the device or system further includes an injection port (e.g., for serial and/or sequential filling of the plurality of first chambers or at least one second chamber).

In any device, system, or method described herein, the device or system further includes one or more receiving chambers for controlling the volume of one or more fluids in the plurality of first chambers and/or at least one second chamber.

In any device, system, or method described herein, the first layer and the intermediate layer are fabricated as a single layer or the intermediate layer and the second layer are fabricated as a single layer. In some embodiments, a layer (e.g., the first layer, the intermediate layer, and/or the second layer) and a membrane are fabricated as a single layer.

For any of the devices, systems, and methods described herein, the device is a microfluidic device. In some embodiments, the microfluidic device includes at least one feature that is 1,000 μm or less in at least one dimension. In other embodiments, the feature is at least one of the plurality of first chambers, at least one second chamber, at least one feature of the membrane (e.g., dimension, pore size, etc.), at least one of the one or more bridges, and/or at least one capture region.

For any of the devices, systems, and methods described herein, sample analysis occurs with an electronic device (e.g., a cell phone, a smartphone, a mobile device, a mobile phone, a camera, a handheld camera, a video camera, an imaging device, or any detector, electronic device, or relay device described herein). In further embodiments, sample analysis includes relaying results from the sample analysis with the electronic device.

For any of the devices, systems, and methods described herein, sample storage, sample preparation, sample storage, sample treatment, sample volume quantification, and/or sample analysis occurs by use of an autonomous controller. In some embodiments, the controller includes a power element; a regulating element, which is optional and serves to maintains a relatively constant rate for the source of power; a timing element, which determines the rate of the relative movement of the device; a moving element, which promotes relative movement of the device; a transfer element, which transfers the force of the power source to the moving element and/or the timing element; and/or a switch, which is optional and serves to connect the power element either directly or indirectly to the moving element, where each of these elements can be interconnected either directly or indirectly (e.g., by a linkage, such as any described herein). Exemplary controllers are described herein.

Definitions

As used herein, "about" means+/−10% of the recited value.

By "above" is meant a relative position in which a first structure is in a higher position than a second structure. For instance, in a device including a first layer, a second layer above the first layer, and a third layer above the second layer, the term "above" provides the relative positional relationship of the first, second, and third layers and in no way signifies that the third layer must necessarily be the top or uppermost layer in the device. For instance, if the device is turned over, then the third layer would be the lowest layer in the device. Thus, it is understood that all relative positions described herein (e.g., above, beneath, between, etc.) are intended to encompass different orientations of the device in use, in operation, or during manufacture.

By "beneath" is meant a relative position in which a first structure is in a lower position than a second structure. For instance, in a device including a first layer, a second layer beneath the first layer, and a third layer beneath the second layer, the term "beneath" provides the relative positional relationship of the first, second, and third layers and in no way signifies that the first layer must necessarily be the top or uppermost layer in the device.

By "between" is meant a relative position in which an intermediate structure separates a first and a second structure. For instance, in a device including an intermediate layer disposed between a first and a second layer, the term "between" provides the relative positional relationship of the first, second, and intermediate layers and in no way signifies that the first layer must necessarily be the top or uppermost layer in the device.

By "chamber" is meant a volumetric portion of a layer capable of containing one or more substances, e.g., reagents, samples, immiscible fluids, and/or lubricants. Such chambers can have any useful structure, such as a well, a channel (e.g., a microchannel), a hole, a duct, a bridge, or a cavity having any useful cross-section or dimension(s).

By "to connect" is meant to allow for fluidic communication between two or more structures. Such fluidic communication can be between two or more similar structures (e.g., between two or more layers or between two or more chambers) or between two or more different structures (e.g., between one or more layers and one or more chambers).

By "fluidic communication" is meant the state of being able to pass a liquid or gas in a substantially unrestricted chamber. Fluidic communication can occur by any physical process, including diffusion across a membrane, active transport, or passive transport. Fluidic communication does not include limited diffusion of a substance (e.g., a reagent, sample, or fluid, as described herein) into the bulk material making up a layer.

By "immiscible fluid" is meant a first fluid (e.g., a gas or a liquid) that generally forms a different phase over certain ranges of temperature, pressure, and composition as compared to a second fluid. In some embodiments, the second fluid is an aqueous solution, a sample for storage, preservation, processing, or analysis, and/or a reagent for storing, preserving, processing, or analyzing the sample; and the first fluid is a fluid that is immiscible with one or more of the second fluids at certain ranges of temperature, pressure, and composition useful for storing, preserving, processing, or analyzing the sample.

By a "microfluidic" structure is meant a structure having at least one feature that is 1,000 μm or less in at least one dimension. Exemplary features include a layer (e.g., the thickness of a layer or the length, width, or height of a component embedded within a layer), a chamber (e.g., a well, a channel, a hole, a duct, a bridge, or a cavity), a membrane (e.g., the thickness of a membrane or the length, width, or height of a component (e.g., one or more pores or other physical structures) embedded within a membrane), or a capture region. In some embodiments, the structure includes more than one, two, three, four, five, six, seven, eight, nine, ten, twenty, or more features that are 1,000 μm or less in at least one dimension (e.g., height, width, depth, or thickness).

BRIEF DESCRIPTION OF THE DRAWINGS

In FIG. 2F, only one of the samples (i.e., sample 245 in the left chamber) is rehydrated, while the other sample (i.e., sample 243 in the right chamber) remains preserved and can be stored for further recovery at a later time, if desired.

The exemplary sample module includes sample chambers in the top layer 310 and a porous material 315 (mesh filling). B: Samples 311 and 312 are loaded in the chambers in the top layer. C: The sample module is combined with a drying module 320, including a chamber containing desiccant 321, thereby initiating preservation. D: Preserving is complete when desiccant 322 has absorbed or adsorbed the solvent (e.g., water) from the sample, and preserved (e.g., in dry or liquid state) or concentrated residual substances 313 and 314 are present in the sample chambers. E: The sample module is separated from the drying module. F: Water or any useful solvent (e.g., a buffer) can be injected to provide a rehydrated sample 335. Rehydration can be performed on an array of sample chambers, or just a subset of such chambers. In FIG. 3F, only one of the samples (i.e., sample 335 in the left chamber) is rehydrated, while the other sample (i.e., sample 313 in the right chamber) remains preserved and can be stored for further recovery at a later time, if desired.

In FIG. 4D, only one of the samples (i.e., sample 425 in the left chamber) is rehydrated, while the other sample (i.e., sample 413 in the right chamber) remains preserved and can be stored for further recovery at a later time, if desired.

FIGS. 18A-18B show schemes for an exemplary rotational SlipChip for sample preparation in a perspective view (A) and exploded view (B). A: The device 1800 includes a housing system having a top portion 1801 and a bottom portion 1802, where the top portion includes a sample chamber 1811 including a capture region 1821 (e.g., a membrane), one or more wash buffer chambers 1812, and one or more elution buffer chambers 1813. "P" indicates positive pressure, and "M" indicates membrane. B: The device 1800 includes a first layer 1810 (Layer-1), a second layer 1820 (Layer-2) including a capture region 1821 (e.g., a filter), a third layer 1830 (Layer-3) including a through hole 1835 and a plurality of receiving chambers 1830 (e.g., receiving well), and a fourth layer 1840 (Layer-4) including a post 1845 for connecting to the second layer. The first layer includes a chamber for the sample 1811, the washing buffer 1812, and the elution buffer 1813. As shown in FIG. 18A, the first layer can include more than one chamber for the washing buffer and/or elution buffers to effect more than one washing and/or eluting steps. As shown in (i), the first and second layers are relatively moved to connect the sample chamber, the capture region, and one of the receiving wells. Pressure is then applied to transport the sample through the capture region and into the aligned receiving well, where the desired analyte is captured in the capture region. As shown in (ii), the relative movement of the second layer (e.g., by rotating the fourth layer that is connected to the second layer) results in connecting the capture region, the washing chamber, and a second receiving well. Pressure is applied to transport the wash buffer through the capture region, thereby performing the washing step. As shown in (iii) and (iv), the relative movement of the second layer (e.g., by rotating the fourth layer that is connected to the second layer) results in connecting the capture region, the elution chamber, and a third receiving well. Pressure is applied to transport the elution buffer through the capture region, thereby performing the eluting step. Relative movement can include any useful movement (e.g., rotating the top portion 1801 of the device or rotating the bottom portion 1802 of the device) that moves the layers relative to the chamber or capture region including the sample and/or analyte. In particular embodiments, the top and/or bottom portions 1801 and 1802 of the device can include markings (see, e.g., F, S, and W1-W4 indications provided on the edge of the device in FIGS. 18A and 20A-20D) that indicate the location of the chambers including the sample, wash buffer(s), or elution buffer(s).

As shown in FIG. 20D, the top portion 2001 is rotated relative to the bottom portion 2002 in this particular, non-limiting device.

In FIG. 60 (top), this rate of fluidic communication is increased by increasing the contact area between the membrane with the chamber containing a desiccant. In this manner, the concentration of the target analyte can be increased on a short time scale. Alternatively, the concentration can be increased by increasing the timescale for evaporation (FIG. 60, middle). Further, these strategies can be combined (bottom), where a maximum concentrating factor can be achieved if the volume of sample introduced to the device in a given time is the same as the volume of solvent removed by evaporation. This strategy creates a steady state with a constantly increasing concentrating factor.

DETAILED DESCRIPTION

Figure 1:
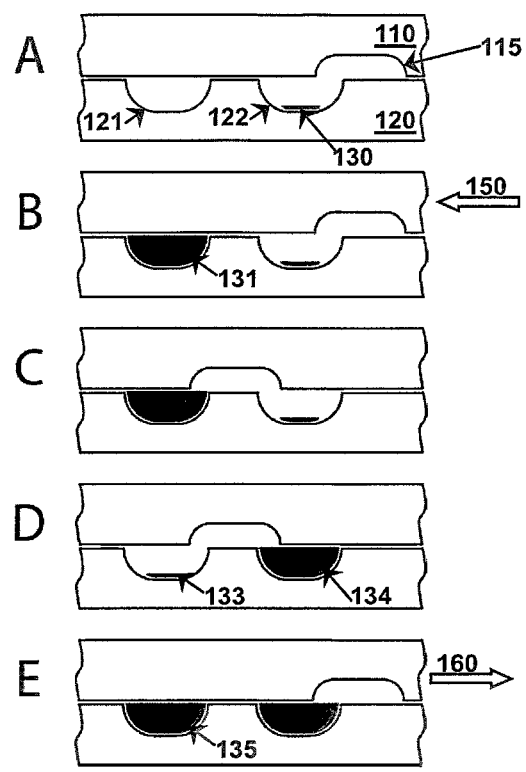
FIGS. 1A-1E provide exemplary schemes for a preserving a specimen using a device having a bridge. A: The assembled device includes a sample chamber 121 (in bottom layer 120), a chamber 122 preloaded with a desiccant 130 (in bottom layer 120), and a bridge 115 (in top layer 110). B: The sample 131 is loaded in a sample chamber, and the top layer is moved (block arrow 150) relative to the bottom layer. C: Relative movement aligns the chambers with the bridge, allowing for vapor contact between the sample and desiccant and beginning the drying process. D: Preserving (e.g., drying) is complete when the desiccant has absorbed or adsorbed the solvent (e.g., water) from the sample, as evidenced by the presence of a hydrated desiccant 134 and a preserved (e.g., in dry or liquid state) or concentrated residual substance 133 in the sample chamber. E: Relative movement is performed (block arrow 160) to disconnect the chambers from the bridge, and solvent can be introduced in the device to provide a rehydrated sample 135.

The invention provides devices and methods for preparing, processing, storing, preserving, and/or analyzing samples. In particular, such devices allow for multiple reactions to be performed while minimizing contamination. Described herein are structural features for such devices, as well as methods for their use in sample preparation or storage.

Devices

The devices of the invention can include one or more structural features, such as a layer, a chamber (e.g., a well, a channel, a hole, a bridge, or a cavity, or any described herein), or a capture region. In particular, the chamber can be completed or partially enclosed (e.g., such as in an enclosed channel) or be open (e.g., such as in a well). The various structures described herein can have any useful dimension, cross-section, planarity, or surface characteristic. Any of the devices described herein can be used individually or in combination with the devices or with one or more features of the devices described in, e.g., U.S. Pub. Nos. 2006-0003439; 2007-0172954; 2010-0078077; 2010-0233026; 2011-0112503; 2011-0142734; 2011-0165037; 2011-0176966; 2011-0177586; and 2012-0329171; U.S. Pat. Nos. 7,129,091; 7,655,470; 7,901,939; 8,304,193; 8,273,573; and 8,329,407; U.S. patent application Ser. No. 13/648,922, filed Oct. 10, 2012; Int. Pub. Nos. WO 2004/038363; WO 2009/149257; WO 2008/079274; and WO 2006/101851; and U.S. Provisional Pat. Appl. Nos. 60/379, 927; 60/394,544; 60/585,801; 60/623,261; 60/763,574; 60/875,856; 60/881,012; 60/899,449; 60/930,316; 60/936, 606; 60/962,426; 61/130,930; and 61/335,570. Further, any of these devices can be used in any method described herein, as well as those methods described in the above-mentioned U.S. Pat. Nos., U.S. Pub. Nos., U.S. Pat. Appl. No., Int. Pub. Nos., and U.S. Provisional Pat. Appl. Nos., which are incorporated herein by reference.

Dimensions and Cross-Sections

The layer, chamber, capture region, or other structure can include any useful dimension. Useful dimensions include any length, width, or depth that can be uniform or varied along any useful axis. Exemplary dimensions in any useful axis (e.g., perpendicular to the axis of fluid flow) include less than about 50 mm (e.g., less than about 40 mm, 20 mm, 15 mm, 10 mm, 5 mm, 2 mm, 1 mm, 500 µm, 200 µm, 60 µm, 50 µm, 40 µm, 30 µm, 15 µm, 10 µm, 3 µm, 1 µm, 300 nm, 100 nm, 50 nm, 30 nm, or 10 nm) or from about 10 nm to about 50 mm (e.g., 10 nm to 40 mm, 10 nm to 20 mm, 10 nm to 15 mm, 10 nm to 10 mm, 10 nm to 5 mm, 10 nm to 2 mm, 10 nm to 1 mm, 10 nm to 500 µm, 10 nm to 200 µm, 10 nm to 60 µm, 10 nm to 50 µm, 10 nm to 40 µm, 10 nm to 30 µm, 10 nm to 15 µm, 10 nm to 10 µm, 10 nm to 3 µm, 10 nm to 1 µm, 100 nm to 50 mm, 100 nm to 40 mm, 100 nm to 20 mm, 100 nm to 15 mm, 100 nm to 10 mm, 100 nm to 5 mm, 100 nm to 2 mm, 100 nm to 1 mm, 100 nm to 500 µm, 100 nm to 200 µm, 100 nm to 60 µm, 100 nm to 50 µm, 100 nm to 40 µm, 100 nm to 30 µm, 100 nm to 15 µm, 100 nm to 10 µm, 100 nm to 3 µm, 100 nm to 1 µm, 1 µm to 50 mm, 1 µm to 40 mm, 1 µm to 20 mm, 1 µm to 15 mm, 1 µm to 10 mm, 1 µm to 5 mm, 1 µm to 2 mm, 1 µm to 1 mm, 1 µm to 500 µm, 1 µm to 200 µm, 1 µm to 60 µm, 1 µm to 50 µm, 1 µm to 40 µm, 1 µm to 30 µm, 1 µm to 15 µm, 1 µm to 10 µm, 1 µm to 3 µm, 10 µm to 50 mm, 10 µm to 40 mm, 10 µm to 20 mm, 10 µm to 15 mm, 10 µm to 10 mm, 10 µm to 5 mm, 10 µm to 2 mm, 10 µm to 1 mm, 10 µm to 500 µm, 10 µm to 200 µm, 10 µm to 60 µm, 10 µm to 50 µm, 10 µm to 40 µm, 10 µm to 30 µm, 10 µm to 15 µm, 50 µm to 50 mm, 50 µm to 40 mm, 50 µm to 20 mm, 50 µm to 15 mm, 50 µm to 10 mm, 50 µm to 5 mm, 50 µm to 2 mm, 50 µm to 1 mm, 50 µm to 500 µm, 50 µm to 200 µm, 50 µm to 60 µm, 100 µm to 50 mm, 100 µm to 40 mm, 100 µm to 20 mm, 100 µm to 15 mm, 100 µm to 10 mm, 100 µm to 5 mm, 100 µm to 2 mm, 100 µm to 1 mm, 100 µm to 500 µm, or 100 µm to 200 µm).

The dimensions of any structure (e.g., one or more chambers) may be chosen to maintain a particular volumetric or linear flow rate of a fluid in the device. For example, such dimensions may be useful to control the filling of the device with particular fluids or the flow rate of such fluids through the areas and/or capture regions.

The layer, chamber, capture region, or other structure can include any useful cross-section. Cross-sections can be of any useful shape (e.g., rectangular, square, circular, oval, irregular, or triangular cross-sections) that can optionally vary along the axis of any structure. For instance, when the structure is a channel, the cross-section of the channel along the axis of fluid flow can change from one cross-sectional shape to another, such as from a circular to a rectangular cross-section. In another instance, the dimensions of the cross-section can be uniform or can vary along any axis, such as a channel that tapers or expands along the axis of fluid flow.

Planarity

The layer, chamber, capture region, or other structure can include any useful planarity. In some instances, the surfaces of the first and second layers are substantially planar to facilitate movement of these layers. Such layers can further be uniform or non-uniform in other characteristics, such as height, width, and/or depth.

Alternatively, the surfaces of the structures can be non-planar and substantially complementary to allow for movement. For instance, one or more layers can include a curvilinear surface, such as the surface of a cylinder, a concave surface, or a convex surface. In one example, the first layer can include a first cylindrical surface, and the second layer includes an annular cylinder having an opening, an inner cylindrical surface, and an outer cylindrical surface. When the first layer is inserted into the opening of second layer, the first cylindrical surface and the inner cylindrical surface of the second layer are complementary, thereby allowing the first layer to move within the second layer. Accordingly, the layers can include any useful complementary surfaces, such as concentric spheres, cones, cylinders, etc.

Further, the device can include additional layers having any useful planarity, and each layer can have similar, different, or complementary structure characteristics (e.g., planarity). Moreover, to ensure that uniform pressure is applied over the first and second areas or layers, the surface may vary to ensure when pressure is applied in discrete locations along the device, a uniform pressure can be applied. For example, when the two surfaces are conical, pressure may be applied to bring two surfaces into close contact. Exemplary devices and their characteristics are described in U.S. Pub. No. 2012-0028342, U.S. Pub. No. 2012-0264132, U.S. Pub. No. 2012-0329038, Int. Pub. No. WO 2010/111265, as well as U.S. Provisional Application No. 61/162,922, filed Mar. 24, 2009; 61/262,375, filed Nov. 18, 2009; 61/340,872, filed Mar. 22, 2010; 61/516,628, filed Apr. 5, 2011; and 61/518, 601, filed on May 9, 2011, each of which is incorporated herein by reference in its entirety.

Surface Characteristics

The layer, chamber, capture region, or other structure can include any useful surface characteristics. Exemplary surface characteristics include differentially wetting (e.g., hydrophobic, lipophobic, fluorophilic, or hydrophilic), smoothness, or porosity. Each layer can have substantially the same or different surface characteristics. For instance, both the first and second layers can be substantially hydrophobic, or the first layer can be substantially hydrophobic, and the second layer can be substantially hydrophilic. Similarly, each of the first chambers of the first layer can have substantially the same or different surface characteristics. In one example, all of the first chambers are substantially hydrophilic, and the remaining portions of the first layer are hydrophobic, thereby allowing for preferentially wetting of aqueous reagents within the first chambers as compared to other portions of the first layer. In another example, the entire first layer, including the first chambers, are substantially fluorophilic, and the capture regions are substantially hydrophilic. In this way, aqueous reagents and/or samples will preferentially flow through capture regions, as compared to remaining in the first layer. Furthermore, if the lubricant is a fluorous liquid, then this fluid will preferentially wet the first chamber as compared to the capture regions. As can be seen, by controlling the surface characteristics, fluid flow and/or compartmentalization can be controlled. For example, where an open chamber (e.g., an open well) is used, a fluid may be held within an open chamber using surface tension (i.e., a concave or convex meniscus), particularly if the open chamber has a surface characteristic allowing for preferentially wetting of the fluid.

Surface characteristics can be obtained by using any useful material or surface modification process. For instance, one or more chambers can include porous materials, e.g., porous glass, aluminum oxide, or a cellulose matrix. Such chambers may be made by depositing a matrix into the area, by patterning a porous layer, and/or by filling or coating a porous layer around areas. Exemplary cellulose patterning processes are described in Martinez et al., Anal. Chem. 80:3699-3707 (2008), Martinez et al., Angew. Chemie Int. Ed. 46:1318-1320 (2007), Martinez et al., Lab Chip 8:2146-2150 (2008), and Macek et al., Chromatographic Rev. 15:1-28 (1971); and other materials may be patterned by methods described in Vozzi et al., Biomaterials 24:2533-2540 (2003) for PLGA scaffolds; Desai et al., Biosens. Bioelectron. 15: 453-462 (2000), Pichonat et al., J. Micromech. Microeng. 15:S179-S184 (2005), Cohen et al., Biomed. Microdevices 5:253-259 (2003), Ohji et al., Proc. SPIE Int'l Soc. Optical Eng. 3223:189-197 (1997), and Chu et al., J. Microelectromech. Sys. 15: 671-677 (2006) for porous silicon membranes; De Jong et al., Lab Chip 5: 1240-1247 (2005) for thin devices; Petronis et al., J. Biomed. Mater. Res. 66:707-721 (2003) for silicon substrates; and Wang et al., Sens. Actuat. B 123:101-106 (2007) for palladium-silver thin film for hydrogen sensing, each of which is incorporated herein by reference in its entirety.

The layer, chamber, capture region, or other structure can be formed from any useful material. The materials used to fruit the devices of the invention are selected with regard to physical and chemical characteristics that are desirable for proper functioning of the device. Suitable, non-limiting materials include polymeric materials, such as silicone polymers (e.g., polydimethylsiloxane and epoxy polymers), polyimides (e.g., commercially available Kapton® (poly(4, 4'-oxydiphenylene-pyromellitimide, from DuPont, Wilmington, Del.) and Upilex™ (poly(biphenyl tetracarboxylic dianhydride), from Ube Industries, Ltd., Japan)), polycarbonates, polyesters, polyamides, polyethers, polyurethanes, polyfluorocarbons, fluorinated polymers (e.g., polyvinylfluoride, polyvinylidene fluoride, polytetrafluoroethylene, polychlorotrifluoroethylene, perfluoroalkoxy polymer, fluorinated ethylene-propylene, polyethylenetetrafluoroethylene, polyethylenechlorotrifluoroethylene, perfluoropolyether, perfluorosulfonic acid, perfluoropolyoxetane, FFPM/FFKM (perfluorinated elastomer [perfluoroelastomer]), FPM/FKM (fluorocarbon [chlorotrifluoroethylenevinylidene fluoride]), as well as copolymers thereof), polyetheretherketones (PEEK), polystyrenes, poly(acrylonitrile-butadiene-styrene) (ABS), acrylate and acrylic acid polymers such as polymethyl methacrylate, and other substituted and unsubstituted polyolefins (e.g, cycloolefin polymer, polypropylene, polybutylene, polyethylene (PE, e.g., cross-linked PE, high-density PE, medium-density PE, linear low-density PE, low-density PE, or ultra-high-molecular-weight PE), polymethylpentene, polybutene-1, polyisobutylene, ethylene propylene rubber, ethylene propylene diene monomer (M-class) rubber), and copolymers thereof (e.g., cycloolefin copolymer); ceramics, such as aluminum oxide, silicon oxide, zirconium oxide, and the like); semiconductors, such as silicon, gallium arsenide, and the like; glass; metals; as well as coated combinations, composites (e.g., a block composite, e.g., an A-B-A block composite, an A-B-C block composite, or the like, of any materials described herein), and laminates (e.g., a composite material formed from several different bonded layers of identical or different materials, such as polymer laminate or polymer-metal laminates, e.g., polymer coated with copper, a ceramic-in-metal or a polymer-in-metal composite) thereof.

The device can be formed by any useful process, including but not limited to molding (e.g., injection molding, vacuum molding, or overmolding), machining (e.g., drilling, milling, or sanding), and etching (e.g., deep reactive ion etching, KOH etching, or HF etching). In microfluidic applications, the layers can be fabricated from a material that enables formation of high resolution features (e.g., microchannels, chambers, mixing features, and the like, that are of millimeter, micron, or submicron dimensions), such as by using microfabrication techniques (e.g., dry etching, wet etching, laser etching, laser ablation, molding, embossing, or the like, to have desired miniaturized surface features). Further, the material can be optionally treated to provide a chemically inert surface (e.g., by silanization with tridecafluoro-1,1,2,2-tetrahydrooctyl-1-trichlorosilane), a biocompatible surface (e.g., by treatment with bovine serum albumin), and/or a physically stable material (e.g., by extensive cross-linking).

The layers can include any useful material. For instance, a portion of a layer can include a membrane, or the entire layer can include a continuous membrane or a patterned membrane. Furthermore, such membranes can be integrated with one or more layers (e.g., by overmolding or lamination) having one or more chambers and/or inlets. Alternatively, such membranes can be present in a separate layer. Exemplary membranes include a PTFE (e.g., Teflon®) membrane, a polycarbonate membrane, a cellulose membrane, a nitrocellulose membrane, a nylon membrane, a paper membrane, or other membranes that are known in the art.

The device can also include one or more deformable layers. Such deformable layers can be designed to deform as pressure is applied, such as to redistribute local pressure into uniform pressure over a surface of the device and/or to control connection or disconnection between layers or chambers.

Furthermore, one or more layers and/or chambers can be optionally coated. In particular embodiments, a coating is used to minimize cross-contamination between layers, where relative movement between layers can result in thin films of reagents forming between layers. The coating can be used to control surface chemistry (e.g., by increasing the contact angle to about 154° with water). In particular embodiments, one or more layers and/or chambers are coated with a fluoropolymer. Exemplary fluoropolymers include fluorinated ethylene propylene resin (e.g., Teflon® FEP TE-9568, a dispersion composed of approximately 54% (by total weight) of a negatively charged, hydrophobic colloidal fluoropolymer resin (0.1 to 0.30 μm FEP particles suspended in water) and approximately 6% (by weight of FEP resin) of a nonionic wetting agent and stabilizer based on the weight of the FEP solids), perfluoroalkoxy copolymer resin (e.g., Teflon® PFA TE-7224, a dispersion composed of approximately 60% (by total weight) of PFA resin (0.05 to 0.5 μm particles) dispersed in water and approximately 5% by weight of a nonionic wetting agent and stabilizer based on the weight of the PFA solids; or Teflon® PFAD 335D, a dispersion composed of approximately 60% (by total weight) of PFA resin (0.20 μm average diameter particles) dispersed in water and approximately 6% by weight of a nonionic surfactant based on the weight of the PFA solids), polytetrafluoroethylene (e.g., Teflon® PTFE DISP 30, a dispersion composed of approximately 60% (by total weight) of PTFE resin (0.220 μm average diameter particles) dispersed in water and approximately 6% by weight of a nonionic surfactant based on the weight of the PTFE solids), or a copolymer of tetrafluoroethylene and ethylene (e.g., Tefzel® Type LZ, CLZ, or CLZ-20, available in nominal gauges of 50, 100, 200, 500, 750, 1000, or 2000, having a thickness of 0.0005, 0.0010, 0.0020, 0.0050, 0.0075, 0.0100, or 0.0200 inches).

Figure 7:
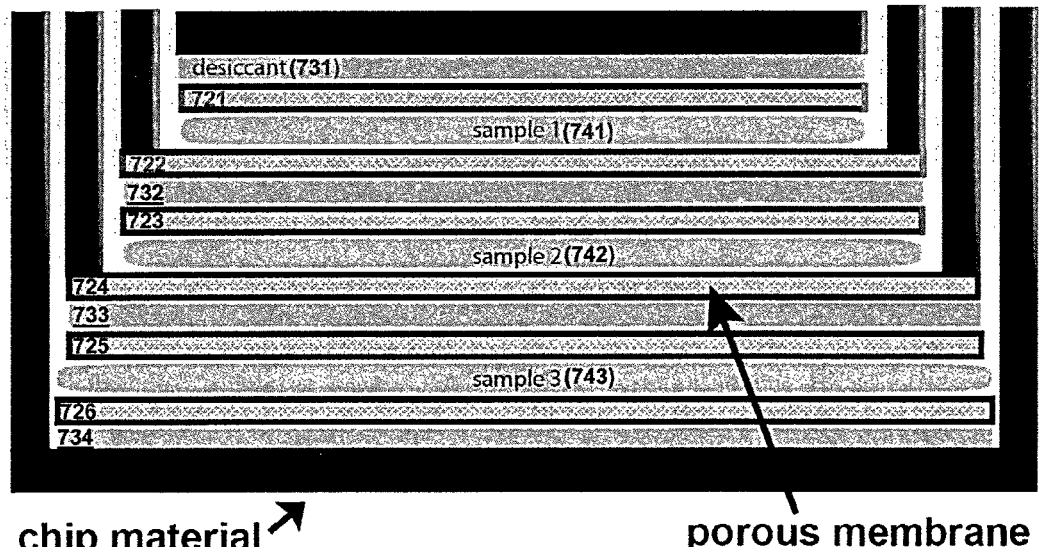
FIG. 7 provides an exemplary scheme of a multilayer device to increase storage capacity of the number and/or amount of samples. The device includes multiple layers including a porous membrane 720 (layers 721-726) and chambers for a desiccant (chambers 731-734) and multiple chambers for samples 741-743, where the layers and chambers can be formed from any useful material 710, as described herein.
Figure 9:
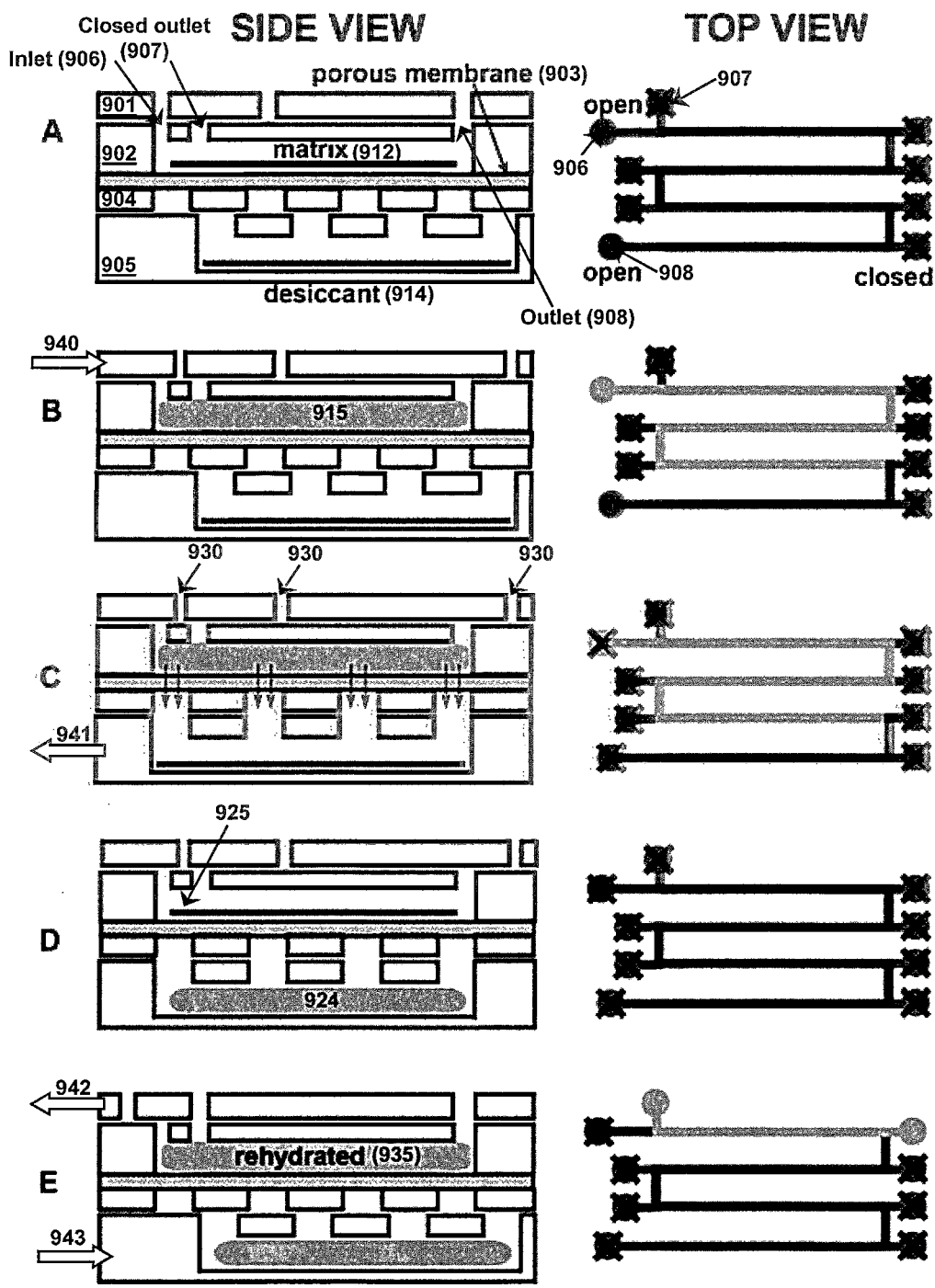
FIGS. 9A-9E provide exemplary schemes for a multilayered sample storage device in side view (left) and top view (right). A: The device includes a first layer 901 (top layer) having via holes 930, a second layer 902 (an intermediate layer) including a chamber for matrix 912 and a porous membrane 903, a third layer 904 including a plurality of openings for fluidic communication between the second layer 902 and the fourth layer 905, and a fourth layer 905 (bottom layer) including a chamber for desiccant 914. In some embodiments, the second and third layers can be laminated or combined into a single layer. B: Introducing a sample (top view) and closing the valves (as indicated by arrow 940) by relative movement of top layer 901 results in a combined sample 915 with the matrix. C: Relative movement of the fourth layer (bottom layer, as indicated by arrow 941) results in fluidic communication (e.g., vapor contact shown by arrows) between the chambers in the first layer (top layer) and the fourth layer (bottom layer) (side view), and closing all the valves in the device initiates drying (top view). D: Drying is complete when the desiccant has absorbed or adsorbed the solvent (e.g., water) from the sample, as evidenced by the presence of hydrated desiccant 924 and a dry residual substance 925 in the sample chamber. E: Rehydration can be achieved by opening the valves (top view) and injecting any useful solvent (e.g., a buffer) to provide a rehydrated sample 935. The top view (right) provides how selective rehydration can be achieved by opening and closing selected inlets or outlets, where X indicates a closed inlet or outlet. Such a multilayered device can be used to create reversible vapor contact between the sample and the desiccant. The geometry can be adapted to optimize drying (e.g., by increasing the quantity of desiccant and/or by controlling the reversible contact area), while allowing for partial recovery on longer timescales. Further, sequential filling can be used to precisely quantify the injected volume and to control partial recovery of the filled chambers. Inlets and outlets can be placed in the intermediate layer 902. The top layer 901 can include via holes 930 for a valving system. Slipping the layers (as indicated by arrows 940 and 942) can align/misalign the via holes 930 with inlets and outlets, thereby providing a valving system. For instance, in FIG. 9A, alignment of the via holes 930 with both the inlet 906 and outlet 908 results in an open inlet 906 and an open outlet 908. Misalignment of the via holes with an outlet results in a closed outlet 907. Slipping of the layers (as indicated by arrow 940) results in closing inlet 906 and outlet 908 (FIG. 9C, right). Further slipping of the layers (as indicated by arrow 942) aligns the via holes with the outlets, thereby resulting in open outlets 907 and 908. Moving of the bottom layer (as indicated by arrows 941 and 943) create reversible vapor contact between the sample and the desiccant.

The device can include multiple layers to accommodate multiplexed sample processing, preparation, and/or analysis (see, e.g., FIGS. 7 and 9). In particular embodiments, the layers are provided in a stacked configuration having a top layer, a bottom layer, and a plurality of intermediate layers. The intermediate layers can have one or more openings and/or capture regions such that various chambers and/or capture regions are able to be connected by relative movement. Each of the layers can be connected and disconnected separately from the other layers within the stack. In this manner, connections and disconnections between layers can be controlled to perform the desired reactions or multiplexed analysis.

Figure 10:
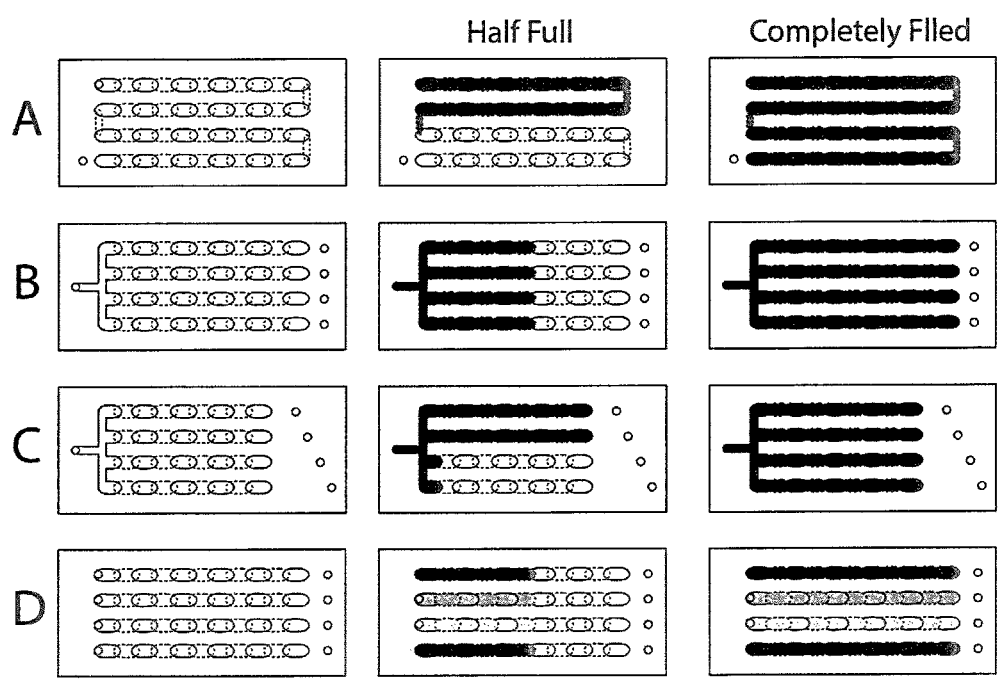
FIGS. 10A-10D provide exemplary schemes showing strategies for device filling. A: Sequential filling can be achieved by designing a single pathway that fluidically connects the plurality of chambers upon relatively moving the layers of a SlipChip. B: Parallel filling can be achieved by designing a branched pathway, where each branch fluidically connects a subset of a plurality of chambers upon relatively moving the layers of a SlipChip. C: Combined sequential and parallel filling can be achieved by designing a branched pathway (as in FIG. 10B) and then modifying the distance between the inlet and the outlet (empty circles on right side of device) for each pathway. By increasing the distance between the inlet and outlet for a particular pathway, the relative pressure required to fill the chamber is increased, thereby resulting in a slower fill rate. In this manner, the evacuation rate of a fluid can be tuned, and filling of one row at a time can be achieved in this way. D: Multiplex filling can be achieved by providing each array of a plurality of chambers with a separate inlet, where four arrays and four separate inlets are provided in this scheme for example only. In this way, multiple inlet holes are used to load different samples at the simultaneously or sequentially. For FIGS. 10A-10D, the devices are loaded based on dead-end filling. Only the gap between the two SlipChip layers connects the main filling channels to the outlets. In this way, the filling liquid (e.g., water, a reagent, a sample, or any substance described herein) is confined in the channels, while the immiscible phase (e.g., a lubricant) can be evacuated from the channels to the outlets through the gap.
Figure 11:
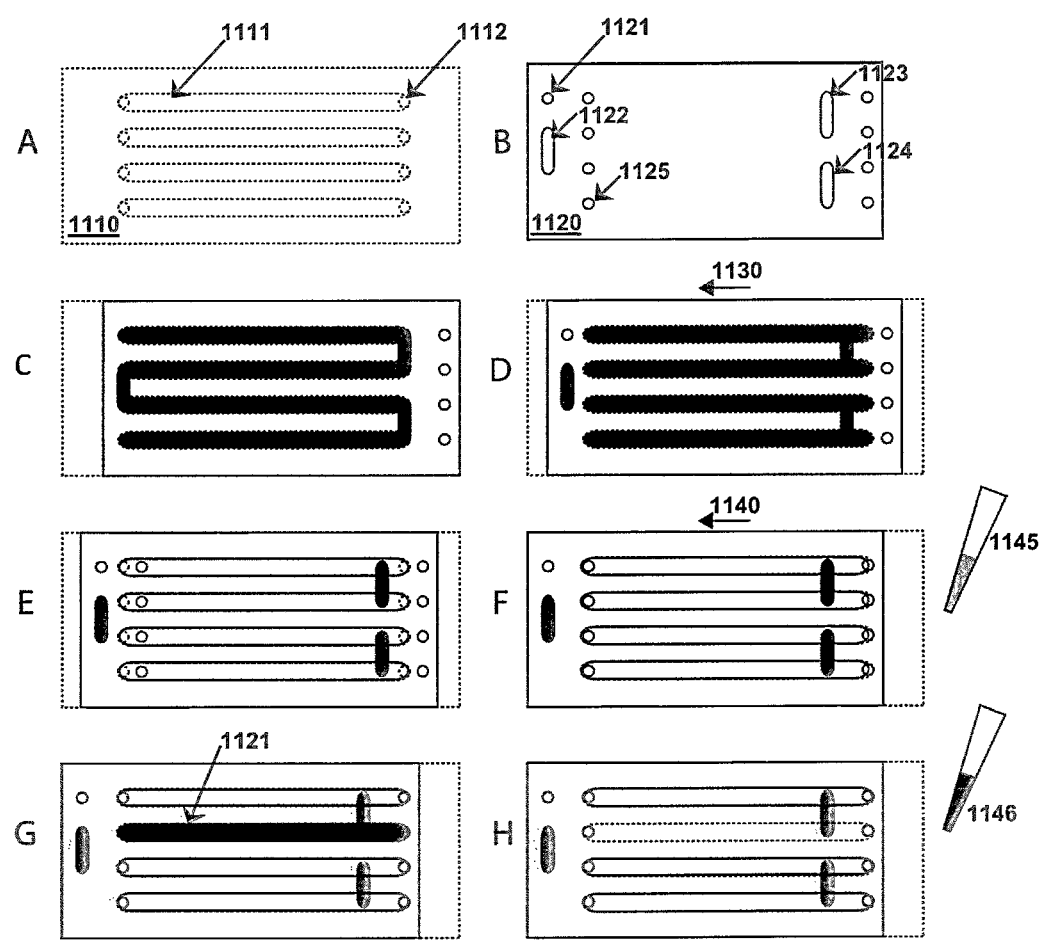
FIGS. 11A-11H provide exemplary schemes showing strategies for device filling (or loading), drying, and partial recovery. A: The bottom layer 1110 (storage module) includes four chambers 1111 and eight via holes 1112 (circles). B: The top layer 1120 includes one inlet 1121 for filling, three chambers 1122-1124 capable of fluidic communication with chambers 1111 in the bottom layer, and eight via holes 1125 (circles). C: Relative movement connects the chambers to form a single path that can be filled sequentially as in FIG. 10A. D: Another relative movement (arrow 1130, e.g., by slipping) disconnects the chambers in the top layer and the bottom layer, as well as activates drying. E: After drying, the device includes dried or preserved sample within the chambers. F: Relative movement (arrow 1140, e.g., by slipping) connects the chambers with the via holes in the top layer, and the device is now ready for rehydration (e.g., by injecting water with pipettor 1145). G: Injection of a solvent (e.g., water) through the via holes allows rehydration of the second chamber 1121. H: Sample is recollected from the second chamber (e.g., by using a pipettor 1146), while the other chambers still contain dried sample that can be recovered at a different time. Such strategies an used for liquid storage or for aliquoting a solution.
Figure 12:
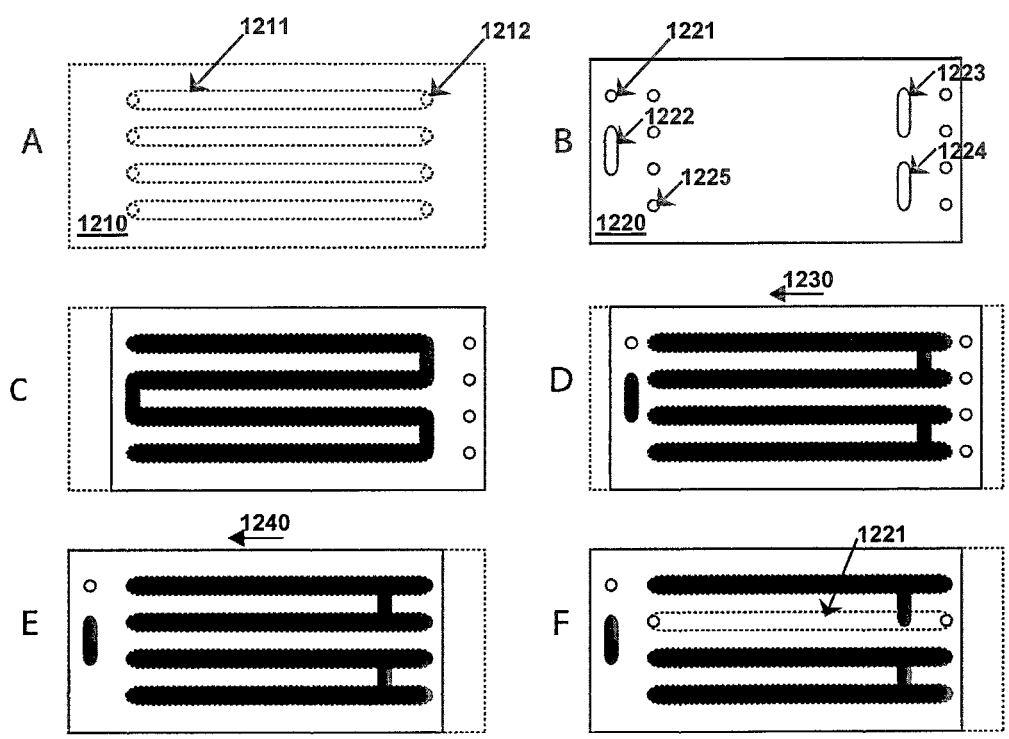
FIGS. 12A-12F provide exemplary schemes showing strategies for device filling (or loading), drying, and partial recovery. A: The bottom layer 1210 (storage module) includes four chambers 1211 and eight via holes 1212 (circles). B: The top layer 1220 includes an inlet 1221 for filling, three chambers 1222-1224 capable of fluidic communication with chambers 1211 in the bottom layer, and eight via holes 1225 (circles). C: Relative movement connects the chambers to form a single path that can be filled sequentially as in FIG. 10A. D: Another relative movement (arrow 1230, e.g., by slipping) disconnects the chambers in the top layer and the bottom layer, thereby creating aliquots. Storage can optionally occur in this position. E: Another relative movement (arrow 1240, e.g., by slipping) aligns the chambers with the via holes in the top layer, thereby preparing the device for recovery. F: Recovery of the aliquot in the second well 1221 can be achieved (e.g., by using a pipettor). Other aliquots can be recovered in a similar manner, and the device can also be stored (e.g., as shown in FIG. 12D) for later recovery.

The layers can include a plurality of chambers, where each chamber may be the same or different. Furthermore, a plurality of arrays of such chambers can be present in one or more layers (e.g., see arrays in FIG. 10, which can be connected sequentially or serially). Such chambers can include any volumetric structure. Each chamber in a layer or an array may have the same surface dimension, cross-section, planarity, or surface characteristic. Alternatively, each chamber in a layer or an array may have different surface dimensions, cross-sections, planarity, or surface characteristics. Exemplary chambers include an open groove or trench, a closed channel, an open or closed well, etc. Such chambers are useful for holding or transporting one or more reagents, samples, or fluids (e.g., a lubricant).

One exemplary chamber is a bridge, which can allow for connecting two other chambers in the same layer or two other chambers, each in a separate layer. The surface dimensions, cross-sections, planarity, or surface characteristics of the bridge can be optimized to promote rapid vapor diffusion or fluidic communication, such as in devices for sample storage or preservation. In some embodiments, the bridge is not preferentially wetted by liquid water under the conditions of device use (e.g., the surface of the bridge is substantially hydrophobic and/or the bridge is filled with a gas). In some embodiments, the bridge and the distance between two chambers is less than about 500 μm (e.g., less than about 300 μm, 100 μm, 50 μm, or 20 μm).

Movement of Layers

The devices of the invention include layers that allow for connection and disconnection of one or more chambers by relative movement. For example, in a first position, a first chamber is not connected to a second chamber (i.e., the first chamber does not fluidically communicate with the second chamber). Upon moving the first chamber relative to the second chamber, a connection is formed. This movement can be accomplished by moving the first layer having the first chamber relative to the second layer. Alternatively, this movement can include moving the second layer having the second chamber relative to the second layer. The connection between chambers can also occur via a capture region, a bridge, a membrane, or any other structure described to provide fluidic communication between a first and second chamber.

Figure 25:
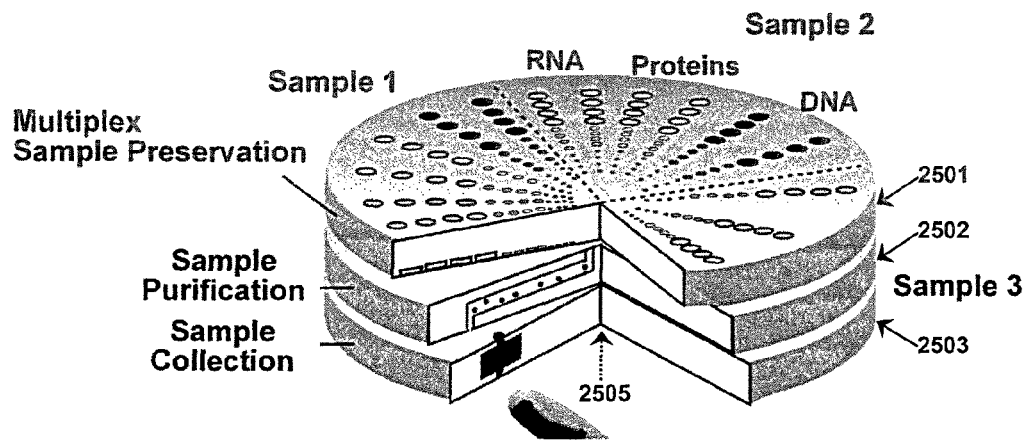
FIG. 25 provides an exemplary scheme for multiplexed sample preservation. The device includes three layers 2501-2503 for multiplex sample preservation, sample purification, and sample collection, respectively. Each of three samples are collected, purified, and split to store three analytes (e.g., DNA, RNA, and proteins).
Figure 26:
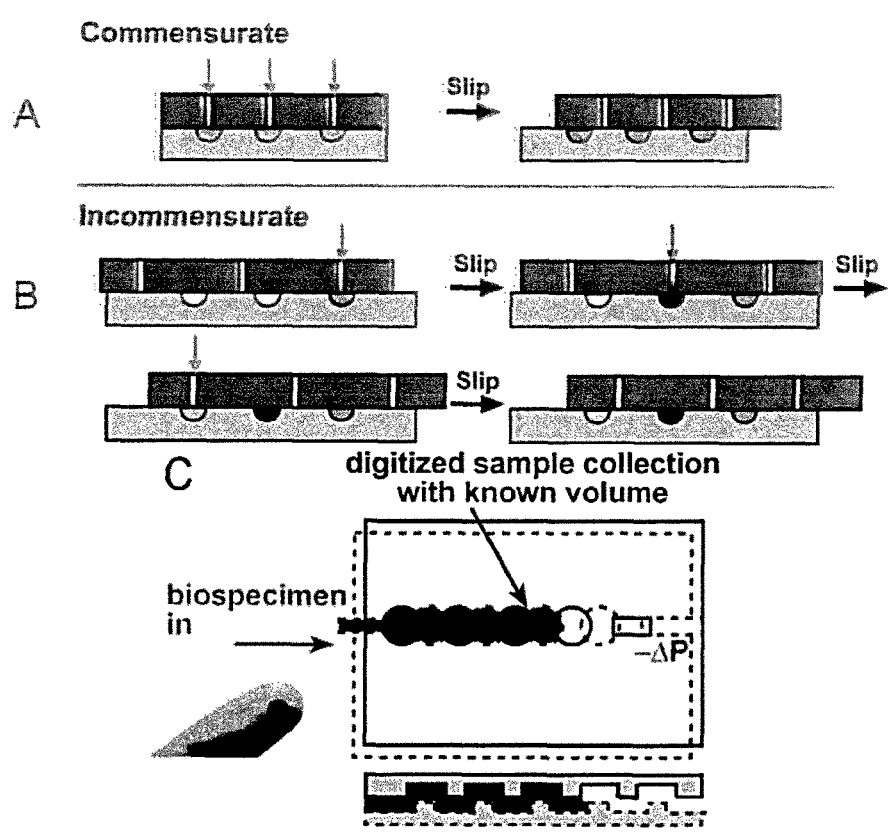
FIGS. 26A-26C provide exemplary schemes for sample collection via commensurate inlets (A), sample collection via incommensurate inlets (B), and digital quantification of sample volume (C). Additional schemes relating to sample collection are described in FIGS. 55A-55D, 56, and 57A-57B, as well as Example 15 herein.

The movement can be any useful relative movement. For instance, such movement can include axial rotation of two or more layers on the same axis or rotation of two or more layers on different axes. For example, the device can include three layers, each having a cylindrical, generally planar surface (e.g., layers 2501, 2502, and 2503 in FIG. 25). Relative movement of layer 2501 on axis 2505 results in axial translation of layer 2501 relative to layers 2502 and 2503. In another instance, such movement can include longitudinal translation between two or more layers. For example, the device can include three layers, each having a front face (e.g., left edge of layers 1410, 1420, and 1430 in FIG. 14) and a back face (e.g., right edge of layers 1410, 1420, and 1430 in FIG. 14). Relative movement of layer 1410 to the left results in longitudinal translation of layer 1410 relative to layers 1420 and 1430. In yet another instance, the movement can be a combination of axial rotation and longitudinal translation.

Accordingly, the relative movement may be linear; rotational, or a combination of both. In some instances, two-dimensional motion (e.g., X-Y motion) may be accomplished through a combination of linear and/or rotational movements. For example, sliding and rotating means may be employed to effect linear and rotational sliding motion. In addition, such means for producing relative sliding motion may be constructed from, for example, motors, levers, pulleys, gears, hydraulics, pneumatics, a combination thereof, or other electromechanical or mechanical means known to one of ordinary skill in the art. Other examples of methods of controlling the motion of one part relative to another include, but are not limited to, sliding guides, rack and pinion systems (U.S. Pat. No. 7,136,688), rotational plates (U.S. Pat. No. 7,003,104), slider assemblies (U.S. Pub. Nos. 2007-0155451 and 2008-0058039), guide grooves (U.S. Pat. Nos. 5,805,947 and 5,026,113), piezoelectric actuators (U.S. Pub. No. 2005-0009582), ball bearings and notches (U.S. Pat. No. 2,541,413), and drive cables (U.S. Pat. No. 5,114,208), each of which is incorporated herein by reference in its entirety. Moreover, motion of layers relative to one another may be constrained by notches, retainers, and/or a system of holes and mating pins, for example, as are typically used alone or in combination in electrical connectors. Also, the motion of the layers relative to one another may be constrained by a case, posts, grooves and ridges, gears, or, for example in the case of rotational motion, a central axis. In certain embodiments, the device is configured to be manipulated by a robot.

For any of the layers described herein, the distance between layers may vary depending on the type of substrate. In certain embodiments, the distance may vary in different device positions, for example due to design or surface roughness. Generally speaking, the gap may range anywhere from 0.2 nanometers to 20 micrometers. In particular embodiments, the gap between layers is filled with any useful lubricant, such as those described herein.

The structures within the device and/or layers can be designed to accommodate the relative movement to be exerted. For instance, when rotation movement is used to connect or disconnect the layers, then the structural elements (e.g., chambers or channels) within the layer can be arrayed in a radial or spiral pattern.

Relative movement can be effected by any useful assembly. Exemplary assemblies for rotation include a rotary joint mechanism, a rotational actuation mechanism (e.g., employing a pull string for rotational actuation), and a rotational shaft assembly. The rotational motion may be achieved by standard mechanisms, including motors, springs, e.g., clock springs, pull strings, bearings, cams, rotatable hubs, cable elements, gears, and/or actuators. These mechanisms can be designed to control the number, force, and/or speed of rotations. The device may be designed to be activated only once, or it may be used indefinitely. The device may include one or more switches to prevent actuation prior to use. Switches may be disposed on the surface of the device, cap, or lid to ensure proper contact between these structures.

Translation between layers may be guided by a guide/track configuration (see, e.g., FIGS. 41 and 48, as well as Example 9), or a ball bearing configured to slidingly engage the layers in order to limit the direction and amount of relative movement. In addition, the relative movement between the layers may be automated (e.g., using any useful mechanism, such as those described herein).

In one exemplary rotary joint mechanism, a rotatable layer is connected with a fixed layer. To achieve rotation, the rotatable layer can include an outer bearing (e.g., an outer ring bearing), and the fixed layer can include an inner bearing (e.g., an inner ring bearing), where these bearings allow for the outer bearing to rotate with respect to the inner bearing. Such bearing can include or be coupled to at least one motor (e.g., through a cable element, gear mechanism, etc.). Another exemplary assembly includes a stationary shaft interconnected to a base that is included in a fixed layer, and a rotatable layer that includes a hub rotatably interconnected to the stationary shaft. The hub can be supported in axial and radial directions by a bearing (e.g., oil- or air-filled bearing). The rotatable layer can include or be coupled to at least one motor (e.g., through a cable element, gear mechanism, etc.). The motor can be an actuator of any type, e.g., electrical motor, electroactive polymer, galvanometer actuator, hydraulic piston, microelectromechanical system (MEMS) actuator, piezoelectric actuator, relay, or stepper motor.

Autonomous Controller

Relative movement can be effected by any useful autonomous controller. The autonomous controller can include any mechanism or assembly described herein. An autonomous controller can be useful for controlling the operations of a SlipChip, a thin-film SlipChip, or another device. Various functions can be part of the design of the controller to provide a hands-off interface for untrained user. These include, but are not limited to (1) pumping, (2) slipping, and (3) timing control of the first two operations and any of the device's operations. For example, multi-step pumping and slipping can be programmed by using the timing control. These operations may also be performed, for example, without the need of an energy source stored in the SlipChip devices (such as, for example, a battery).

In particular embodiments, the autonomous controller allows for controlling one or more processes (e.g., any described herein) without user input. For instance, such control can be effected by turning on a switch, which activates the autonomous controller. In some embodiments, the controller includes one or more elements that allow for hand-held or portable use. For instance, any of the components herein (e.g., a power element; a regulating element; a timing element; a moving element; a transfer element; a switch; and/or a linkage) can be provided in a miniaturized format that uses minimal power or no external power source.

An autonomous controller may include a mechanical, pneumatic, fluidic, electromechanical, or electronic mechanism, or combinations thereof. A non-limiting exemplary controller includes a power element; a regulating element, which is optional and serves to maintains a relatively constant rate for the source of power; a timing element, which determines the rate of the relative movement of the device; a moving element, which promotes relative movement of the device; a transfer element, which transfers the force of the power source to the moving element and/or the timing element; and/or a switch, which is optional and serves to connect the power element either directly or indirectly to the moving element, where each of these elements can be interconnected either directly or indirectly (e.g., by a linkage, such as any described herein).

A power element may be any source of power, including mechanical, electrical, electromechanical, pneumatic, or fluidic sources, that drives relative movement. Examples of power elements include but are not limited to a winder, a spring (e.g., a mainspring, a spiral torsional spring, a semi-reverse torsional spring, or a reverse torsional spring), a hand crank, a rotor mechanism (e.g., having a rotating pendulum and a pinion movable by kinetic energy generated by movement of the user, where the pinion is coupled to a generator and energy is stored in a capacitor or battery), a photovoltaic cell, a battery, a solar cell, a generator (e.g., an electric generator, such as a dynamo, a magnetohydrodynamic generator, an induction generator, a homopolar generator, or an excited generator), an alternator, and/or a capacitor. The power element can interconnect directly with a moving element or indirectly with a moving element (e.g., through one or more transfer elements or linkages).

The power element can be connected to one or more optional regulating elements that maintains a relatively constant rate for the source of power. For example, in a mechanical power element, the regulating element can be selected from a pendulum, a balance wheel, a stackfreed (e.g., a spring-loaded cam mounted on an axle of the power element and including a spring-loaded roller), a cam, a ratchet, a fusee (e.g., a cone-shaped pulley system attached to the power element by a chain or another useful linkage), a stopwork, a remontoire (e.g., a secondary spring or weight that powers an escapement), a going barrel (e.g., a structure that contains the mechanical power element under tension and allows for use of the mechanical power element to provide constant torque), a motor barrel, or a pinion (e.g., a safety pinion that engages a barrel, such as a going barrel), as well as combinations thereof. For example, in an electrical power element, the regulating element can be selected from a connector, a coil, a fuse, a resistor, a transformer, a thermistor, a capacitor, and/or a diode.

In one non-limiting example, the assembly includes a spring as the power element and one or more regulating elements. In particular embodiments, the assembly includes a spring, an arbor that serves as an axle for the spring, a ratchet movably connected to the arbor to prevent unwinding of the spring, a going barrel having gear teeth and containing the spring, and a pinion (e.g. a center wheel pinion) movably connected to the gear teeth of the going barrel, where the gear is optionally connected directly or indirectly to a transfer element (e.g., a gear train, or any described herein).

The assembly can include a timing element that determines the rate of relative movement. The timing element can include a balance wheel (e.g., a weighted wheel including a spiral spring or balance spring), a pendulum, a tuning fork, a synchronous motor, a synchronized motor, a directly synchronized oscillating system, a stepping motor, an electro-mechanical stepping mechanism, or a crystal oscillator (e.g., a quartz oscillator). The timing element can be designed to effect particular reaction times (e.g., including time periods for sample incubation, reaction, preservation, storage, processing, or analysis). The timing element (e.g., a balance wheel or a pendulum) can optionally include an escapement mechanism, which transfers the force of the power source to the timing element, monitors the number of oscillations in the timing element, and connects to the moving element (e.g., through one or more linkages or one or more transfer elements) in order to effect relative movement commensurate with the oscillations of the timing element. Exemplary, non-limiting escapement mechanisms include, a verge escapement, an anchor escapement (e.g., a deadbeat escapement), a detached escapement (e.g., a detent escapement or a co-axial escapement), a cross-beat escapement, a cylinder escapement, a duplex escapement, a lever escapement, a grasshopper escapement, a gravity escapement, or an electromagnetic escapement (e.g., a switch or a phototube including an electromagnet coupled to the timing element), as well as any described herein. The timing element (e.g., a motor system or a crystal oscillator) can optionally include an oscillation monitor, an oscillation divider (e.g., a frequency divider connected to an output of a crystal oscillator), a storage circuit (e.g., a bistable multivibrator, which is connected to the output of the frequency divider), a switching circuit (e.g., connected to the output of the storage circuit), and/or an electronic balance wheel system (e.g., connected to the output of the switching circuit). Exemplary timing elements are provided in U.S. Pat. Nos. 344,922; 1,489,762; 4,036,006; 7,352,655; 8,308,346; and 8,263,883 each of which is incorporated herein in its entirety.

To achieve relative movement in the device, the assembly can include a moving element. The moving element can be connected directly or indirectly to the device or a portion thereof (e.g., one or more layers, such as through a central axle for rotational movement) using any useful linkage or transfer element (e.g., as described herein). Exemplary moving elements include one or more of a gear, a spring, a fly wheel, a pendulum, and/or a motor. In particular embodiment, the moving element is connected to the timing element to ensure that relative movement occurs at a particular rate. In a further embodiment, this connection between the moving element and the timing element is an escapement mechanism (e.g., any described herein).

To transfer power to the timing element and/or moving element, the assembly can include one or more transfer elements. Exemplary transfer elements include one or more of the following: a gear train (e.g., including one or more wheels and one or more pinions), a wheel, a pinion, a gear, a plate, a bar, a cam, a ratchet, a lever, an escapement, a cable, and/or a pulley.

The assembly can optionally include a switch, which controls the connection between the power element and the moving element. Exemplary switches include a toggle switch, a momentary switch, a rocker switch, a rotary switch, a biased switch (e.g., a push button switch), a float switch, a limit switch (or microswitch stimulated by rotary movement), a reed switch, a key switch, a control switch, a sail switch, a pressure switch, a tilt switch, a knife switch, an electronic switch (e.g., a relay, such as an analogue switch), a membrane switch, a piezo switch, or a touch switch (e.g., a capacitance touch switch, a resistance touch switch, or a piezo touch switch), as well as those described in U.S. Pat. Nos. 4,001,527; 4,021,626; 4,912,376; 5,160,853; 6,861,601; 7,251,142; 7,579,565; and 8,263,883, each of which is incorporated herein by reference in its entirety.

An exemplary mechanical mechanism may include a movable winder as a power element mechanically connected to a spring as a moving element; a gear train including an input gear, an output gear, and an intermediate gear; an escapement driven by the output gear; and a linkage coupled to the gear train for movement with this gear train. A non-limiting mechanism is provided in FIGS. 23-31 of U.S. Pat. No. 5,926,660, incorporated herein by reference in its entirety.

Another exemplary mechanical mechanism may include a knob (power element) fixed to a spring (movement element) through a rotatable shaft and a contact member moveable by the shaft (transfer element) to transfer the mechanical force of the spring to one or more layers of the device thereby effecting motion of these layers. A non-limiting mechanism is provided in U.S. Pat. No. 7,579,565, incorporated herein by reference in its entirety.

Another exemplary mechanism may include a winder (power element) fixed to a rotatable shaft bearing a spring (moving element). The shaft is interconnected with a transfer element consisting of a gear mechanism and a shaped cam, which can be interconnected with one or more movable layers via one or more cams or optionally cogged wheels. A non-limiting mechanism is provided in FIGS. 3-6 of U.S. Pat. No. 2,895,547, incorporated herein by reference in its entirety.

Another exemplary mechanism may include a flywheel (moving element) interconnected through gears and/or shaped cams (transfer element) to movable layers. The flywheel is capable of being set in motion by an external power element and consisting essentially of an element rotatably mounted and having members that are centrifugally movable and yieldably held in place against centrifugal movement. A non-limiting mechanism is provided in U.S. Pat. No. 1,926,276, incorporated herein by reference in its entirety.

Another exemplary mechanism may include an input for a fluid (power element), one or more reservoirs for storing this fluid, a timer valve, one or more time selector valves, and an output such as a piston (moving element) interconnected either directly or through a gear train or a pulley with movable layers. The input is connected through the timer valve to both the output and one or more selector valves. Each of the selector valves is then connected individually to a separate reservoir for storing fluid. The timer valve is engaged to switch the flow of fluid away from supplying the reservoirs to supplying the output upon reaching a threshold pressure within all reservoirs, to which time selector valves are open. A non-limiting example is provided in U.S. Pat. No. 6,070,610, incorporated herein by reference in its entirety.

Another exemplary mechanism includes an electric power element such as batteries, a moving element such as electric timer coupled to a motor, and a transfer element including at least a shaft of the motor to effect movement of movable layers. The electric timer includes a motor; at least one memory for storing a programmable schedule and one or more controller settings; a controller coupled to the memory for controlling the switching of power to the motor according to the programmable schedule; a user interface including a display and at least one button. The controller is programmed such that a user can program the programmable schedule and the one or more controller settings by interacting with at least one button. The controller has an operating mode and a setup mode that can be toggled between by interacting with at least one button. A non-limiting example is provided in U.S. Pat. No. 8,314,517, incorporated herein by reference in its entirety.

Figure 45:
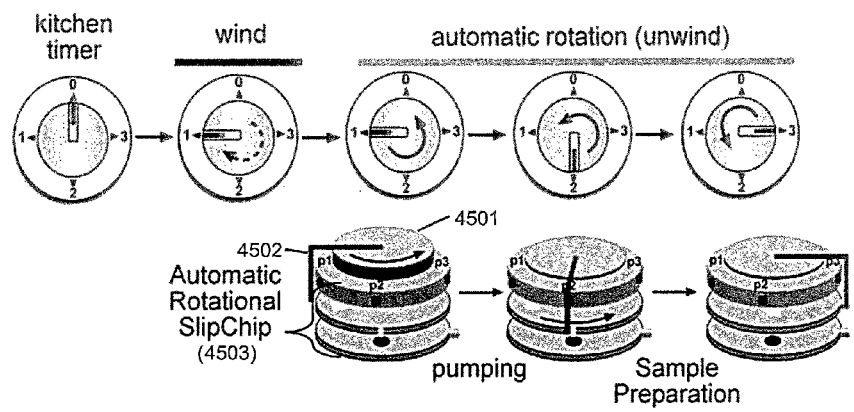
FIG. 45 provides an exemplary scheme for a single and simple winding maneuver to autonomously control the operation of a SlipChip 4503. The exemplary controller includes an unwinding structure 4501 and a rotating architecture 4502.

The energy source for various manipulations, which may include slipping, pumping, and timing control, may be created, for example, by using a standard mechanical structure that can store potential energy in its deformed state. In one non-limiting embodiment, the constant-force spring may be used to provide energy and a constant force for achieving autonomous operations. In some embodiments, a single and simple winding maneuver is the only required action that the end user needs to perform in order to initiate the operation of a SlipChip (similar to using a mechanical timer; see FIG. 45). In this embodiment, once the potential energy is stored in the deformed spring and the user initiates the controller, the stored potential energy will be released to form a mechanical force in a constant speed that controls the position of the architecture for driving the SlipChip to pump and slip (or relatively move the layers of a device) at a certain time point. FIG. 45 shows a non-limiting, exemplary scheme of one embodiment of this controller.

As illustrated in FIG. 45, in this embodiment, the continuous released potential energy rotates the unwinding structure 4501 in a constant speed. In some cases, a rotating architecture 4502 may be attached to this unwinding structure 4501 and follow the timed rotation movement. For example, while the rotating architecture 4502 is rotating along with the unwinding structure 4501, it may touch and then push the knobs connected to each SlipChip 4503 sequentially with a preprogrammed timing system (FIG. 45). In this instance, the mechanical force to complete each operation is provided by the unwinding force generated from the deformed springs. By using this concept, multiple operations, including pumping and slipping steps, can be achieved. Additional exemplary controller mechanism include any useful mechanical systems, such as those for controlling multiple valves or switches at a certain time point, and any described in U.S. Pat. Nos. 6,325,172; 6,354,172; 5,590,687; and 8,263,883, each of which is incorporated herein by reference.

In another embodiment, the design concept of autonomous controller is similar to the standard design of a mechanical timer. It may contain, for example, a main spring to provide the energy source, and a verge and an escape wheel (or similar design) to provide timing control (e.g., any described in Glasgow, David (1885). Watch and Clock Making. London: Cassel & Co.; Milham, Willis I. (1945). Time and Timekeepers. New York: MacMillan, ISBN 0-7808-0008-7; and Britten, Frederick J. (1881). The Watch and Clockmaker's Handbook, 4th Ed. London: W. Kent & Co., p. 56-58, each of which is incorporated herein by reference). To optimize total operation time of a SlipChip (e.g., from one minute to several minutes), the complicated gear train of a normal mechanical timing system can be minimized, if desired.

Figure 46:
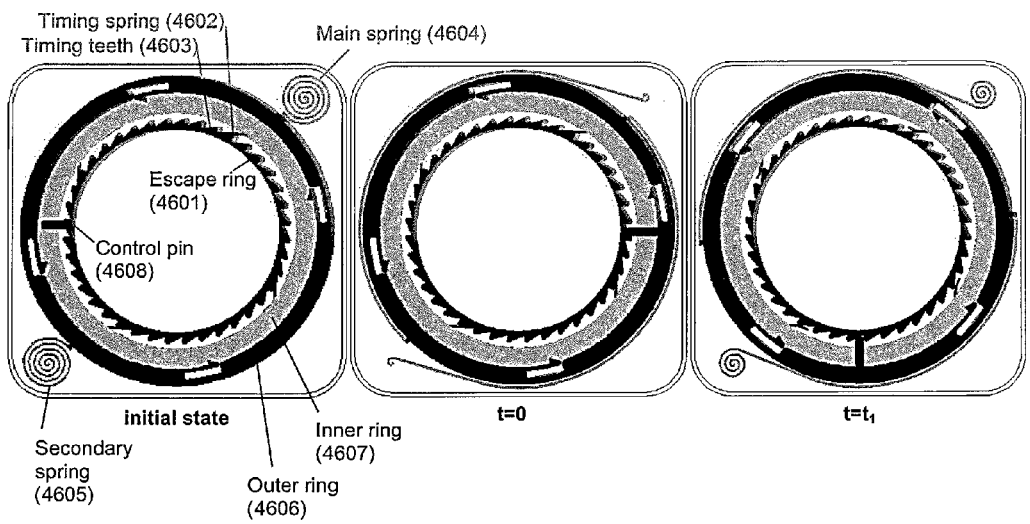
FIG. 46 provides an exemplary scheme for an autonomous controller of relative movement in a SlipChip. This non-limiting system includes an escape ring 4601, four timing springs 4602, timing teeth 4603, a main spring 4604, a secondary spring 4605, an outer ring 4606 and inner ring 4607 of a latch system, and a control pin 4608.

FIG. 46 illustrates one non-limiting example of an autonomous controller. In this embodiment, the timing system is achieved by three components on the controller. Here, it includes (1) at least one main spring made by a constant force spring, (2) at least one timing spring, and (3) an escape ring. In this case, the main spring 4604 is fixed on to the base of the controller and connected to one part of the latch system 4606. In this case, the latch system is designed in a way that the unwinding maneuver does not initiate or introduce uncontrolled operations to the SlipChip. In this embodiment, once it is unwound (t=0) and then released, it provides a constant winding force on the blue latch system while rotating the second part of the latch system at the same time (green ring, t=t$_1$). The timing control may, for example, be created by using timing springs (black bars 4602 attached to the inner ring 4607) and timing teeth 4603. In this particular case, while the latch system is rotating, the timing springs move against the designed topology of the timing teeth, and the escape ring is designed in a way that it introduces deformation to the timing spring. This mechanism creates a periodic resistant force against the winding force from the constant force spring. It can, for example, slow down the winding motion and create a timed rotation motion to the latch system. This timed rotation motion is one of various options for governing the timing of SlipChip operations. In this iteration, a control pin 4608 can be attached to the latch system and moved along with the latch system while initiating multiple pumping and slipping steps sequentially, as described in FIG. 45.

Figure 47:
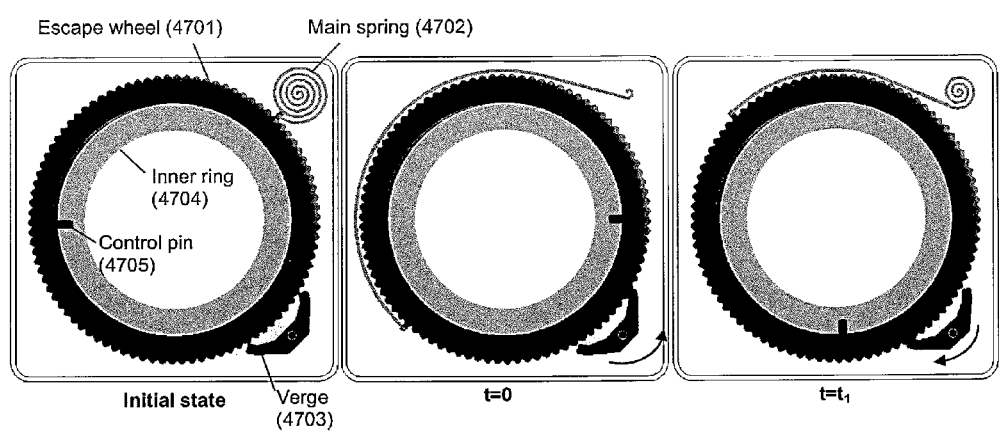
FIG. 47 provides another exemplary scheme for an autonomous controller of relative movement in a SlipChip. This non-limiting system includes an escape wheel 4701, a main spring 4702, a verge 4703, an inner ring 4704 of a latch system, and a control pin 4705.

FIG. 47 illustrates a second non-limiting example of an autonomous controller. This version contains three components: (1) the main spring (4702), (2) the escape wheel (4701), and (3) a verge (4703). Here, the inner ring 4704 holds the escape wheel in place. Similar to the runaway escapement design of a standard mechanical clocking system, the verge serves as a non-resonant oscillating mass and it interacts the rotation of the escape wheel (see FIG. 47, t=0 and t=t$_1$). As the main spring winds back to its original shape and rotates the escape wheel, the wedge may, for example, oscillate periodically to interfere with the rotations and slow down the rotation speed. Similar to FIG. 46, a control pin 4705 can be attached to the escape wheel and move along with the latch system while initiating multiple pumping and slipping steps sequentially as described in FIG. 45.

Figure 48:
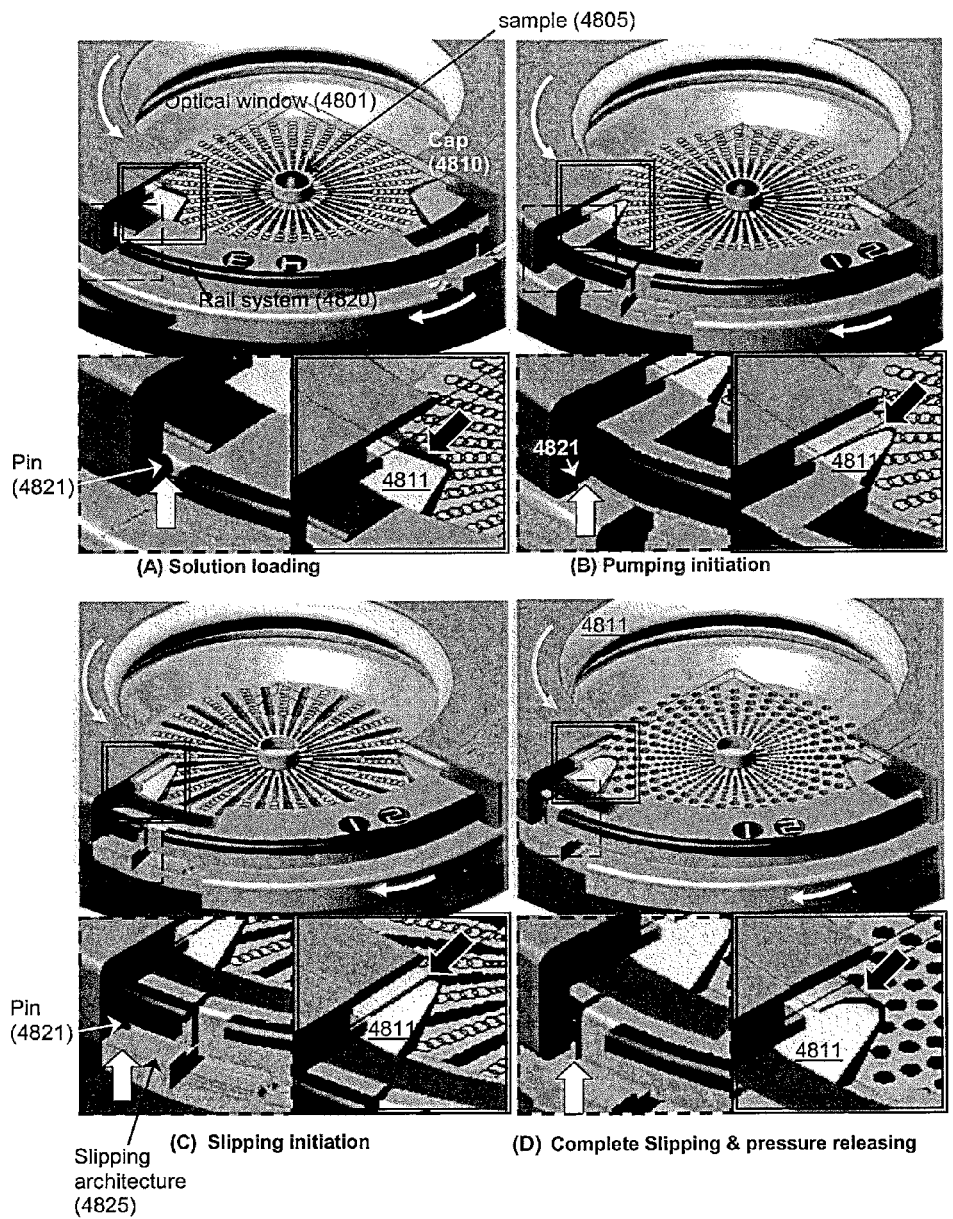
FIGS. 48A-48D provide yet another exemplary scheme for an autonomous controller of relative movement in a SlipChip. This non-limiting system includes an optical window 4801, the sample 4805, a cap 4810 having a flexible pumping cup 4811, and a rail system 4820 having a pin 4821 and a slipping architecture 4825. This system allows for (A) solution loading, (B) pumping initiation, (C) slipping initiation, and (D) complete slipping and pressure releasing.

In one non-limiting example, the control of various functions—including, but not limited to pumping and slipping—may be achieved by using a rail system. FIG. 48 describes the design of how one rail system can be used to perform functions including pumping, slipping, and pressure-releasing steps on a device (in this case, a thin-film SlipChip). Details of the dashed and double outlined boxes are provided below each figure in FIGS. 48A-48D. In this embodiment, the pumping method is based on creating a positive pressure in a sealed cavity above the device (here, a thin-film SlipChip). By using, for example, a timing control cap 4810 and a flexible pumping cup 4811 creating a sealed cavity, positive pressure can, for example, be created by pushing down the cap against the SlipChip. Negative pressure can also be created by the same approach. In FIG. 48, a quarter of the cap 4810, optical window 4801, and a pumping 4811 cup are cut out for ease of demonstration. In this embodiment, after loading the solution into the reagent reservoir at the center of the device (red droplet on SlipChip), the solution 4805 is secured by closing a cap to seal the cavity with the pumping cup (FIG. 48A). In one non-limiting embodiment, the cap is connected to the autonomous controller described in FIG. 46 or FIG. 47 when closing the cap. First, the user may, for example, turn the cap in order to store energy in the constant-force spring; then, the user may release the whole SlipChip assembly, and the constant-force spring recoils and operates the SlipChip device autonomously. In one non-limiting arrangement, the cap and the architecture holding the SlipChip are then automatically rotated against each other, thus initiating a series of sequential operations in the SlipChip device.

The series of sequential operations can be programmed in a variety of ways. In the non-limiting embodiment of FIG. 48, these operations can be programmed by using a pin 4821 (indicated by a white arrow in the inset images) against a rail system 4820 designed on the architecture holding the SlipChip. The following step below demonstrate one of several possible sequences for the loading procedure:

Step 1: Solution loading. In this embodiment, a positive pumping pressure is created by rotating the cap down along the rail (FIG. 48B, indicated by white arrows in large image). The cap compresses a flexible pumping cup 4811 (in inset image) and thus creates positive pressure to initiate loading (FIG. 48B, indicated by black arrow in inset image).

Step 2: Slipping. Once the solution is loaded into the SlipChip wells, in this embodiment, the rail system 4820 guides the pin 4821 to make contact with the slipping architecture 4825 (FIG. 48C, indicated by a white arrow in inset image) that can initiate slipping. By continuing to rotate the cap, one of the SlipChips may, for example, be slipped with a programmed angle to digitize the sample (FIG. 48D).

Step 3: Pressure releasing. As soon as digitization has been performed, the rail system can, for example, guide the cap to move up (FIG. 48D, indicated by a white arrow) and release the positive pressure (the pumping cup 4811 has restored to its original shape, indicated by black arrow in inset image), thus completing loading procedure.

Figure 53:
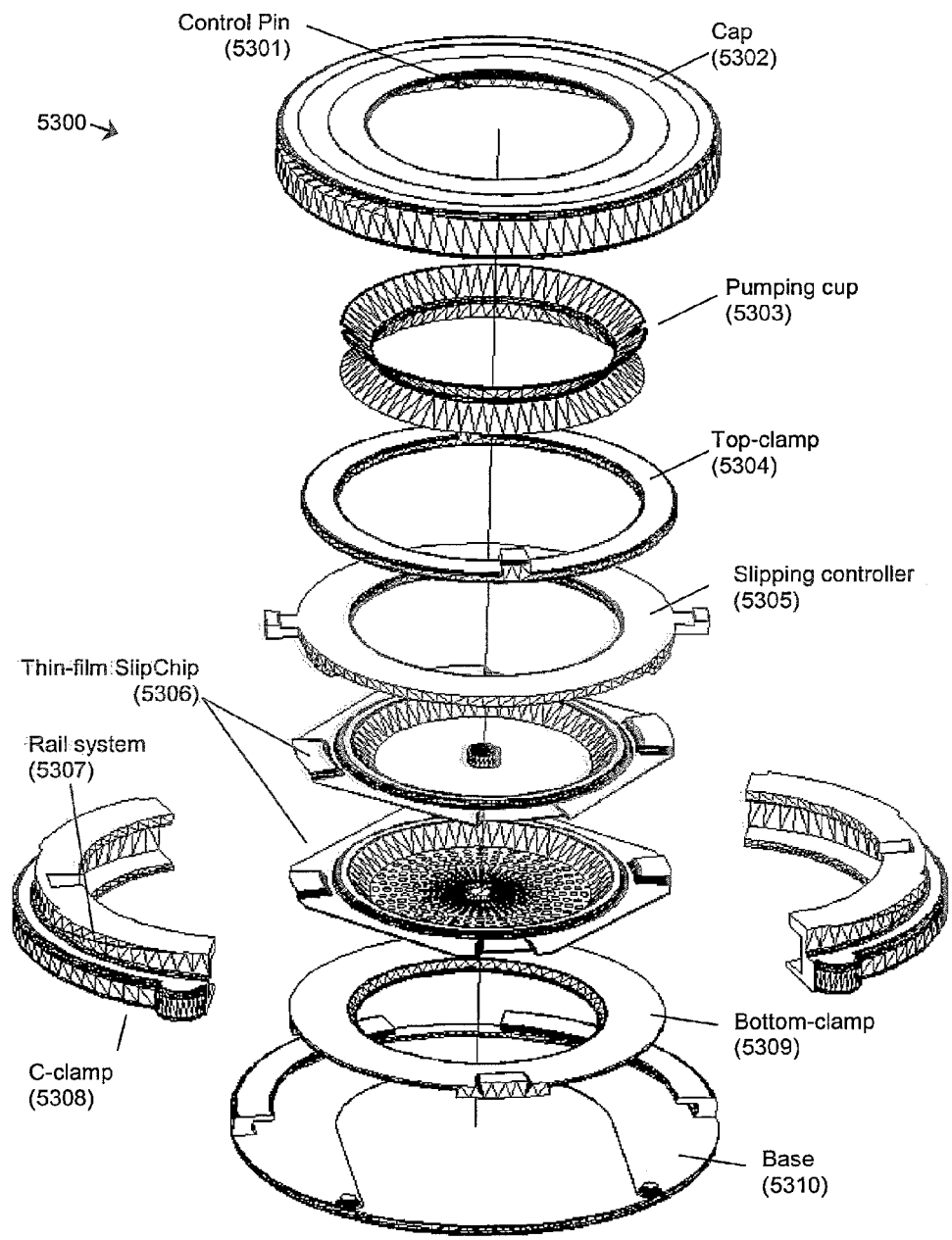
FIG. 53 provides an exemplary scheme for an autonomous controller of relative movement in a SlipChip. This non-limiting system 5300 includes a control pin 5301, a cap 5302, a pumping cup 5303, a top-clamp 5304, a slipping controller 5305, a thin-film SlipChip 5306, a rail system 5307, a C-clamp 5308, a bottom-clamp 5309, and a base 5310.

FIG. 53 provides the components of the autonomous controller system shown in FIG. 48. For clarity, the timing control components are not shown in FIG. 53. In this non-limiting embodiment, the system 5300 includes a base 5310 for holding the components, where at least two thin-film layers are sandwiched between the top-clamp 5304 and the bottom-clamp 5309. In this embodiment, the small gap between thin-film SlipChips is maintained by two C-clamps 5308 that provide a clamping force on to the top-clamp 5304 and the bottom-clamp 5309. A slipping controller 5305 is placed between the thin-film SlipChip 5306 and the top-clamp 5304. In this non-limiting embodiment, the slipping controller 5305 serves as the architecture for introducing slipping to the top layer, which can, for example, be slipped by a rotating pin attached to a mechanical timer as described in FIG. 46 or 47. The flexible pumping cup 5303 can, for example, be placed on top of the top-clamp 5304 and configured to contact the cap 5302 for creating a sealed cavity between the SlipChip 5306 and the cap 5302. A positive pressure can then be created by, for example, bringing the cap 5302 down and then loading a sample into the SlipChip 5306. In one non-limiting embodiment, the autonomous operation of the multiple steps described in FIG. 48 is achieved by allowing the control pin 5301 to rotate along the rail system 5307 designed on the C-clamp 5308. In a further non-limiting embodiment, a rotating movement is introduced by connecting the cap to a timing system, such as those described in FIG. 46 or 47.

Lubricant

The devices and methods can include any useful lubricant. In some embodiments, the lubricant facilitates movement of the first, second, and/or intermediate layers and/or minimizes contamination between the first, second, and/or intermediate layers or chambers within these layers.

In addition, the lubricant can be selected to be substantially inert with respect to the substances (e.g., reagents and/or samples) that will be in contact with and/or transported through the device. For instance, the lubricant can optionally be a fluid that is substantially immiscible with the reagent(s) and/or sample(s). The lubricant can optionally be selected to have physical characteristics that promote compartmentalization of the reagent(s) and/or sample(s). For instance, the layers and/or chambers can be fluorophilic, and the lubricant can be a fluorous liquid. In this example, compartmentalization occurs by competing surface characteristics, where surface tension results in separating reagent and/or sample fluids into separate plugs or droplets encapsulated by the lubricant.

Exemplary lubricants include a hydrocarbon, a fluorous substance, an ionic liquid, a non-Newtonian fluid, or a lubricating powder or bead. Exemplary hydrocarbons include alkanes, paraffin oils, hexane, hexadecane, silicon oil, greases (e.g., Dow Corning high vacuum grease, Fomblin vacuum grease, Krytox greases), mineral oil, and other organic materials or polymers, as well as mixtures thereof. Exemplary fluorous substances include fluorocarbons (including perfluorinated and semifluorinated alkanes, e.g., octadecafluoro-decahydronaphthalene and perfluorooctylethane), alkyl and aryl fluorocarbons, halofluorocarbons (e.g., perfluorooctyl bromide), fluorinated alcohols (e.g., 1-(1,2,2,3,3,4,4,5,5,6,6-undeca-fluorocyclohexyl)ethanol or $C_6F_{11}C_2H_4OH$), fluorinated oils, liquid fluoropolymers (e.g., perfluoropolyethers), Fluorinert (3M), Krytox oils, Fomblin oils, and Demnum oils.

Ionic liquids include a cation and an anion, which form a salt and are in a liquid state. Exemplary cations include choline; imidazolium-based cations, such as optionally substituted imidazolium-based cations (e.g., 1-$C_{1-10}$ alkyl-3-$C_{1-10}$ alkyl-imidazolium, (3-$C_{1-10}$ alkyl-imidazolium-1-yl)-$C_{1-10}$ alkanol, or 1-$C_{1-10}$ alkyl-2,3-di-$C_{1-10}$ alkyl-imidazolium, such as 1-$C_{1-10}$ alkyl-3-methyl-imidazolium, (3-methylimidazolium-1-yl)-$C_{1-10}$ alkanol, or 1-$C_{1-10}$ alkyl-2,3-dimethylimidazolium) or bicyclic imidazolium-based cations (e.g., optionally substituted 2,3-$(CH_2)_{2-6}$-imidazolium, such as 1-alkyl-2,3-trimethyleneimidazolium or 1-alkyl-2,3-tetramethyleneimidazolium); pyridinium-based cations, such as 1-$C_{1-10}$ alkyl-pyridinium; pyrrolidinium-based cations, such as 1-$R_1$-1-$R_2$-pyrrolidinium, where each of $R_1$ and $R_2$ is independently $C_{1-10}$ alkyl; ammonium-based cations, such as $NR_1R_2R_3R_4$, where each of $R_1$, $R_2$, $R_3$, and $R_4$ is independently $C_{1-10}$ alkyl; and phosphonium-based cations, such as $PR_1R_2R_3R_4$, where each of $R_1$, $R_2$, $R_3$, and $R_4$ is independently $C_{1-10}$ alkyl. Exemplary anions (e.g., such as X for any ionic liquid described herein) include a halogen (e.g., fluoride, bromide, chloride, or iodide); a phosphate anion (e.g., hexafluorophosphate [$PF_6$], dihydrogen phosphate [dhp], or tris(pentafluoroethyl)trifluorophosphate [FAP]); a borate anion (e.g., tetracyanoborate [TCB], tetrafluoroborate [$BF_4$], or bis(oxalato)borate [BOB]); a sulfonylimide anion $N(SO_2C_nF_{2n+1})(SO_2C_mF_{2m+1})$, where each of n and m is, independently, an integer between 1 to 10, and optionally n=m, such as bis(trifluoromethanesulfonyl)imide ($N(SO_2CF_3)_2$ or [TFSI]) or bis(perfluoroethanesulfonyl)imide ($N(SO_2C_2F_5)_2$; [BETI] or [PFSI]); a sulfonate anion (e.g., triflate [$SO_3CF_3$], mesylate [$SO_3CH_3$], or tosylate [$SO_3C_6H_4CH_3$]); an alkylsulfate anion (e.g., $C_{1-10}$ alkyl-$OSO_3$); a cyanimide anion (e.g., [$(CN)_2N$]); or a carboxylate anion (e.g., formate, acetate, lactate, oxalate, citrate, malate, glycolate, or saccharinate).

Exemplary ionic liquids include choline ionic liquids (e.g., choline dihydrogen phosphate (choline dhp) or choline saccharinate); 1-alkyl-3-methylimidazolium [R-mim] ionic liquids (e.g., such as 1-alkyl-3-methylimidazolium anion [R-mim][X] ionic liquids, including 1,3-dimethylimidazolium iodide, 1-ethyl-3-methylimidazolium bromide, 1-propyl-3-methylimidazolium bromide, 1-propyl-3-methylimidazolium chloride, 1-propyl-3-methylimidazolium bis(trifluoromethanesulfonyl)imide, 1-propyl-3-methylimidazolium bis(perfluoroethanesulfonyl)imide, 1-butyl-3-methylimidazolium bromide, 1-butyl-3-methylimidazolium chloride, 1-butyl-3-methylimidazolium bis(trifluoromethanesulfonyl)imide, 1-butyl-3-methylimidazolium bis(perfluoroethanesulfonyl)imide, 1-pentyl-3-methylimidazolium bromide, 1-hexyl-3-methylimidazolium bromide, 1-heptyl-3-methylimidazolium bromide, 1-octyl-3-methylimidazolium bromide, or 1-nonyl-3-methylimidazolium bromide); (3-methylimidazolium-1-yl)alkanol [ROH-mim] ionic liquids (e.g., such as (3-methylimidazolium-1-yl)alkanol anion [ROH-mim][X] ionic liquids, including 3-(3-methylimidazol-3-ium-1-yl)propan-1-ol bromide, 3-(3-methylimidazol-3-ium-1-yl)propan-1-ol chloride, 4-(3-methylimidazol-3-ium-1-yl)butan-1-ol bromide, 5-(3-methylimidazol-3-ium-1-yl)pentan-1-ol bromide, or 6-(3-methylimidazol-3-ium-1-yl)hexan-1-ol bromide); 1-alkyl-2, 3-dimethylimidazolium [R-dmim] ionic liquids (e.g., such as 1-alkyl-2,3-dimethylimidazolium anion [R-dmim][X] ionic liquids, including 1,2,3-trimethylimidazolium iodide, 1-ethyl-2,3-dimethylimidazolium bromide, 1-propyl-2,3-dimethylimidazolium bromide, 1-butyl-2,3-dimethylimidazolium bromide, 1-pentyl-2,3-dimethylimidazolium bromide, 1-hexyl-2,3-dimethylimidazolium bromide, 1-heptyl-2,3-dimethylimidazolium bromide, 1-octyl-2,3-dimethylimidazolium bromide, or 1-nonyl-2,3-dimethylimidazolium bromide); 1-alkyl-2,3-trimethyleneimidazolium [R-3C-im] ionic liquids (e.g., such as 1-alkyl-2,3-trimethyleneimidazolium anion [R-3C-im][X] ionic liquids, including 1-methyl-2,3-trimethyleneimidazolium iodide, 1-ethyl-2,3-dimethyleneimidazolium bromide, 1-propyl-2,3-dimethyleneimidazolium bromide, 1-butyl-2,3-dimethyleneimidazolium bromide, 1-pentyl-2,3-dimethyleneimidazolium bromide, or 1-hexyl-2,3-dimethyleneimidazolium bromide); 1-alkyl-2,3-tetramethyleneimidazolium [R-4C-im] ionic liquids (e.g., such as 1-alkyl-2,3-tetramethyleneimidazolium anion [R-4C-im][X] ionic liquids, including 1-methyl-2,3-tetramethyleneimidazolium iodide, 1-ethyl-2,3-tetramethyleneimidazolium bromide, 1-propyl-2,3-tetramethyleneimidazolium bromide, 1-butyl-2,3-tetramethyleneimidazolium bromide, 1-pentyl-2,3-tetramethyleneimidazolium bromide, or 1-hexyl-2,3-tetramethyleneimidazolium bromide); and 1-butyl-3-methylimidazolium [Bmim] ionic liquids (e.g., such as 1-butyl-3-methylimidazolium anion [Bmim][X] ionic liquids, including 1-butyl-3-methylimidazolium hexafluorophosphate (Bmim $PF_6$) or 1-butyl 3-methylimidazolium lactate (Bmim lactate)).

In particular embodiments, the following ionic liquids can be used in combination with a nucleic acid (e.g., DNA and/or RNA): 1-alkyl-3-methylimidazolium [R-mim] ionic liquids (e.g., such as [R-mim][X] ionic liquids or any described herein); (3-methylimidazolium-1-yl)alkanol [ROH-mim] ionic liquids (e.g., such as [ROH-mim][X] ionic liquids or any described herein); 1-alkyl-2,3-dimethylimidazolium [R-dmim] ionic liquids (e.g., such as [R-dmim][X] ionic liquids or any described herein); [R-3C-im] ionic liquids (e.g., such as [R-3C-im][X] ionic liquids or any described herein); [R-4C-im] ionic liquids (e.g., such as [R-4C-im][X] ionic liquids or any described herein); or [Bmim] ionic liquids (e.g., [Bmim][X] ionic liquids or any described herein). Further ionic liquid are described in Shi et al., Chem. Commun. 48:5325-5327 (2012), Wang et al., Anal. Chem. 79:620-625 (2007), and Fukaya et al., AE1—Fourteenth International Symposium on Molten Salts Joint International Meeting, Oct. 3-Oct. 8, 2004, "Evaluation of a series of imidazolium based ionic liquids as solvents for nucleic acids," Abstract 2437, each of which is incorporated herein by reference in its entirety.

Exemplary non-Newtonian fluids include shear-thickening fluids, gels, including hydrogels, and carbohydrate-rich or lipid-rich phases, including lipid cubic phase and other lipid mesophases. In some embodiments, permeability to gases may be desirable, for example in some applications that use live cells and tissues inside the device. Exemplary lubricating powders or beads include various Teflon® beads or powders (e.g., composed of PTFE (poly(1,1,2,2-tetrafluoroethylene), PFA (perfluoroalkoxy copolymer resin), or FEP (fluorinated ethylene propylene resin)), graphite, molybdenum disulfide, or tungsten disulfide. Any of these lubricants can optionally include one or more surfactants, for example to cause or prevent surface aggregation and/or to influence the stability of substances.

Immiscible Fluid

The devices and methods can include any useful immiscible fluid. In some embodiments, the immiscible fluid facilitates compartmentalization of one or more substances (e.g., a sample, a reagent, or any other useful substance, as described herein) in one or more first, second, and/or intermediate layers or chambers within these layers. In other embodiments, the immiscible fluid facilitates flow through one or more capture regions (e.g., as described herein).

An immiscible fluid is a fluid (e.g., a gas or a liquid) that is immiscible with one or more of the second fluids at certain ranges of temperature, pressure, and composition useful for storing, preserving, processing, or analyzing the sample. In some embodiments, the second fluid is an aqueous solution, a sample for storage, preservation, processing, or analysis, and/or a reagent for storing, preserving, processing, or analyzing the sample. In other embodiments, the fluid is immiscible with water or an aqueous solution.

Miscibility can be tested with any useful method under useful conditions for temperature, pressure, and composition. Generally, these useful conditions will be similar to those useful for sample storage, preservation, processing, or analysis. Useful temperature and pressure conditions include those for maintaining stability of the desired sample to be tested and/or the reagent(s) for use with this sample (e.g., a temperature of from about −80° C. to about 150° C., as well as any ranges therein, and a pressure generally of about 1 atm), as well as those for conducting the storage, preservation, processing, or analysis methods described herein. For instance, when the sample is a human blood sample, this sample should be maintained at or below the physiological temperature of about 37° C. Thus, useful immiscible fluids can be tested at a range of from about −80° C. to about 40° C. Further, if the human blood sample includes one or more nucleic acids that require additional analysis (e.g., by PCR requiring thermocycling at increased temperature of >90° C.), then useful immiscible fluids can be tested at a range from about −80° C. to about 100° C. Useful compositions include various ratios of the fluid to be tested for immiscibility in a mixture with a test sample, reagent, or substance, such as ratios to be used within the device for sample storage, preservation, processing, or analysis.

Methods for testing miscibility include, but are not limited to, light scattering, X-ray scattering, and/or neutron scattering to determine whether a single phase is present in a mixture (indicating miscibility) or multiple phases are present in a mixture (indicating immiscibility).

Exemplary immiscible fluids include ionic fluids, aqueous-aqueous immiscible fluids, oils, fluorocarbons, etc., as well as any lubricant described herein.

The immiscible fluid can be used as a component of any fluid, solution, or buffer described herein. For instance, the immiscible fluid can be included in one or more of a lubricant, a washing buffer, and/or an elution buffer. In some embodiments, the elution buffer (e.g., as described herein, such as for sample preparation) includes one or more immiscible fluids. For example, the immiscible fluid can be used to elute small volumes (e.g., about 750 μL, 500 μL, 250 μL, 100 μL, 50 μL, 10 μL, 5 μL, 1 μL, 750 nL, 500 nL, 250 nL, 100 nL, 50 nL, 10 nL, 5 nL, 1 nL, 750 pL, 500 pL, 250 pL, 100 pL, 50 pL, 10 pL, 5 pL, 1 pL, 750 fL, 500 fL, 250 fL, 100 fL, 50 fL, 10 fL, 5 fL, 1 fL, 750 aL, 500 aL, 250 aL, 100 aL, 50 aL, 10 aL, 5 aL, or 1 aL, including any ranges for these values, as described herein) from a chamber or a capture region. In one non-limiting embodiment, the elution buffer including one or more immiscible fluids (e.g., one or more ionic fluids, such as any described herein) removes water from the substance passing through the capture region.

For example, the method includes filling or adding an elution buffer (e.g. including one or more immiscible fluids, such as an ionic liquid) to one or more capture regions, thereby removing and/or capturing an eluent (e.g., water, a target, an analyte, a nucleic acid, a sample, an impurity, etc.) with the elution buffer (e.g., immiscible fluid). In yet other non-limiting embodiments, the elution buffer including one or more immiscible fluids (e.g., one or more ionic fluids, such as any described herein) extracts an analyte (e.g., a nucleic acid, a target, a protein, an impurity, or any useful component of a sample).

Moving Substances within Devices

The devices of the invention can include the use of one or more forces or gradients to move one or more substances within the device. A pressure gradient can be created by any component described herein, such as the capping system described herein. The devices herein can optionally include posts or other three-dimensional structures that partially or completely block a chamber and/or channel. For example, a post member is provided in a first layer, which blocks a chamber in a second layer upon moving the first layer relative to the second layer. In this manner, positive pressure may be generated in front of the post member and negative pressure may be generated behind. It may be used to load, dispose, or move a substance within the device. Flow may also be generated by the pressure gradient created by the relative movement.

Exemplary, non-limiting forces and gradients include use of centrifugal force; a surface tension gradient; osmotic pressure; capillary pressure, such as by including arrays of channels and/or chambers to create gradients of capillary pressure; positive or negative pressure that can be generated externally, for example by using pumps or syringes; slipping, such as by relative movement of one or more layers; pressure generated by compressing or expanding a chamber containing a fluid; an electric force; an electroosmotic force; gravity; a magnetic force; or a chemical reaction or process (e.g., by using reagents to produce a gaseous product, thereby generating pressure, such as the combination of sulfuric acid with a carbonate salt or the combination of sodium bicarbonate with a solid acid, for example tartaric acid, activated by addition of water; or by using reagents that consume gas, thereby causing a decrease in pressure, such as the combination of sodium hydroxide with carbon dioxide), which may be initiated externally or initiated by relative movement (e.g., by slipping). Further methods and devices for filling or loading fluids are described herein.

Capture Regions

The devices of the invention can include one or more capture regions. The capture region can include any useful material to capture one or more targets or analytes (e.g., a nucleic acid or any described herein).

The capture region can include any useful material for capturing one or more analytes. Exemplary materials includes a filter, a matrix, a polymer, a charge switch material, a gel, and a membrane (e.g., a silica membrane, a glass-fiber membrane, a cellulose membrane, a nitrocellulose membrane, a polysulfone membrane, a nylon membrane, a polyvinylidene difluoride membrane, a vinyl copolymer membrane, or an ion exchange membrane, including any described herein), a fiber (e.g., a glass fiber), or a particle (e.g., a silica particle, a bead, an affinity resin, or an ion exchange resin).

The capture region can include any useful dimension. In particular embodiments, the capture region has one or more dimensions that are less than about 1,000 μm.

In some embodiments, the capture region includes a charge switch material having an ionizable group that changes charge based on ambient conditions. Such charge switch materials can be useful for ion exchange procedures to capture a target (e.g., a negatively charged target, such as a nucleic acid) with a charge switch material having positive charge at low pH (e.g., a pH<6.0 or 6.5 or a pH lower than or equal to the pKa of the ionizable group). Then, the target can be eluted by releasing it from the charge switch material, such as by elution at a raised pH (e.g., a pH≥8.5 or a pH higher than the pKa of the ionizable group). Exemplary charge switch materials include those with an ionizable group selected from a biological buffer (e.g., -2-acetamido-2-aminoethanesulfonic acid (ACES); N-2-acetamido-2-iminodiacetic acid (ADA); amino methyl propanediol (AMP); 3-1,1-dimethyl-2-hydroxyethylamino-2-hydroxy propanesulfonic acid (AMPSO); N,N-bis2-hydroxyethyl-2-aminoethanesulfonic acid (BES); N,N-bis-2-hydroxyethylglycine (BICINE); bis-2-hydroxyethyliminotrishydroxymethylmethane (Bis-Tris); 1,3-bistrishydroxymethylmethylaminopropane (Bis-Tris Propane); 4-cyclohexylamino-1-butane sulfonic acid (CABS); 3-cyclohexylamino-1-propane sulfonic acid (CAPS); 3-cyclohexylamino-2-hydroxy-1-propane sulfonic acid (CAPSO); 2-N-cyclohexylaminoethanesulfonic acid (CHES); 3-N,N-bis-2-hydroxyethylamino-2-hydroxypropanesulfonic acid (DIPSO); -2-hydroxyethylpiperazine-N-3-propanesulfonic acid (EPPS); -2-hydroxyethylpiperazine-N-4-butanesulfonic acid (HEPBS); -2-hydroxyethylpiperazine-N-2-ethanesulfonic acid (HEPES); -2-hydroxyethylpiperazine-N-2-propanesulfonic acid (HEPPSO); 2-N-morpholinoethanesulfonic acid (MES); 4-N-morpholinobutanesulfonic acid (MOBS); 3-N-morpholinopropanesulfonic acid (MOPS); 3-N-morpholino-2-hydroxypropanesulfonic acid (MOPSO); piperazine-N-N-bis-2-ethanesulfonic acid (PIPES); piperazine-N-N-bis-2-hydroxypropanesulfonic acid (POPSO); N-trishydroxymethyl-methyl-4-aminobutanesulfonic acid (TABS); N-trishydroxymethyl-methyl-3-aminopropanesulfonic acid (TAPS); 3-N-trishydroxymethyl-methylamino-2-hydroxypropanesulfonic acid (TAPSO); N-trishydroxymethyl-methyl-2-aminoethanesulfonic acid (TES); N-trishydroxymethylmethylglycine (TRICINE); trishydroxymethylaminomethane (Tris); polyhydroxylated imidazoles; triethanolamine dimers and polymers; and di/tri/oligo amino acids, for example Gly-Gly, Ser-Ser, Gly-Gly-Gly, and Ser-Gly), a polyhydroxylated amine (e.g., TRIS or Bis-Tris), imidazole, histidine, and polyhistidine. In some embodiments, the charge switch material can include Bis-Tris, a Bis-Tris polymer (e.g., formed by attachment of Bis-Tris monomers to a polyacrylic acid (PAA) backbone), PAA, or a combination of Bis-Tris and PAA (e.g., where both Bis-Tris and PAA are in polymeric form and can formed as a co-polymer or as layers including alternating Bis-Tris and PAA layers). In other embodiments, the charge switch material is a weakly basic polymer that has a cationic charge at acidic pH but has a neutral charge at basic pH. Such materials include poly[N-(3-imidazolylpropyl)methacrylamide hydrochloride-co-acrylamide], poly[N-(3-imidazolylpropyl)methacrylamide hydrochloride-co-2-hydroxyethyl methacrylate], poly(1-vinylimidazole), poly(2-aminoethyl methacrylate hydrochloride-co-2-hydroxyethyl methacrylate), poly(1-vinylimidazole-co-2-hydroxyethyl methacrylate), poly[N-(1,1-dimethyl-3-imidazolylpropyl) acrylamide], or poly(N-2-methyl-1-vinylimidazole. Additional charge switch materials include those that are pH-insensitive but targets charge changes. Further charge switch materials are described in U.S. Pat. Nos. 5,582,988, 6,914,137 and 7,319,004, each of which is incorporated herein by reference.

Such materials and procedures are commercially available, such as in ChargeSwitch® Technology (available in numerous formats from Invitrogen Corp. or Life Technologies™ Corp., Carlsbad, Calif., such as in a ChargeSwitch® coated membrane, magnetic bead, or well plate). Further charge switch materials and/or ion exchange processes are described in U.S. Pat. Nos. 5,234,809, 6,718,742, 6,914,137, and 7,319,004; U.S. Pub. Nos. 2003/0008320, 2005/0053941, 2003/0054395, 2003/0173284, 2003/0130499, 2005/0053941, 2006/0154247, 2006/0263780, 2007/0122809, 2006/0024712, 2012/0196944, and 2012/0197009; and Int. Pub. Nos. WO 02/48164, WO 99/29703, WO 01/88185, WO 01/03149, WO 03/101494, WO 03/046177, WO 2005/012521, and WO 2006/004611, each of which is incorporated by reference in its entirety.

The charge switch material can be combined with any useful format. In some instances, the charge switch material is combined with a magnetic particle (e.g., having a diameter between 20 µm and 1 mm) formed from any useful material (e.g., formed from magnetite, iron oxides, transition metal oxides, ferromagnetic materials, or paramagnetic materials). Exemplary charge switch materials include polymethacrylate carboxy ion-exchangers, silica particles coated with a negative charge, cellulose or agarose with phosphate or sulfate groups, or any negatively charged species. Exemplary magnetic particles are described in U.S. Pat. No. 6,718,742, which is incorporated herein by reference.

Furthermore, the capture region can include any useful substance for capturing one or more analytes. Exemplary substances include one or more of inhibitors, osmolytes, trehalose, oligosaccharides (sucrose, maltose, etc.), N-oxides, liposaccharides, alcohols (e.g., ethanol or isopropanol for precipitation), a chaotropic substance (e.g., guanidinium salt such as guanidinium (iso)thiocyanate, guanidinium thiocyanate, or guanidinium HCl, sodium iodide (NaI), sodium perchlorate ($NaClO_4$), potassium iodide, potassium bromide, sodium thiocyanate, or urea), an organic reagent, an antibody including fragments thereof, a protein (e.g., bovine serum albumin, ovalbumin, β-lactoglobulin, α-lactalbumin, myoglobin, lactoferrin, ribonuclease A, or cytochrome C), a hydrophobic or hydrophilic surface, a ligand (e.g., biotin, or any other useful ligand), etc. The capture regions can include any useful combinations of substances (e.g., any described herein), such as the combination of a chaotropic substance with one or more particles (e.g., any described herein, such as silica particles, glass particles, or diatoms).

Samples and Reagents

The devices and methods of the invention can be used with any useful sample and/or reagent. In particular, a device can be pre-loaded with any useful reagent (e.g., a desiccant, a matrix, or any described herein), or the device can be provided as part of a kit including the device and one or more useful reagents.

Samples can be obtained from a subject (e.g., human subject), a food sample (e.g., including an organism), or an environmental sample (e.g., including one or more organisms). Exemplary, non-limiting samples include blood, plasma, serum, sputum, urine, fecal matter (e.g., stool sample), swab, sweat, spinal fluid, amniotic fluid, interstitial fluid, tear fluid, bone marrow, tissue sample (e.g., a skin sample or a biopsy sample), a buccal mouthwash sample, an aerosol (e.g., produced by coughing), nucleic acid, cell (e.g., tumor cells, fetal cells in blood, stem cells, bacterial and fungal cells, T-cells, or B-cells), protein, enzyme, soil, water, compost pile, manure pile, sediment (e.g., marine or freshwater sediment), a water sample, an air sample, rock, a plant sample, a food sample, or a gut sample. The sample can include any useful target or analyte to be detected, filtered, concentrated, and/or processed.

Any analyte of interest can be present in the sample. Such analyte: could be processed, captured, preserved, and/or removed for further analysis, treatment, reaction, and/or detection. Exemplary analytes include those described herein, such as those present in a test sample (e.g., any described herein), as well as one or more of the following: a protein (e.g., one or more antibodies such as Epstein-Barr virus (EBV) antibodies, hepatitis antigen/antibodies (e.g., hepatitis A, B, or C), or HIV antibodies, C-reactive protein (CRP), apolipoprotein (e.g., A-I or B), IGFBP-2, IGFB-3, transferrin receptor, lipoprotein (e.g., (a), B/A-1, or β), thyroglobulin, or hemoglobin (e.g., including glycosylated hemoglobin or HbA1c)), a nucleic acid (e.g., RNA or DNA), a cell (e.g., CD4+ lymphocyte), a virus (e.g., a whole virus, including HIV, CMV, hepatitis C virus, hepatitis B virus, hepatitis A virus, or herpes simplex virus), a parasite (e.g., *Toxoplasma gondii, Plasmodium falciparum, Trypanosoma cruzi, Giardia lamblia, Leishmania* spp, *Echinococcus granulosus, Schistosoma haematobium*, or *Brugia malayi*), a bacteria (e.g., *Mycobacterium leprae, Helicobacter pylori, Brucella* sp, or *Treponema pallidum*), a cytokine (e.g., IL-1, IL-1b, IL-2, IL-6, IL-7, IL-10, IL-13, IL-17, IFN, IFNg, TNF, or TNF-beta), an antibody (e.g., any herein), a hormone (e.g., estradiol, progesterone, prolactin, cortisol, dehydroepiandrosterone (DHEA, including its sulfate ester, DHEA-S), follicle-stimulating hormone (FSH), thyrotropin (TSH), thyroxine (T4), triiodothyronine (T3), luteinizing hormone (LH), insulin, leptin, sex hormone binding globulin (SHBG), somatomedin-C (IGF-1), testosterone, or androstenedione), an amino acid (e.g., arginine, histidine/urocanic acid, homocysteine, phenylalanine/tyrosine, and/or tryptophan), a drug (including candidate drugs or investigational new drugs for clinical trials), a small molecule (e.g., a peptide or peptoid, folate, or glucose), a contaminant (e.g., Hg, $H_2S$, sulfur oxides, etc.), a gas or vapor (e.g., oxygen, CO, $CO_2$, or any described herein), a volatile component (e.g., a volatile organic compound), an enzyme (e.g., a proteinase, an amylase, a protease, a glucanase, a lipase, a lactase, an amyloglucosidease, a glucoamylase, a protease, an isomerase, a cellulase, a ligninase, a xylanase, a catalase, a polymerase, trypsin, prostate-specific antigen (PSA), iduronidase, acid α-glucocerebrosidase (ABG), acid α-galactosidase A (GLA), lysosomal acid α-glucosidase (GAA), galactocerebroside α-galactosidase (GALC), or acid sphingomyelinase (ASM)), a sterol (e.g., cholesterol (e.g., including total cholesterol or high-density lipoprotein cholesterol (HDL)), or triglycerides).

Such analytes can be preserved (e.g., using any device herein, such as those having one or more membranes and/or bridges), analyzed (e.g., using any device herein, such as those having one or more capture regions), or preserved and analyzed (e.g., using any device herein, such as those having one or more membranes, bridges, and/or capture regions).

The device can be pre-loaded prior to use or subsequently loaded during use with any useful reagents. These reagents could also be included in any feature of the device, such as one or more chambers, layers (including portions thereof, such as, e.g., the portion of the layer lacking one or more chambers), capture regions, bridges, and/or membranes. Furthermore, such reagents can be used in gas, liquid, or solid form, as well as in a coating on the one or more features or in a coating on one or more solid supports (e.g., beads, particles, etc.) within one or more features, where such features include, e.g., one or more chambers, layers (including portions thereof, such as, e.g., the portion of the layer lacking one or more chambers), capture regions, bridges, and/or membranes.

Exemplary reagents include a desiccant (e.g., any described herein), a matrix (e.g., a stabilization matrix, such as any described herein), an organic or inorganic chemical, a compound, a mixture, a solution, an emulsion, a dispersion, a suspension, a molecule, an ion, a dimer, a macromolecule such as a polymer or protein, a nucleic acid, a biomolecule, an oligosaccharide (e.g., trehalose, sucrose, or maltose), an anticoagulant (e.g., heparin, EDTA, citrate, or oxalate), an inhibitor (e.g., to inhibit growth of one or more bacteria and/or other organisms, such as a chelator (e.g., any described herein), an antibiotic, a fluorinated polymer, PEG, albumin, a biocompatible coating (e.g., PDMS), an antifouling agent (e.g., tributyltin), or a biocide), a precipitate, a crystal, a chemical moiety or group, a particle, a nanoparticle, a reaction product, a solvent, a buffer (e.g., a washing buffer (e.g., Tris/EDTA; 70% ethanol; STET (Saline/Tris/EDTA/Triton* X-100 Solution); saline-sodium citrate (SSC) buffer; SSPE (0.2 M phosphate buffer, pH approx. 7.4, containing 2.98 M NaCl, and 0.02 M EDTA); FTA purification reagent, and the like) or an elution buffer (e.g., TRIS/EDTA; TRIS/acetate/EDTA, for example 4 mM Tris-acetate (pH 7.8), 0.1 mM EDTA, and 50 mM NaCl; TRIS/borate; TRIS/borate/EDTA; potassium phosphate/DMSO/glycerol; NaCl/TRIS/EDTA; NaCl/TRIS/EDTA/TWEEN; TRIS/NaCl/TWEEN; phosphate buffers; TRIS buffers; HEPES buffers; nucleic acid amplification buffers; or nucleic acid hybridization buffers)), a lysis agent (e.g., an enzyme (e.g., a lysosyme, trypsin, proteinase K, or other proteases), a detergent (e.g., Triton X-100 (polyethylene, glycol p-(1,1,3,3-tetramethylbutyl)-phenyl ether) or sodium dodecyl sulfate), or a chaotropic substance, such as any described herein), a chelating agent (e.g., diethylenetriaminepentaacetic acid (DTPA), ethylenediaminetetraacetic acid (EDTA), ethylene glycol tetraacetic acid (EGTA), trans-1,2-diaminocyclohexane-N,N,N',N'-tetraacetic acid (CDTA), 1,2-bis(2-aminophenoxy)ethane-N,N,N',N'-tetraacetic acid (BAPTA), 1,4,7,10-tetraazacyclododecane-1,4,7,10-tetraacetic acid (DOTA), N-(2-hydroxyethyl)ethylenediamine-N,N',N'-triacetic acid, or nitrilotriacetic acid (NTA)), a reducing agent (e.g., 2-mercaptoethanol, thiosulfate, TCEP (tris-(2-carboxyethyl)phosphine), dithiothreitol, or dithioerythritol), a dye, a stabilizer, a marker, a salt (e.g., a urate salt), a surfactant (e.g., an anionic surfactant, such as sodium dodecyl sulfate, or a cationic surfactant), a base (e.g., a weak base, such as trishydroxymethyl methane), a fluorophore, or a fluid, any one of which may exist in the solid, liquid, or gaseous state. Further, any of these reagents can be combined with any other useful structure or solid support described herein, such as a filter, a membrane, or a particle, or any described for a capture region. In addition, one or more reagents can be combined in any useful manner.

In particular, one or more desiccants can be useful when storing, preserving, treating, and/or preparing a sample. Exemplary desiccants include anhydrous calcium sulfate (gypsum, such as Drierite® (particle size (mesh) from 4, 6, 8, 10-20, or 20-40)), aluminas (such as activated aluminas, e.g., aluminum oxide or $Al_2O_3$), glass, silicas (e.g., $SiO_2$ (e.g., size-fractionated $SiO_2$ particles, such as those having a diameter of about 2 μm to about 10 μm), silica gel, Ascarite II® absorbents (e.g., carbon dioxide adsorbents including sodium hydroxide-coated silica), or diatomaceous silicas (e.g., Celite®, Celatom®, CAFA (Celite® Analytical Filter Aid))), a hygroscopic polymer and/or salt (e.g., including but not limited to $CaCl_2$, CaO, $ZnCl_2$, KOH, NaOH, $CaH_2$, $CaSO_4$, and $Na_2SO_4$), molecular sieves (or crystalline metal aluminosilicates, e.g., 3A, 4A, 5A, or 13X types in powder or bead forms), activated carbon (e.g., lignite carbon in granular or powder forms), montmorillonites (e.g., ($Al_2O_3.4SiO_2.xH_2O$)), or drying agents (e.g., barium oxide, boron oxide, calcium salts (e.g., calcium chloride or calcium hydride), copper(II) sulfate, lithium aluminum hydride, magnesium oxide, magnesium perchlorate, magnesium sulfate, phosphorus pentoxide, potassium hydroxide, sodium, sodium hydroxide, or sodium-potassium alloy (e.g., 22% sodium or 44% sodium)).

Sample Preservation

The devices of the invention can be useful for performing sample (e.g., biospecimen) preservation, such as by sample storage and stabilization in the liquid state or dry state, including molecular (e.g. proteins, nucleic acids) and cellular and multiple biospecimens (e.g., biological fluids and human biological fluids such as blood and plasma). Devices may include optional collection and/or optional sample preparation capabilities. In general, the devices allow for loading a sample, optionally combining the sample with a matrix, storing the resultant sample in the liquid or dry state for a desired time, and then recovering the sample. The matrix (e.g., stabilization matrix) can be liquid or solid, which can optionally be pre-loaded in the device, mixed with the sample prior to loading, or loaded in the device at the same time as the sample or at a different time.

Currently, there are two major ways to handle biological samples that need to be transported for analysis or stored and archived for long term use: freezing and drying (lyophilization is the combination of the two). The disadvantages of freezing and lyophilization are energy consumption, inaccessibility for resource-limited areas, and subject to failure if there is a power outage.

Drying and storing biological samples on a SlipChip, e.g., blood samples, can provide several advantages. Such advantages may include drying within minutes without any outside power supply; being ready to transport after samples are collected after a single relative movement (e.g., by slipping); integration of sample collection, drying, storage, and analysis on a single device; and/or application of microfluidic features (e.g., as in a microfluidic device) to provide miniaturized, fast, digital, and high throughput analysis.

Drying can be performed in the device in any number of ways. In one instance, a highly active and high-capacity desiccant can be preloaded into the device. The device is sealed (e.g., by any useful method, such as those described herein by closing a valve) to prevent the desiccant from absorbing ambient moisture before the sample is loaded. The sample chamber can be optionally pre-coated with a preservative matrix to avoid degradation of the sample during drying and storage. For example, a 10 μL sample can be digitized or partitioned into hundreds of aliquots to make rapid drying and digital analysis both possible.

The matrices described herein (e.g., stabilization matrices) can allow for liquid sample preservation or dry sample preservation at room temperature. Exemplary matrices can be liquid or dry and are available from suppliers including but not limited to Biomatrica, IntegenX/Genvault, Qiagen, and General Electric. Exemplary commercially available stabilization matrices include Biomatrica, DNAstable®/DNAstable® LD, DNAstable® Blood, DNAgard® Blood, DNAgard® Saliva, DNAgard® Tissue, RNAstable®, RNAgard®, Clonestable®, IntegenX/Genvault, GenTegra DNA, GenTegra RNA, GenPlate, Luna Innovations, Qiagen, All-protect Tissue Reagent, RNAlater® RNA Stabilization Reagent, GE Healthcare/Whatman plc, and FTA paper. Additional matrices include those having a desiccant (e.g., any described herein), a weak base, a chelating agent, an anionic surfactant or detergent, a uric acid, a salt (e.g., a urate salt, either alone or added to a cellulose based matrix (filter paper) to inactivate nuclease; or a sulfate salt, such as ammonium sulfate, ammonium bisulfate, cesium sulfate, cadmium sulfate, cesium iron (II) sulfate, chromium (III) sulfate, cobalt (II) sulfate, copper (II) sulfate, lithium sulfate, magnesium sulfate, manganese sulfate, potassium sulfate, sodium sulfate, or zinc sulfate), and/or an oligosaccharide (e.g., trehalose, sucrose, maltose, etc. to stabilize DNA, RNA, or protein for anhydrobiosis, lyophilization, vitrification, and/or room temperature air drying). In particular embodiments, the matrix includes a sulfate salt (e.g., an ammonium sulfate, including a final salt concentration in solution is between 10 g/100 ml and a saturating concentration (e.g., 100 g/100 mL)), an optional chelator (e.g., EDTA), a buffer (e.g., having a pH between 4 and 8), or a precipitant (e.g., ethanol, methanol, acetone, trichloroacetic acid, 1-propanol, 2-propanol, polyethylene glycol, or acetic acid). In other embodiments, the matrix includes (i) 1-methyl-3-carboxyethyl-imidazolium bromide, 1-hexyl-3-methylimidazolium bromide, 1-decyl-3-methylimidazolium bromide, 1-(2-hydroxyethyl)-3-methylimidazolium bromide, or 1-benzyl-3-hexylimidazolium bromide; and (ii) one or more of a precipitating agent (e.g., 5-(4-dimethyl)amino benzylidene rhodanine, sulfosalicylic acid, lithium chloride, or lithium hydroxide), a lower alcohol (e.g., methanol, ethanol, n-propanol, isopropanol, n-butanol, or isobutanol (2-methylpropan-1-ol)), or a chaotropic substance (e.g., any described herein). Such matrices can also include an optional chelating agent (e.g., any described herein), an optional reducing agent (e.g., any described herein), an optional pH buffer (e.g., any described herein), and optionally water. In some embodiments, the matrix includes (i) a borate composition (e.g., boric acid, boric anhydride, dihydrogen borate, hydrogen borate, diborate, triborate, tetraborate, metaborate, hydroxoborate (borax), borate salt, boric acid-glycerol, or boric-acid-1,3 propanediol) and (b) at least one stabilizer (e.g., hydroxyectoine, ectoine, homoectoine, betaine, L-carnitine, sarcosine, N,N-dimethylglycine, triethylammonium acetate, glycerol phosphate, N-(2-hydroxy-1,1-bis(hydroxymethyl)ethyl)glycine (tricine), 3-(N-morpholino)-2-hydroxypropanesulfonic acid (MOPSO), pentaerythritol, N-ethyl-N,N-bis-(2-hydroxyethyl)ammonium-N-4-butyl sulfonate, glycolic acid, lactic acid, malic acid, tartaric acid, 2-hydroxybutyric acid, 3-hydroxybutyric acid, 4-amino-3-hydroxybutyric acid, pyridine 2,5-dicarboxylic acid, 3-(1-azoniabicyclo[2.2.2]oct-1-yl)propane-1-sulfonate, 1-(2-carboxylatoethyl)-1-azabicyclo[2.2.2]octan-1-ium, or 4-[benzyl(2-hydroxyethyl)methylazaniumyl] butane-1-sulfonate). In yet other embodiments, the matrix includes (i) a liquid or dry material (e.g., polyvinyl alcohol) and (ii) a stabilizer (e.g., any described herein, including a trehalase stabilizer, a glycosidase inhibitor, a trehalase inhibitor (e.g., suidatrestin, validamycin A, validoxylamine A, MDL 26537, trehazolin, salbostatin, or casuarine-6-O-alpha-D-glucopyranoside), a chitinase inhibitor, an alpha-glucosidase inhibitor, a glycogen phosphorylase inhibitor, a neuraminidase inhibitor, a ceramide glucosyltransferase inhibitor, a beta-fructofuranosidase inhibitor (e.g. alpha-methyl glucoside, cellobiose, D-fructose, D-glucose, fructose, galactose, glucose, lactose, maltose, melezitose, melibiose, sucrose, trehalose, or turanose), or a lysosomal glycosidase inhibitor. In other embodiments, the matrix includes (i) a liquid or dry material (e.g., polyvinyl alcohol) and (ii) a stabilizer (e.g., any described herein, including a combination of trehalose and a trehalase inhibitor, such as any described herein). Further matrices are provided in U.S. Pat. No. 6,528,641 or U.S. Pat. No. 5,256,571, as well as U.S. Pub. Nos. 2005-0276728, 2006-0099567, 2008-0176209, 2008-0268514, 2011-0081363, and 2012-0052572, each of which is incorporated by reference in its entirety.

A sample, either before or after processing or analysis, as well as any substance described herein (e.g., a reagent, a buffer, etc.) can be preserved or stored either in the dry state or in the liquid state. In some instances, the sample is a liquid sample, and preservation in the liquid state may be preferable. In other instances, the sample is a liquid sample intended for long term storage (e.g., more than six months) and/or for storage at high temperatures (e.g., more than about 4° C.), and preservation in the dry state may be preferable. In yet other instances, the sample is a dried liquid sample (e.g., a dried blood spot, such as for DNA analysis, clinical testing, or any analysis described herein).

Liquid sample storage and preservation can be performed using a SlipChip device. A liquid sample (such as blood, saliva, urine, blood plasma, serum, purified protein or nucleic acid solution, cell culture medium, environmental sample etc., or any other described herein) can be loaded in the device. Dry preservation and storage can be performed by adding an extra drying step. Drying the sample can be done with several strategies, such as by using a device including desiccant and a bridge, a device including desiccant and a porous membrane, a device including a first module having a porous material and a second module having a desiccant, or a device including a module including a porous material that allows for drying under ambient conditions. Such devices are described herein and allow for a drying strategy that is not dependent on external ambient conditions (such as humidity). The desiccant can be any useful desiccant, e.g., described herein. Furthermore, the drying process can result from water transport occurring through a gas (e.g., air), a liquid (e.g., an immiscible fluid, such as a lubricant or oil), or a solid (e.g., a porous membrane, which can include but are not limited to Gore-Tex, and porous membranes made of PE, PP, PTFE, PES, PC (commercially available from Millipore and Whatman/General Electrics), as well as any described herein).

In particular embodiments, the timescales for preserving (e.g., in the dry state or in the liquid state) the sample (e.g., aliquots of such samples) and for loading the sample can be controlled. In some embodiments, these two processes can run simultaneously. For instance, the device can be loaded in parallel or in series. The matrices can be preloaded in the device or pre-mixed with the sample. Loading and drying can be achieved simultaneously, in which volume can be controlled by controlling the rate of filling and/or the rate of evaporation. Such an approach can allow for storing sample volumes that are larger than the actual volume of the chambers, if the timescales of loading and drying are comparable.

Various strategies can be implemented for preserving (e.g., in the dry state or in the liquid state) samples. In one example, vapor contact can be achieved through shallow empty bridges connecting the sample and the desiccant chambers (see, e.g., FIG. 1). In this strategy, the sample to be preserved is digitized in a large number of chambers (e.g., volumes on the order of 10-100 nL). During drying, each sample chamber is connected to another chamber containing a desiccant (e.g., a solid desiccant salt) through a duct ("bridge"). In particular embodiments, the bridge is shallow enough to allow vapor diffusion, while preventing any physical contact between the liquid(s) and/or content(s) of the two chambers.

In one embodiment, the device includes a desiccant and a bridge (FIG. 1). To implement this drying strategy, a "dry-chip configuration" can be applied, in which the lubricant is a very viscous material (e.g., a viscosity>>10,000 cst) present in the gap between the layers. Examples of these materials include but are not limited to silicone greases, fluorinated greases (such as DuPont Krytox), high molecular weight polymers (PDMS, etc), and partially cured elastomers. The sample can be loaded in the sample chambers by any useful method, such as any described herein. Vapor contact is reversible and can be initiated by relative movement (e.g., by slipping). Direct contact between the sample and the desiccant is prevented by using a shallow bridge, and the liquid is confined in the sample chamber by surface tension. The desiccant can be pre-loaded before assembling the device. In case the desiccant is a liquid, it can also be loaded after assembling the device. Alternatively, the devices can be produced using different bridge-like strategies, such as pneumatic valves. Preliminary tests showed that this configuration is suitable for drying solutions stored in 10 nL chambers in less than 10 minutes. Another relative movement (e.g., by slipping) brings the dehydrated sample in contact with a chamber that has been injected with water in order to re-hydrate it at the desired time (see, e.g., FIG. 1E). Further details concerning rehydration are provided herein.

Figure 2:
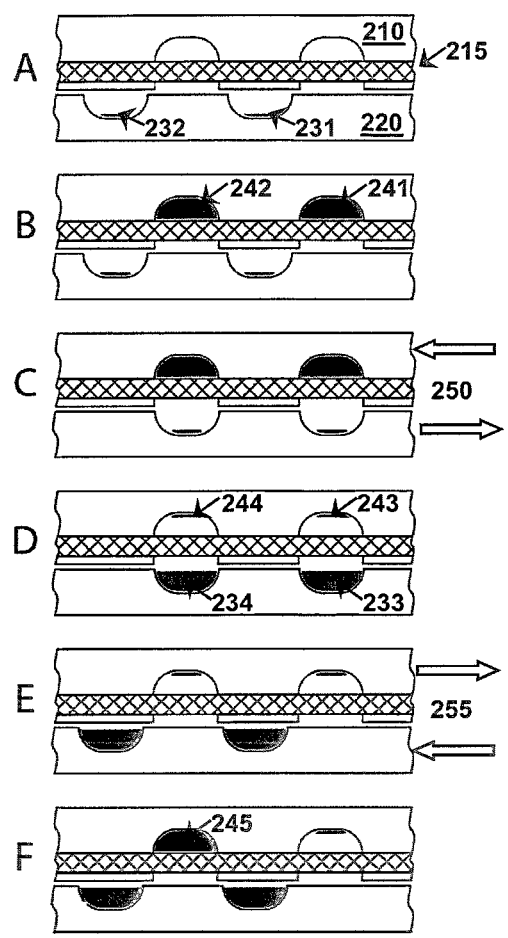
FIGS. 2A-2F provide exemplary schemes for preserving a specimen using a membrane in a device of the invention. A: In the loading position, the top layer 210 contains sample chambers and a porous material 215 (mesh filling). The bottom layer 220 contains desiccant chambers preloaded with desiccant 231 and 232. The sample and desiccant chambers are not aligned, and vapor contact is minimized in this position. B: Samples 241 and 242 are loaded in the top layer. C: Relative movement (block arrows 250) brings the device to the drying position. This creates vapor contact between the sample chambers and the desiccant chambers, thereby initiating preservation. D: Preserving is complete when the desiccant has absorbed or adsorbed the solvent (e.g., water) from the sample, as evidenced by the presence of hydrated desiccant 233 and 234 and preserved (e.g., in dry or liquid state) or concentrated residual substances 243 and 244 in the sample chambers. E: Relative movement (block arrows 255) brings the device to the recovery position, thereby suppressing vapor contact. F: Water or any useful solvent (e.g., a buffer) can be injected to provide a rehydrated sample 245. Further, rehydration can be performed on an array of sample chambers, or just a subset of such chambers.

In another embodiment, the device includes a porous membrane and a desiccant (FIG. 2). In this approach, the SlipChip device includes at least one chamber for sample drying ("sample chamber") and at least one of the chambers includes a hydrophobic porous material, such as a polymeric membrane. The device also includes at least one chamber containing desiccant ("desiccant chamber"). A sample can be injected in the device using any useful loading strategy, e.g., any described herein. Vapor contact is reversible and can be initiated by relative movement (e.g., by slipping). The desiccant can be pre-loaded before assembling the device.

Figure 3:
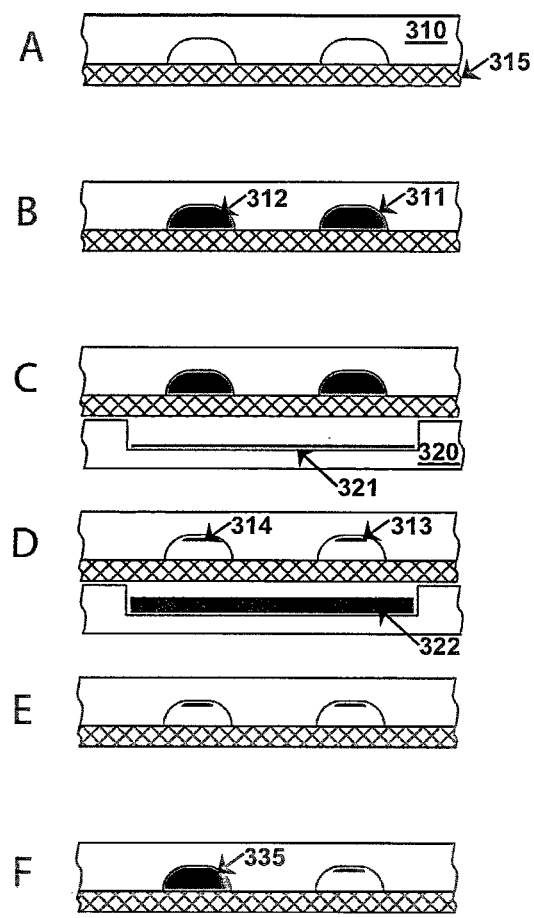
FIGS. 3A-3F provide exemplary schemes for preserving a specimen using a sample module and a drying module. A.

In yet another embodiment, the device includes a first module including a porous material and a second module containing a desiccant (FIG. 3). In this approach, a module ("storage module") includes at least one chamber for sample drying ("sample chamber") and at least one of the chambers includes a hydrophobic porous material, such as a polymeric membrane. After loading the sample, the storage module can be combined with a second module ("drying module") that includes at least one chamber containing a desiccant. Combining the two results in fluidic communication (e.g., vapor contact) between the desiccant and the sample chamber, thereby initiating drying.

Figure 4:
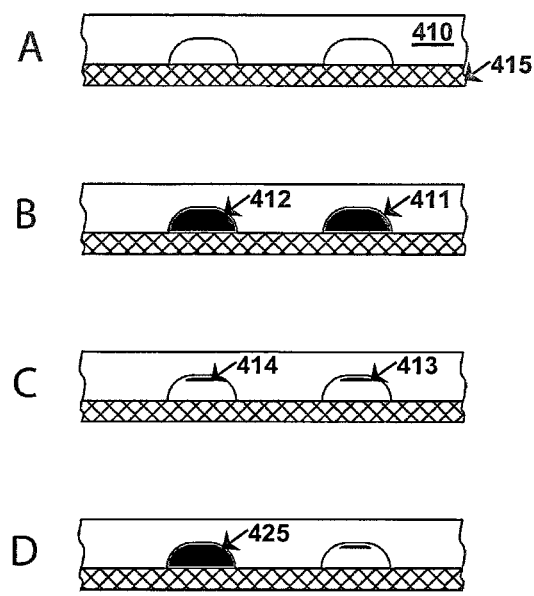
FIGS. 4A-4D provide exemplary schemes for preserving a specimen using a storage module. A: The exemplary storage module includes sample chambers in the top layer 410 and a porous material 415 (mesh filling). B: Samples 411 and 412 are loaded into the chambers. The storage module is then exposed to an external atmosphere, thereby initiating preservation. C: Preserving is complete when desiccant has absorbed or adsorbed the solvent (e.g., water) from the sample, and preserved (e.g., in dry or liquid state) or concentrated residual substances 413 and 414 are present in the sample chambers. Alternatively, preserving is completed when all the solvent (e.g., water) evaporates from the sample and diffuses in the atmosphere, even if no desiccant is present. D: Water or any useful solvent (e.g., a buffer) can be injected to provide a rehydrated sample 425. Rehydration can be performed on an array of sample chambers, or just a subset of such chambers.

In another embodiment, the device includes a module including a porous material, which allows for drying under ambient conditions (FIG. 4). In this approach, a module ("storage module") includes at least one chamber for sample drying ("sample well") and at least one of the chambers include a hydrophobic porous material, such as a polymeric membrane. After loading, drying is achieved automatically by exposing the module to an external atmosphere, such as ambient atmosphere or a controlled environment (such as drying cabinet, laminar flow hood, or a closed container containing desiccant).

Figure 5:
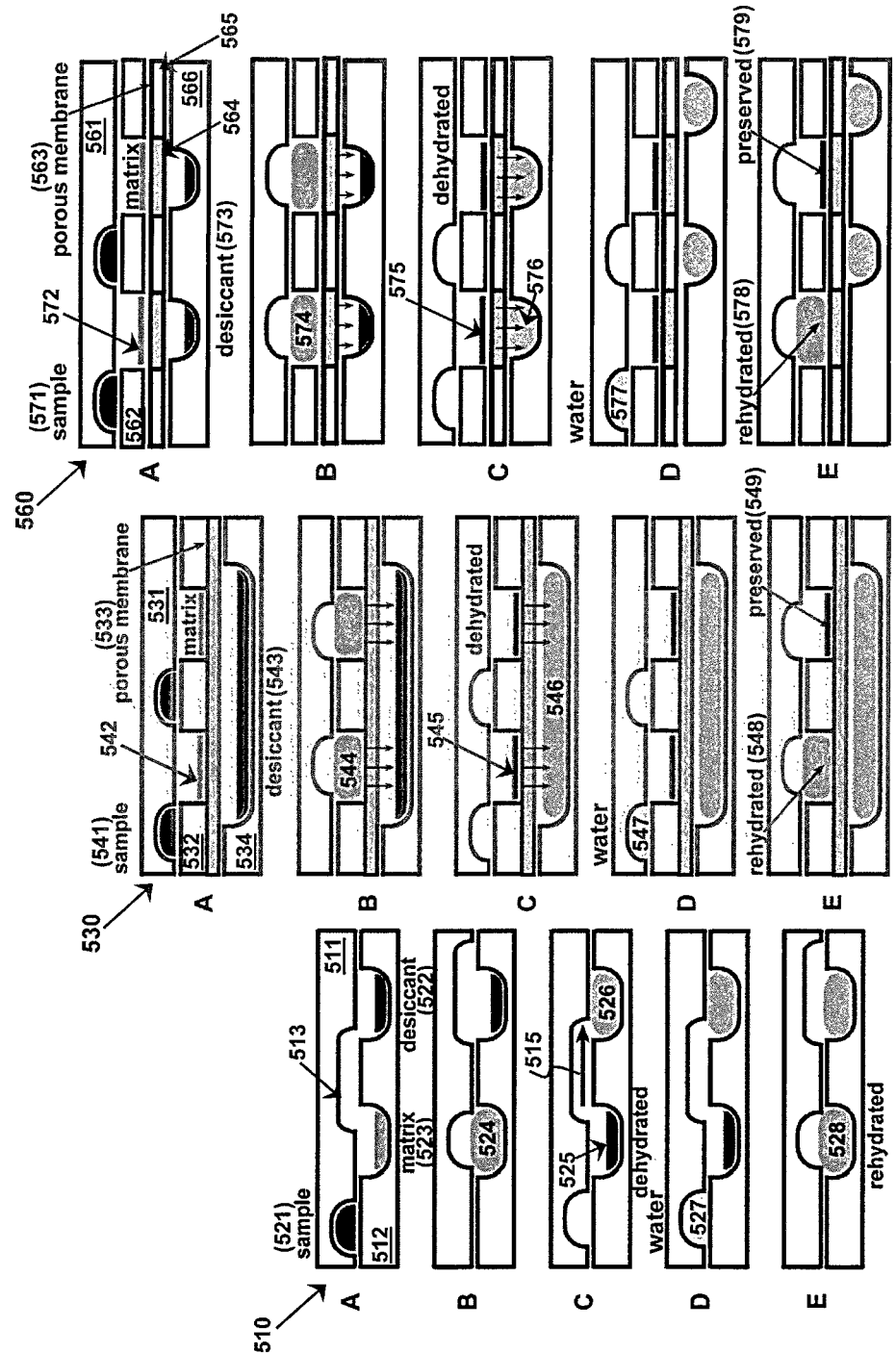
FIG. 5 provides exemplary schemes for sample preservation using devices having various structures, including a bridge (left), a porous membrane (center), or a patterned porous membrane (right). The following A-E describe the device on the left 510. A: The device 510 includes a top layer 511 having a chamber for a sample 521, a bottom layer 512 having chambers for a desiccant 522 and a matrix 523, and a bridge 513. B: Relative movement of the top layer results in a sample combined with the matrix 524. C: Another relative movement of the top layer creates fluidic communication (e.g., vapor contact shown by arrow 515) between the combined sample 524 and the desiccant, thereby initiating preservation. Preservation is complete when the desiccant has absorbed or adsorbed the solvent (e.g., water) from the sample, as evidenced by the presence of hydrated desiccant 526 and a preserved (e.g., in dry or liquid state) or concentrated residual substance 525 in the sample chamber. D and E: Water 527 or any useful solvent (e.g., a buffer) can be injected to provide a rehydrated sample 528. The following A-E describe the device in the center 530. A: The device 530 includes a top layer 531 having chambers for a sample 541, an intermediate layer 532 including chambers for a matrix 542 and a porous membrane 533, and a bottom layer 534 having a chamber for a desiccant 543. B: Relative movement of the top layer results in a combined sample 544 with the matrix and allows for fluidic communication (e.g., vapor contact shown by arrows), thereby initiating preservation. C: Preservation is complete when the desiccant has absorbed or adsorbed the solvent (e.g., water) from the sample, as evidenced by the presence of hydrated desiccant 546 and a preserved (e.g., in dry or liquid state) or concentrated residual substance 545 in the sample chamber. D and E: Water 547 or any useful solvent (e.g., a buffer) can be injected to provide a rehydrated sample 548, where some samples (e.g., sample 549) can remain preserved by omitting this rehydration step. The following A-E describe the device on the right 560. A: The device 560 includes a top layer 561 having chambers for a sample 571, an intermediate layer 562 including chambers for a matrix 572 and a patterned porous membrane 563, and a bottom layer 566 having a chamber for a desiccant 573. The patterned porous membrane 563 includes regions 564 that allow for fluidic communication between layers or chambers, as well as other regions 565 that resist such fluidic communication. The patterned porous membrane can be integrated into the intermediate layer (e.g., by overmolding or lamination) or can be present in a layer separate from the intermediate layer. B: Relative movement of the top layer results in a sample combined with the matrix 574 and allows for fluidic communication (e.g., vapor contact shown by arrows), thereby initiating drying. C: Drying is complete when the desiccant has absorbed or adsorbed the solvent (e.g., water) from the sample, as evidenced by the presence of hydrated desiccant 576 and a preserved (e.g., in dry or liquid state) or concentrated residual substance 575 in the sample chamber. D and E: Water 577 or any useful solvent (e.g., a buffer) can be injected to provide a rehydrated sample 578, where some samples (e.g., sample 579) can remain preserved by omitting this rehydration step.

In one embodiment, the device includes a membrane as a layer within the device (FIG. 5). Vapor diffusion is allowed between the chambers because the pores of the membrane are too small for aqueous solutions to penetrate. Further, such porous materials may be used to support the drying matrix and/or the sample. Use of a membrane can decrease drying time. For instance, such membranes can maximize the effective interaction area between the sample and the desiccant, as compared to structures including a bridge. As an example, a total volume of 50 µL can be easily dried in less than 10 minutes, while allowing subsequent recovery of RNA even at low concentrations (1000-100 copies/µL). Gel experiments showed recovery of concentrated RNA with no detectable depletion, while qPCR results confirmed the possibility to detect samples as dilute as 100 copies per µL. In addition, a "dry-chip configuration" can be compatible with this strategy, i.e., using a viscous fluid to fill the gap and isolate the chambers, without the need to use a lubricant between the layers of the device.

FIG. 5 (center) provides a schematic representation of one way of implementing the membrane strategy. Recovery is possible by injecting water to rehydrate the sample. Applying external pressure, applying an external low vacuum, or exploiting capillary pressure allows the extraction of the liquid from the device. The layer containing the desiccant may or may not be removed while performing the recovery. In some cases, removing the layer containing the desiccant may be desirable to achieve precise volume quantification in case the drying timescale is comparable to or faster than the hydration timescale.

FIG. 5 (right) provides a device including a slippable, patterned membrane for reversible vapor contact. The membrane can be embedded within a layer, to achieve reversible vapor contact between sample and desiccant. The membrane can thus be operated as a layer capable of relative movement that allows for initiating, pausing, or stopping the drying procedure. This feature will enable partial recovery even when the rehydration and evaporation timescales are comparable.

Sample storage requires mixing with a stabilization matrix. Several matrices are commercially available (e.g., as described herein) and allow stabilization of analytes (such as proteins, RNA, DNA, cells, viruses) in a variety of liquid samples (such as blood, saliva, urine, blood plasma, serum, cell culture medium, environmental sample etc.). The matrix can be introduced to the sample in any useful manner, such as by mixing with the sample prior to loading, pre-loading in the device prior to introducing a sample, or loading the matrix in the device after introducing a sample. In particular embodiments, the matrix can be pre-loaded in the SlipChip device in the liquid or solid state and then mixed with the sample. Prior to mixing, the loaded sample can be split into aliquots, and relative movement can be used to mix each aliquot with the appropriate quantity of matrix. Further, different regions or chambers of the device can be loaded with different stabilization matrices to allow multiplex stabilization. Preliminary results for sample preservation are described herein and provided in FIG. 6.

Multilayer devices can be also used to increase the amount of stored sample (see, e.g., FIG. 7). In some embodiments the architecture may be reproduced several times by stacking several layers, so that total time of drying is preserved (as drying depends on the effective surface for vapor diffusion) or even increased (e.g., each sample can be dried by multiple layers of desiccant). The desiccant can optionally be embedded in a matrix for ease of fabrication. Exemplary matrices for multilayer devices include but are not limited to paper, hydrogels, or any porous hydrophilic medium, such as those described herein. The device can be produced by lamination of several layers, so that each layer can be used as an independent device (e.g., by using strategies such as the valving systems described for a single layer device), and/or by including more than one sample modules and drying modules, as described herein.

Figure 8:
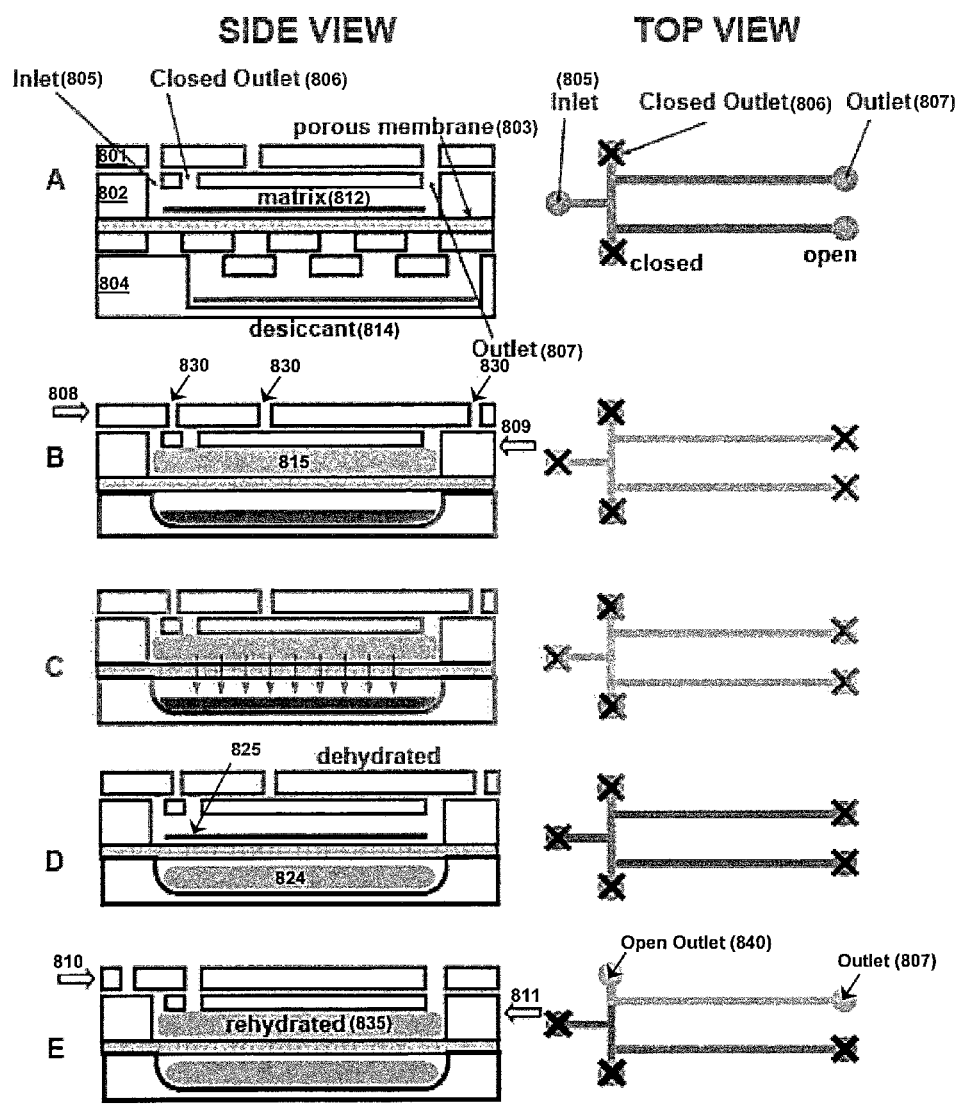
FIGS. 8A-8E provide exemplary schemes for a sample storage device in side view (left) and top view (right). A: The device includes a top layer 801, an intermediate layer 802 including a chamber for matrix 812 and a porous membrane 803, and a bottom layer 804 including a chamber for desiccant 814. B: Introducing a sample and closing the valves by relative movement of top layer 801 results in a combined sample 815 with the matrix. C: Fluidic communication (e.g., vapor contact shown by arrows) between the chambers in the intermediate and bottom layers initiates drying. D: Drying is complete when the desiccant has absorbed or adsorbed the solvent (e.g., water) from the sample, as evidenced by the presence of hydrated desiccant 824 and a dry residual substance 825 in the sample chamber. E: Rehydration can be achieved by injecting any useful solvent (e.g., a buffer) to provide a rehydrated sample 835. For this device, only the top layer 801 needs to be slipped or relatively moved to operate the device. The top view (right) provides how selective rehydration can be achieved by opening and closing selected inlets or outlets, where X indicates a closed inlet or outlet. Inlets and outlets can be placed in the intermediate layer 802. The top layer 801 can include via holes 830 for a valving system. Slipping the layers (as indicated by arrows 808-811) can align/misalign the via holes 830 with inlets and outlets, thereby providing a valving system. For instance, in FIG. 8A, alignment of the via holes with both the inlet 805 and outlet 807 results in an open inlet 805 and an open outlet 807. Misalignment of the via holes with an outlet results in a closed outlet 806. Slipping of the layers (as indicated by arrows 808 and 809) results in closing inlet 805 and outlet 807 (FIG. 8B). Further slipping of the layers (as indicated by arrows 810 and 811) aligns the via holes with the outlets, thereby resulting in open outlets 840 and 807.

Devices can also include automated compartmentalization with simultaneous loading and drying (see FIG. 8). Drying rate can be controlled so that the sample is distributed in all the channel length. Recovery can then be achieved only in portions of the channel, using for example an external valving system. Selective rehydration can be achieved by strategies including but not limited to using different inlet holes that can be opened independently (e.g., using commensurate/incommensurate inlets in a layer, as described, herein and in FIG. 26, and/or controlling the external valves). The top view in FIG. 8 shows the selective recovery principle for a sample stored in two linear channels, where only one line is rehydrated. Complete rehydration can be achieved using the configuration described in FIG. 8A. Grooves or other geometrical features can be included in the channel to create "capillary valves" that prevent the injected liquid from diffusing in the lines that should not be rehydrated. Such techniques can also be included in a multilayer device (see FIG. 9). Multilayer fabrication techniques allow integration of membranes in the device. Reversible vapor contact between the membrane and the desiccant can be achieved with the proposed geometry, where the membrane is embedded in the central layer, and partial recovery can be achieved. An external valving system (e.g., as shown in FIG. 9, right) may be achieved without using a SlipChip device (e.g., by using lids or caps to close the inlets).

For any of the devices described herein, the membrane can be integrated into the device using any useful method. Exemplary methods include but are not limited to bonding using glues or adhesives, bonding using adhesive tapes, bonding using techniques commonly used for thermoplastic materials (such as solvent bonding, thermal bonding), embedding the membrane in a curable material before curing (examples include but are not limited to: epoxy resins, thiolene based optical adhesives, thermal curable materials and photocurable materials), and deposition of a viscous material that can be embedded in the pores by thermal transfer.

Loading such devices can be achieved using any useful method. Precise quantification can be achieved by sequential filling of the chambers. Specific designs of chip geometry can be used to allow sequential filling. Chambers can be filled one by one, and each one will be completely filled before the next one starts filling. In this way, the collected volume can be easily quantified by counting how many wells/channels have been filled. Partial recovery (only from the chambers that were filled in the collection) allows precise quantification of the target molecules of interest. Sequential filling can be obtained using passive strategies, including but not limited to: changing the channel geometry by reducing the cross-section (e.g., by changing one or both the dimensions, producing a narrower or shallower channel to create a "neck"), progressively changing the chamber geometry to increase capillary resistance (e.g., creating a channel with diverging/converging geometry), and changing the local wetting properties of the chambers (e.g., microchannel).

Loading can occur in series or in parallel. For loading in series for one non-limitingembodiment, one inlet is used to load the device, and the device includes a fluidic pathway for sequential filling, where disconnection produces separate aliquots (FIG. 10A). For loading in parallel for one non-limiting embodiment, one inlet is used to load a sample, and the device includes branched pathways that are filled at the same time (FIG. 10B). For one non-limiting embodiment, different loading rates can be used for an array of chambers (FIG. 10C). For one non-limiting embodiment, different samples can be loaded in the device at the same time (FIG. 10D). For each of these loading strategies, conditions can be controlled so that each chamber is completely filled before filling the next or filled at a particular rate. Exemplary strategies to achieve this controlled loading include tuning the chamber geometry (e.g. to create a neck that delays filling), controlling the evacuation speed for the fluid originally present in the chambers (e.g., such as by using air, oil etc.), tuning the geometry so that the fluid is evacuated with a higher or lower fluidic resistance (e.g. evacuation channels at different distance from the sample chambers), using dead-end filling (e.g., as described herein), or using a porous material to achieve sequential filling.

Loading (e.g., by a lid or cap, as described herein) can incorporate features to irreversibly clip the lid to the main device (e.g., to keep the lid in place during transport and to prevent the user from unintentionally opening the lid after loading). Such features can be added externally (e.g., to a housing, as described herein) or to the device itself. Optionally, the lid may include one or more desiccants and/or matrices to dry any excess sample, if present.

In any of the devices herein, samples, analytes, or solutions can be retrieved from a device by connecting a chamber or series of chambers to inlet/outlet holes and then injecting an immiscible fluid (e.g., such as air, gas, mineral oil, a lubricant, etc.) in the chambers so that the samples, analytes, or solutions are pushed out of the device. Alternatively, the samples, analytes, or solutions can be recovered by aspiration through the via holes (e.g., using for example a pipettor, or a low vacuum source).

In any of the devices herein, the sample can be rehydrated by injecting a solvent (e.g., water) in the device, and recovery can be performed on all stored samples or only on the sample stored in a particular chamber or subset of chambers. Further, one or more fluids (e.g., a sample, a reagent, a lubricant, or a matrix) can be injected in the device using any useful loading strategy, e.g., any described herein. Alternatively, some fluids can be pre-loaded in the device before assembly, by depositing such fluids (e.g., as droplets of microdroplets) in a set of chambers. The devices of the invention can be also used for other fluidic operations, such as splitting one volume into further aliquots, creating several sets of aliquots from different solutions, combining two sets of aliquots by mixing each aliquot of solution A with an aliquot of solution B, and/or sequentially mixing each aliquot with a sequence of solution contained in different wells, etc. Sample recovery can include full recovery and recollection or partial recovery and recollection, with storage of the remaining sample. For full recovery, all of the stored sample is rehydrated and recollected from the device at the same time. For example, by re-aligning the chambers so that they form a single path connected to one inlet and one outlet, the single path is filled with a solvent (e.g., water or buffer) to recover the analyte from the device. The final path can be the same used for loading, as the one shown in FIG. 10A. For particulate recovery, a subset of chambers can be aligned in order to form several paths. Each path can be connected to one inlet and one outlet and can be individually addressed. Recovery can thus be performed on the desired subset of chambers, while the remaining chambers are preserved for later recovery. In some embodiments, each chamber can be connected to one inlet and one outlet, and recovery can be performed in a single chamber. Examples of partial recovery are described herein (e.g., in FIGS. 2F, 3F, 4D, 11, and 12).

In any of the devices herein, compartmentalization or partition of the sample can include any useful method. For instance, compartmentalization can be achieved by inducing the breaking of the liquid layer by passive or active strategies. Passive strategies include but are not limited to changing the channel geometry, changing the channel wetting properties, and/or creating specific channel networks to induce liquid breaking during the drying process (including but not limited to channels that are not going to be filled with water during the device loading, for example dead-end channels or by-pass channels). Active strategies include but are not limited to use of relative movement (e.g., by slipping one or more layers to connect or disconnect chambers) and/or use of standard valving systems (e.g., pneumatic or electrovalves) to separate the different portions of the device. Compartmentalization and recovery can be obtained combining a microfluidic device with a valving system. In some embodiments, the device includes multiple layers, and some of the layers may be bonded together (i.e., not slippable).

Sample Concentration

The devices of the invention can be useful for concentrating one or more samples. The sample and/or one or more analytes within the sample can be concentrated by any useful methods, e.g., evaporation. In one non-limiting embodiment, a sample is injected in the device and then exposed to a desiccant or an external atmosphere via a porous material (e.g. membrane). Here, the solvent of the sample will be removed, thus increasing the concentration of the analytes. In further embodiments, evaporation is used to initiate flow within a device, such as using the principles provided in, e.g., Randall et al., Proc. Natl. Acad. Sci. 102:10813-10818 (2005) and Merline et al., Soft Matter 8:3526-3537 (2012), each of which is incorporated by reference in its entirety.

Figure 58:
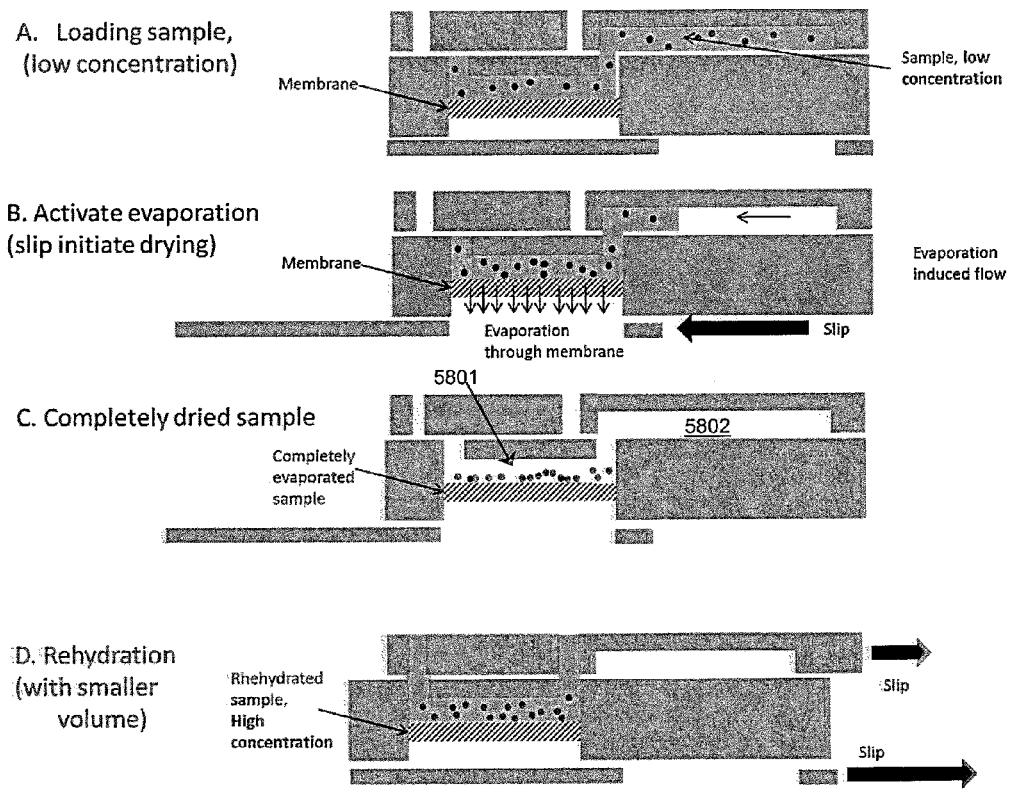
FIGS. 58A-58D provide schemes for concentrating by evaporation with complete drying. A: A sample is loaded in the device, where the sample has an initial low concentration of the target analyte. Here, the sample is present in two chambers 5801 and 5802 located in two different layers. B: Slipping the bottom layer initiates the evaporation. The solvent (e.g., water) evaporates through the membrane driven by vapor contact with a desiccant (not shown, where the desiccant can be preloaded in the device or present in the atmosphere) or by simple diffusion in the atmosphere. Evaporation then induces a liquid flow towards the chamber in direct contact with the membrane. C: After complete drying, the analyte is located in proximity of the membrane. D: Slipping allows disconnection of the two chambers. Only the chamber in contact with the membrane can be rehydrated, so that the final concentration of the target analyte is greater than the initial concentration in the sample. Here, the increase in concentration is roughly equal to the ratio of the volume of chambers 5801 and 5802 to the volume of chamber 5801 (i.e., final concentration/initial concentration=volume of chambers 5801 and 5802/the volume of chamber 5801).
Figure 59:
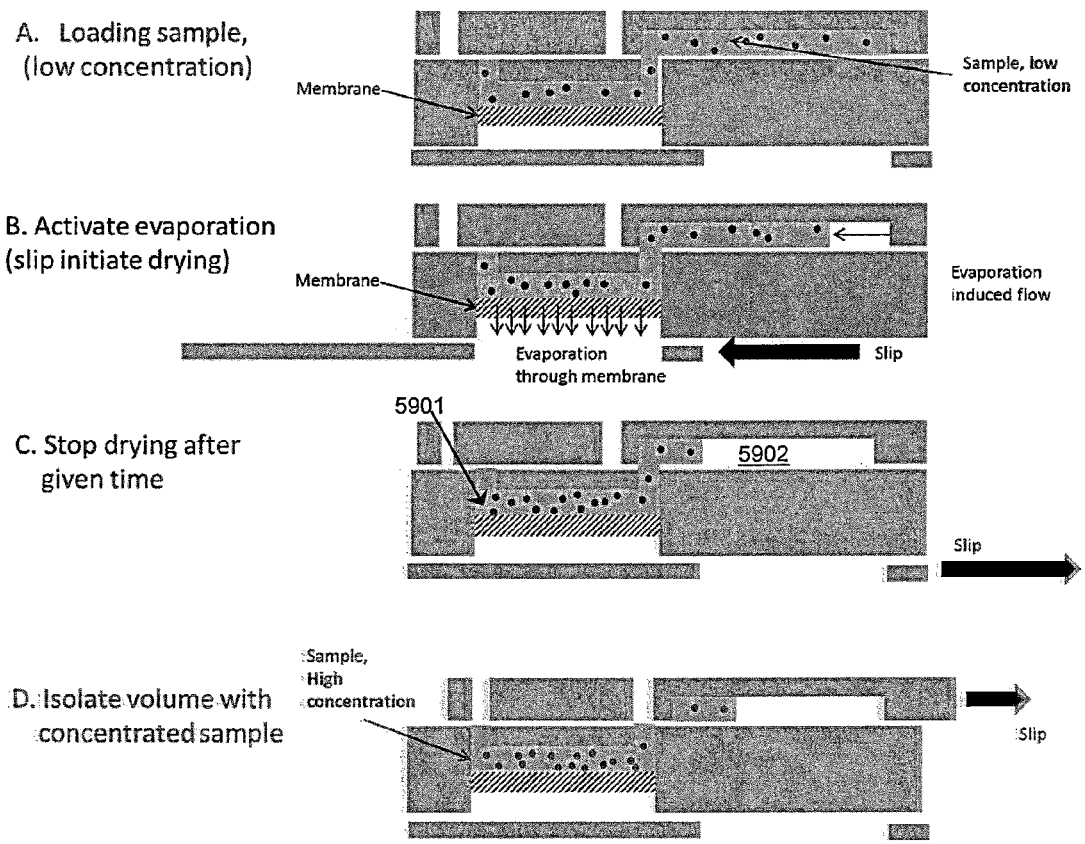
FIGS. 59A-59D provide schemes for concentrating by evaporation with partial drying. A: A sample is loaded in the device, where the sample has an initial low concentration of the target analyte. Here, the sample is present in two chambers 5901 and 5902 located in two different layers. B: Slipping the bottom layer initiates the evaporation. The solvent (e.g., water) evaporates through the membrane driven by vapor contact with a desiccant (not shown, where the desiccant can be preloaded in the device or present in the atmosphere) or by simple diffusion in the atmosphere. Evaporation then induces a liquid flow towards the chamber in direct contact with the membrane. C: After a given time, the analyte is now more concentrated in the chamber 5901 closest to the membrane. D: Slipping allows disconnection of the two chambers. The solution contained in chamber 5901 is now more concentrated than the starting sample solution.
Figure 60:
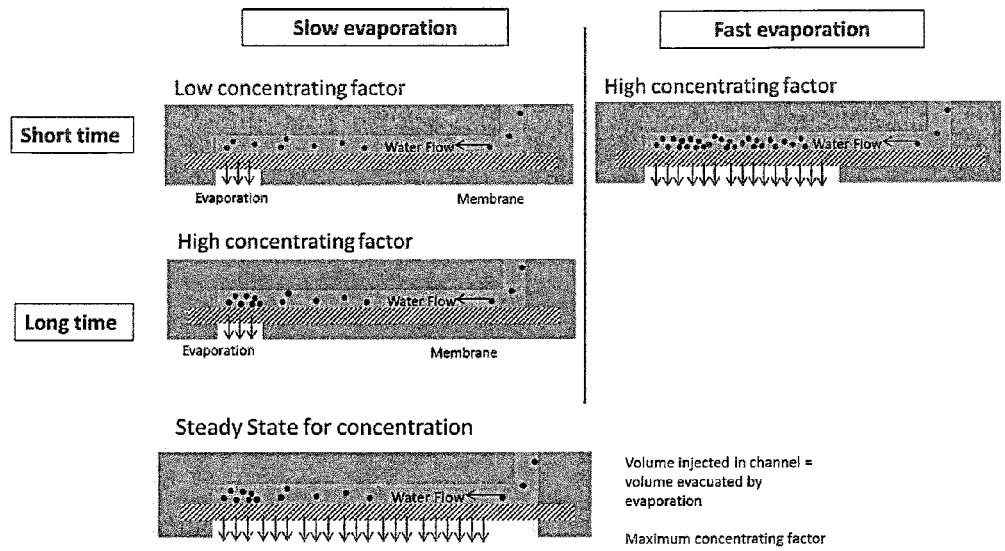
FIG. 60 provides a scheme showing the evaporation rate can be tuned by controlling the geometry of the device or controlling the timescale for drying. For clarity, this figure shows only the central layer from FIGS. 58A and 59A. On a short time scale, the rate of evaporation can be increased by increasing the rate of fluidic communication between the sample chamber and a chamber containing a desiccant.

Evaporation can be controlled by any useful device or method. In one non-limiting embodiment, evaporation results in complete drying of a sample, such as described in FIG. 58. For instance, the solvent for the sample is removed completely, and the resultant analytes are eluted with a known volume of a solution (e.g., water, a buffer, or any fluid described herein). The factor of concentration can be controlled, for example, by controlling the geometry of one or more chambers and/or capture regions. In another non-limiting embodiments, evaporation results in partial drying of a sample, such as described in FIGS. 59-60. For instance, evaporation occurs in a controlled region of the device for a given time. Then, the resultant concentrated solution can be used for further processing. The factor of concentration can be controlled, for example, by controlling the geometry of one or more chambers and/or capture regions, the total evaporation area (e.g., total area of the membrane exposed to the sample), and/or the evaporation time.

For any of the total drying and partial drying approaches, multivolume experiments can be conducted, where a series of aliquots can be processed in different ways and parameters can be tuned to achieve different concentrating factors. Such methods can increase the dynamic range of analyses. Furthermore, these methods can allow for simultaneous loading and drying to maximize the factor of concentration. For example, if the device loading speed is matched with the speed at which the solvent is removed by evaporation, then a steady state flow can be created to maximize the extent of concentrating the analyte (see, e.g., FIG. 60).

Figure 61:
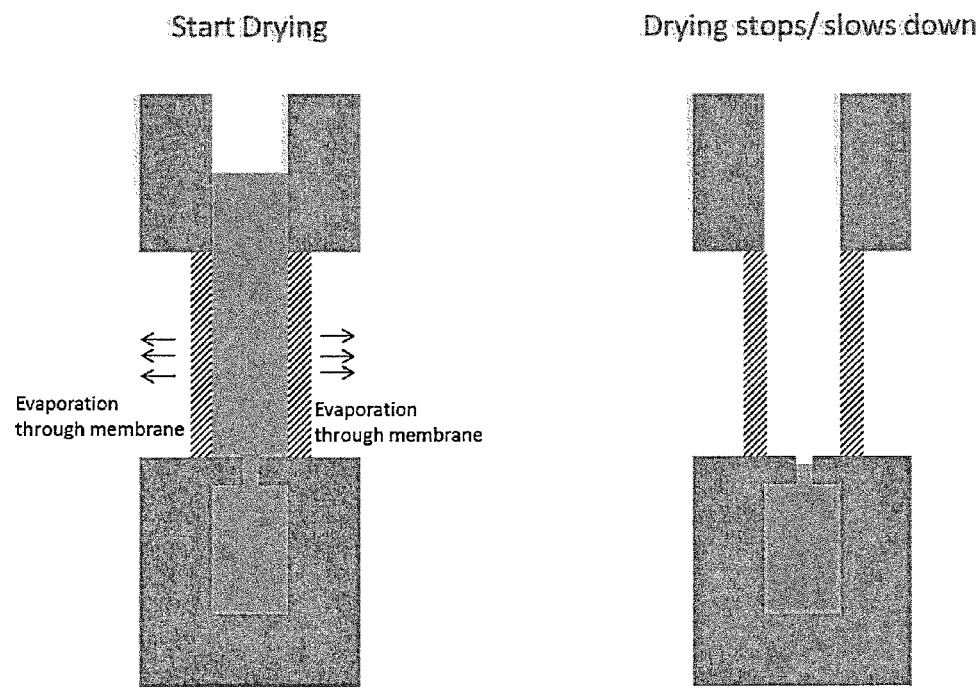
FIG. 61 provides a scheme to automatically control evaporation using a reservoir. Left: The device includes a reservoir filled with a sample. The dashed lines represent a porous material, such as a membrane. In this embodiment, evaporation is driven by a desiccant (not shown) or by exposing to external atmosphere. The reservoir is open at the top inlet. Right: Evaporation stops or slows down considerably when the solution is not in contact with the porous material. Evaporation rate can be reduced or suppressed by tuning the geometry, using, as an example, a neck or constricted chamber (e.g., channel) to minimize the exposed interface. The concentrated solution can be maintained by gravity, capillarity, or any other mechanism.

Optionally, evaporation can be automatically controlled in a device by using any useful structure. In one non-limiting embodiment, the device includes a reservoir filled with water, and a portion of the reservoir includes a porous material (such as, for example, a porous membrane) (see, e.g., FIG. 61). Here, evaporation occurs so long as the sample is still in contact with the porous walls, and the rate of evaporation will decrease as soon as the sample reaches the enclosed extremity of the reservoir. Evaporation rate can be reduced or suppressed by tuning the geometry, e.g., by using a constriction to minimize the exposed liquid interface after the liquid reaches the enclosed extremity of the reservoir. At this point, the evaporation rate will decrease, and a defined volume of the concentrated sample will be kept in place by gravity (in which case the device may or may not need to be kept in a vertical position), by capillary action (in which case the device may or may not include a constriction, as in FIG. 61), or by any other method.

All the above strategies can, for example, be implemented using a device including a membrane (e.g., as described herein), as well as using any of the methods described herein for fluid handling and/or controlled activation/deactivation of preservation of samples.

In some embodiments, rehydration of the preserved sample includes using a volume of fluid (e.g., water, a buffer, or any liquid described herein) that is smaller than the volume of the chamber to be filled with the fluid. In this manner, the final analyte concentration will be greater than the concentration of the analyte in the original sample. Strategies to achieve rehydration with a smaller volume include the use of plug-based microfluidics, such as by partitioning the sample either before or after preservation. In some embodiments, one or more chambers can be loaded with an immiscible fluid (e.g., an oil, a lubricant, or any immiscible fluid, including those any described herein). Then, a droplet (e.g., microdroplet or plug) of a fluid (e.g., aqueous fluid, such as water, a buffer, or any liquid described herein) can be used to recover the preserved sample (e.g., completely or partially dried sample in a solid or liquid state) in the chamber. Exemplary methods and devices are described in U.S. Pat. Nos. 8,304,193; 8,329,407; 8,273,573; 7,901,939; 7,129,091; and 7,655,470, each of which is incorporated herein by reference in its entirety.

Sample preservation can be combined with any sample treatment, sample analysis, or sample concentration methods described herein. For example, sample preservation can be combined with one or more of newborn screening, drug testing, drug discovery, clinical trials, remote clinical trials, sample transportation, transporting, bio-banking, biomarker discovery, archiving (e.g., for tracking an individual patient's history of pathology), long term storage, remote analysis, collateral analysis to point-of-care (POC) or limited-resource settings (LRS) tests, follow up analysis after POC or LRS tests, nucleic acid tests, protein tests, serology, sample processing, analyte stabilization in raw samples, analyte stabilization in purified samples, as well as any additional sample treatment, sample analysis, or sample concentration methods described herein.

Sample Treatment

The devices of the invention can be useful for performing sample treatment (e.g., for detoxifying a sample, preserving a sample, analyzing a sample, or determining the reaction progress of a sample). In particular embodiments, the device for sample treatment is any described herein for preserving or storing a sample (e.g., including one or more membranes and/or bridges). In particular embodiments, the device for sample treatment is any described herein for processing or analyzing a sample (e.g., including one or more capture regions).

In some embodiments, the device (e.g., including one or more membranes and/or bridges, as described herein) is useful for removing and/or collecting a vapor or a gas from the sample. In particular embodiments, the device includes a matrix (e.g., a collection matrix with appropriate selectivity for the vapor or gas of interest, or any described herein), where exposure of the sample to the matrix results in removing and/or collecting the vapor or gas of interest. Exemplary vapors and gases include $H_2S$, oxygen (e.g., $O_2$, as well as radical oxygen species), CO, $CO_2$, methane, sulfur oxides, mercury vapors, vapors of volatile organic compounds, carboxylic acids, amines, aldehydes, odorants, etc. In other embodiments, the device includes a matrix (e.g., a collection matrix with appropriate selectivity for one or more physical or chemical properties, such as polarity, size, charge, density, acidity, basicity, hydrophobicity, lipophilicity, or any described herein), where exposure of the sample to the matrix results in removing and/or collecting the analyte of interest having the desired physical or chemical property.

Exemplary collection matrices include hollow fiber membranes (e.g., poly 2,6-dimethyl-1,4-phenylene oxide) (PPO) and cardo-type polyimide (PI) hollow fiber membranes), nylon membranes (e.g., nylon 6 or nylon 6.6 (polyimide)), polyvinyl alcohol (PVA) membranes, polyacrylonitrile (PAN) membranes, polyurethane (PU) membranes, polyurethane-urea (PUU) membranes, cellulose acetate (CA) membranes, ionic liquids, gels (e.g., a silica gel, such as for adsorption of heavy (polar) hydrocarbons from natural gas), activated carbon/charcoal (e.g, such as for gas storage, trapping mercury vapors, or other odorants), as well as any described herein.

In some embodiments, the matrices may be designed to release a particular substance (e.g., in response to the presence of the target vapor, gas, or analyte, so an exchange process occurs). This could be desirable when the target vapor, gas, or analyte would benefit from being supplemented with the particular substance (e.g., an inert vapor, a preservation vapor, a reaction vapor, a solubilizing agent, a reagent, a buffer, or any useful substance described herein). For example, via such an exchange, a sample (e.g., a biological sample) may be protected, preserved, and/or stabilized.

Various types of sample can be used for sample treatment. Exemplary samples include liquid samples (e.g., for the removal of volatile compounds) or gas samples (e.g., for the removal of some compounds from the gas mixture), as well as any described herein. Exemplary sample treatment steps include removing one or more contaminants, such as, for example, one or more toxic components, interfering components, or volatile components (e.g., prior to sample analysis in the device or prior to sample stabilization or preservation in the device), removing substances (e.g., oxygen) for enhancing preservation of such sample, and/or capturing one or more analytes of interest. In any of these embodiments, the matrix can be further analyzed, such as by removing the matrix from the device or by exposing the matrix to one or more elution buffer and analyzing the resultant eluent. In particular non-limiting embodiments, the device is made from materials not permeable or minimally permeable to the vapors being collected. A substantial expertise exists in the industry, for example, in plastic films that reduce oxygen and water vapor permeability. For example, permeability of cyclic olefin copolymer (COC) and cyclic olefin polymer (COP) is generally lower than that of polycarbonate (PC). Exemplary COC and COP include copolymers including norbornene (e.g., with ethene or ethylene), copolymers including tetracyclododecene (e.g., with ethene or ethylene), including TOPAS® COC containing an ethylene-norbornene copolymer (e.g., TOPAS-8007 (Tg=78° C.), TOPAS-5013 (Tg=130° C.), TOPAS-6015 (Tg=160° C.), and TOPAS 6017 (Tg=130° C.)), as well as any described herein.

Sample Preparation

The devices of the invention are useful for methods of processing, preparing, and/or analyzing a sample (e.g., any described herein). Such methods benefit from the devices of the invention, which include one or more layers, one or more chambers, and/or one or more capture regions capable of being connected or disconnected by relative movement. In particular, each step of these methods can be accomplished by controlling such relative movement, where even complicated or reiterated steps can be accommodated by controlling relative movement and by designing appropriate layers. For instance, a particular relative step between reagent(s) and the sample in different layers can be initiated by relatively moving the layers of the device to connect chambers containing the desired reagent(s) and sample.

The methods can further include partitioning a test sample (e.g., having a volume of more than about 1 mL) into separate aliquots (e.g., a plurality of droplets or a plurality of microdroplets each having a volume of less than about 1 mL), drying one or more of the aliquots (e.g., using one or more desiccants, as described herein), and/or recovering one or more of the aliquots (e.g., using one or more solvents, such as water, a buffer, or an organic solvent, as described herein). The volume of each aliquot can be controlled by appropriately sized chambers. Furthermore, such aliquots can be further compartmentalized by use of a lubricant to encapsulate the aliquot within a droplet or microdroplet. In particular embodiments, the volume is less than about 1 µL, 750 µL, 500 µL, 250 µL, 100 µL, 50 µL, 10 µL, 5 µL, 1 µL, 750 nL, 500 nL, 250 nL, 100 nL, 50 nL, 10 nL, 5 nL, 1 nL, 750 pL, 500 pL, 250 pL, 100 pL, 50 pL, 10 pL, 5 pL, 1 pL, 750 fL, 500 fL, 250 fL, 100 fL, 50 fL, 10 fL, 5 fL, 1 fL, 750 aL, 500 aL, 250 aL, 100 aL, 50 aL, 10 aL, 5 aL, or 1 aL. In other embodiments, the volume is from about 1 aL to about 1 mL (e.g., 1 aL to 750 µL, 1 aL to 500 µL, 1 aL to 250 µL, 1 aL to 100 µL, 1 aL to 50 µL, 1 aL to 10 µL, 1 aL to 5 µL, 1 aL to 1 µL, 1 aL to 750 nL, 1 aL to 500 nL, 1 aL to 250 nL, 1 aL to 100 nL, 1 aL to 50 nL, 1 aL to 10 nL, 1 aL to 5 nL, 1 aL to 1 nL, 1 aL to 750 pL, 1 aL to 500 pL, 1 aL to 250 pL, 1 aL to 100 pL, 1 aL to 50 pL, 1 aL to 10 pL, 1 aL to 5 pL, 1 aL to 1 pL, 1 aL to 750 fL, 5 aL to 1 mL, 5 aL to 750 µL, 5 aL to 500 µL, 5 aL to 250 µL, 5 aL to 100 µL, 5 aL to 50 µL, 5 aL to 10 µL, 5 aL to 5 µL, 5 aL to 1 µL, 5 aL to 750 nL, 5 aL to 500 nL, 5 aL to 250 nL, 5 aL to 100 nL, 5 aL to 50 nL, 5 aL to 10 nL, 5 aL to 5 nL, 5 aL to 1 nL, 5 aL to 750 pL, 5 aL to 500 pL, 5 aL to 250 pL, 5 aL to 100 pL, 5 aL to 50 pL, 5 aL to 10 pL, 5 aL to 5 pL, 5 aL to 1 pL, 5 aL to 750 fL, 1 fL to 1 nL, 1 fL to 750 µL, 1 fL to 500 µL, 1 fL to 250 µL, 1 fL to 100 µL, 1 fL to 50 µL, 1 fL to 10 µL, 1 fL to 5 µL, 1 fL to 1 µL, 1 fL to 750 nL, 1 fL to 500 nL, 1 fL to 250 nL, 1 fL to 100 nL, 1 fL to 50 nL, 1 fL to 10 nL, 1 fL to 5 nL, 1 fL to 1 nL, 1 fL to 750 pL, 1 fL to 500 pL, 1 fL to 250 pL, 1 fL to 100 pL, 1 fL to 50 pL, 1 fL to 10 pL, 1 fL to 5 pL, 1 fL to 1 pL, 1 fL to 750 fL, 1 pL to 1 mL, 1 pL to 750 µL, 1 pL to 500 µL, 1 pL to 250 µL, 1 pL to 100 µL, 1 pL to 50 µL, 1 pL to 10 µL, 1 pL to 5 µL, 1 pL to 1 µL, 1 pL to 750 nL, 1 pL to 500 nL, 1 pL, to 250 nL, 1 pL to 100 nL, 1 pL to 50 nL, 1 pL to 10 nL, 1 pL to 5 nL, 1 pL to 1 nL, 1 pL to 750 pL, 1 pL to 500 pL, 1 pL to 250 pL, 1 pL to 100 pL, 1 pL to 50 pL, 1 pL to 10 pL, 1 pL to 5 pL, 1 nL to 1 mL, 1 nL to 750 µL, 1 nL to 500 µL, 1 nL to 250 µL, 1 nL to 100 µL, 1 nL to 50 µL, 1 nL to 10 µL, 1 nL to 5 µL, 1 nL to 1 µL, 1 nL to 750 nL, 1 nL to 500 nL, 1 nL to 250 nL, 1 nL to 100 nL, 1 nL to 50 nL, 1 nL to 10 nL, or 1 nL to 5 nL).

Various types of sample preparation and analysis can be conducted in the devices of the invention. Exemplary sample preparation and analysis include nucleic acid extraction, nucleic acid purification, nucleic acid enrichment, nucleic acid concentration, protein extraction, protein purification, protein enrichment, protein concentration, cell separation, sample enrichment, nucleic acid amplification, nucleic acid detection, protein detection, filtration, lysis, dehydration, rehydration, a binding reaction, a washing step, elution, an assay reaction, and/or detection of one or more samples or one or more analytes within a sample.

In particular, the methods described herein can be beneficial when analyzing samples with low concentrations of analytes, for example, dilute samples; rare nucleic acids, proteins, markers, and biomarkers of genetic or infectious disease; environmental pollutants; rare cells, such as circulating cancer cells, stem cells, or fetal cells in maternal blood for prenatal diagnostics; microbial cells in blood, sputum, bone marrow aspirates and other bodily fluids such as urine and cerebral spinal fluid for rapid early diagnostics of infections; viral loads (e.g., for HIV and/or HCV) in samples (e.g., in samples from subjects having or suspected of having chlamydia, gonorrhea, and/or HIV); enzymatic assays; cellular assays, such as to determine cell viability, cell adhesion, cell binding etc.; biological or chemical screens for catalytic activity, selectivity, or storage ability or sequestration (such as absorption of gas or trapping of toxic compounds, etc.); or analytical testing various properties such as electrical, magnetic, optical, etc. See e.g., U.S. Pub. Nos. 2005/0003399 and Int. Pub. No. WO 2009/048673, incorporated herein by reference. In particular, detecting low concentrations of an analyte (e.g., a single molecule or a single bacterium) remains a challenge in food, medical, and security industries. The device of the invention could be useful for concentrating such samples and performing analysis. In one example, the devices of the invention can be useful for creating a high local concentration of an analyte (e.g., by compartmentalization within a chamber and/or a droplet or by concentration by using a capture region) that would only be present in dilute concentrations for a bulk solution. In another example, devices of the invention can create high local concentrations of an analyte that can further be amplified, such as by PCR with a DNA sample or by quorum sensing with a bacterial sample. Accordingly, the devices of the invention can be used in combination with any useful PCR technique. Exemplary PCR techniques are disclosed in the following publications: US 2008/0166793, WO 08/069,884, US 2005/0019792, WO 07/081,386, WO 07/081,387, WO 07/133,710, WO 07/081,385, WO 08/063,227, US 2007/0195127, WO 07/089,541, WO 07/030,501, US 2007/0052781, WO 06/096571, US 2006/0078893, US 2006/0078888, US 2007/0184489, US 2007/0092914, US 2005/0221339, US 2007/0003442, US 2006/0163385, US 2005/0172476, US 2008/0003142, and US 2008/0014589, each of which is incorporated by reference herein in its entirety. The following articles, describing methods for concentrating cells and/or chemicals by making small volume areas with low numbers of items to no items being incorporated into the areas, with specific applications involving PCR, are incorporated by reference herein: Koh et al., Anal. Chem. 75:4591-4598 (2003); Gulliksen et al., Lab Chip. 5:416-420 (2005); Abrams et al., Ann N Y Acad. Sci. 1098:375-388 (2007); Cady et al., Proc. IEEE Sensors, 24-27 Oct. 2004 3:1191-1194 (2004); Ottesen et al., Science 314:1464-1467 (2006); Govind et al., Electrophoresis 27:3753-3763 (2006); Lapizco-Encinas et al., J. Microbiol. Methods 62:317-326 (2005); Wong et al., Anal. Chem. 76:6908-6914 (2004); Yang et al., Lab Chip 2:179-187 (2002); Du et al., Anal. Chem. 77:1330-1337 (2005); Huang et al., Science 315:81-84 (2004); Hong et al., Nat. Biotechnol. 22:435-439 (2004); Liu et al., Electrophoresis 23:1531-1536 (2003); Matsubara et al., Biosens. Bioelectron. 20:1482-1490 (2005); and Leamon et al., Nat. Methods 3:541-543 (2006).

The device of the present invention can be used to study and perform coagulation or clotting assays, protein aggregation, protein crystallization (including the use of lipidic cubic phase), crystallization and analysis of small molecules, macromolecules, and particles, crystallization and analysis of polymorphs, crystallization of pharmaceuticals, drugs and drug candidates, biomineralization, nanoparticle formation, the environment (via aqueous and air sampling), culturing conditions (e.g., stochastic confinement, lysis of cells, etc.), drug susceptibility, drug interactions, high throughput screening (e.g., one first substance with many, different second substances, or many, different first substances with many, different second substances), multiplex assays (e.g, PCR, Taqman, immunoassays (e.g., ELISA, FISH, etc.)), amplification (e.g., PCR, ligase chain reaction (LCR), transcription mediated amplification (TMA), reverse transcriptase initiated PCR, DNA or RNA hybridization techniques, sequencing, and the like), sandwich immunoassays, chemotaxis assays, ramification amplification (RAM), etc. Exemplary techniques for blood assays, crystallization assays, protein aggregation assays, culturing assays are described in U.S. Pat. Nos. 7,129,091, 6,949,575, 5,688,651, 7,329,485, 6,949,575, 5,688,651, 7,329,485, and 7,375,190; U.S. Pub. Nos. 2007/0172954, 2006/0003439, 2003/0022243, and 2005/0087122; and Int. Pub. Nos. WO 2007/089777 and WO 2009/015390, each of which is incorporated herein by reference in its entireties. The device of the present invention can be used for various syntheses, including catalysis, multistep reactions, immobilized multistep synthesis (e.g., small molecule, peptide and nucleic acid syntheses), solid state synthesis, radioisotope synthesis, etc. Finally, the device of the present invention can be used for purification and enrichment of samples.

In some embodiments, the device can contain chambers that are used as a positive control (e.g., an analyte pre-loaded in a chamber) and/or a negative control (e.g., a buffer pre-loaded in a chamber).

The devices and methods of the invention can be used to conduct any useful reaction. Exemplary, non-limiting reactions include photochemical and electrochemical reactions, chemical reactions such as synthetic reactions (e.g., synthesis of radioisotopes), neutralization reactions, decomposition reactions, displacement reactions, reduction-oxidation reactions, precipitation, crystallization (e.g., protein crystallization by free interface diffusion and/or vapor diffusion), combustion reactions, and polymerization reactions, as well as covalent and noncovalent binding, phase change, color change, phase formation, dissolution, light emission, changes of light absorption or emissive properties, temperature change or heat absorption or emission, conformational change, and folding or unfolding of a macromolecule such as a protein. Multistep reactions may be performed by controlling conditions at each subsequent relative movement of the device.

The device of the present invention can be designed to load multiple areas with different substances easily and economically. For example, in FIG. 25, the device is manufactured to include multiple chambers for preserving and analyzing samples 1, 2, and 3. Furthermore, each layer 2501, 2502, and 2503 can be designed to perform a particular function. For example, layer 2501 allows for sample preparation (e.g., by including one or more desiccants, such as any described herein), layer 2502 allows for sample purification (e.g., by use of one or more capture regions, such as any described herein), and layer 2503 allows for sample collection (e.g., any useful sample described herein).

In other embodiments, the device could contain a plurality of chambers configured in the same locations as a standard multi-well plate or configured radially (e.g., such as in FIG. 25).Each layer can contain, for example, 6, 24, 96, 384, 1536, 3456, or 9600 chambers. In other embodiments, the device could contain at least about 1, 2, 3, 4, 5, 6, 7, 8, 9, 10, 20, 24, 30, 40, 48, 50, 60, 70, 80, 90, 96, 100, 200, 300, 384, 400, 500, 512, 1000, 1500, 1536, 2000, 2500, 3000, 3456, 3500, 4000, 4500, 5000, 6000, 7000, 8000, 9000, 9600, 10000, 1500, 2000, 2500, 3000, 4000, 5000, 6000, 7000, 8000, 9000, 10000, 20000, 30000, 40000, 50000, 60000, 70000, 80000, 90000, 100000, 200000, 200000, 400000, 500000, 600000, 700000, 800000, 900000, 1000000, or more chambers.

Figure 14:
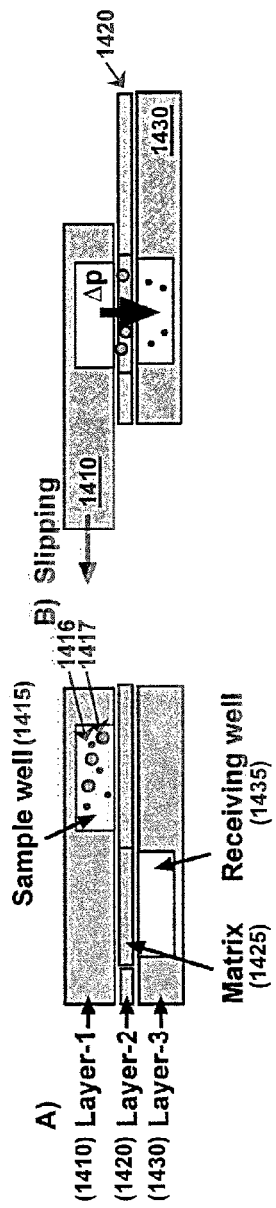
FIGS. 14A-14B provide an exemplary scheme of a SlipChip for sample preparation. A: The device includes a top layer 1410 (Layer-1) including a chamber 1415 (e.g., a sample well), an intermediate layer 1420 (Layer-2) including a capture region 1425 (e.g., a matrix), and a bottom layer 1430 (Layer-3) including a chamber 1435 (e.g., a receiving well). The sample includes both larger analytes 1417 and smaller analytes 1416. B: Relative movement connects the sample well 1415, matrix 1425, and receiving well 1435, and a pressure change drives the sample through the matrix. Based on the size exclusion characteristics of the matrix, larger analytes 1417 are trapped in the matrix, and smaller analytes 1416 are transported through the matrix and into the receiving well.

SlipChip is able to perform sample preparation by filtration, and the same approach can also be used for target enrichment. As shown in FIG. 14, a matrix 1425, such as a filtration membrane, gel, and through holes/pores, can be brought in contact with collected sample by slipping the first layer 1410 with respect to the second and/or third layer (1420 and/or 1430). With a driving force, such as positive pressure, negative pressure, or gradient, only the particles and molecules in the sample layer with size smaller than the matrix pore size (i.e., particles 1416) can pass through the matrix 1425 in the second layer 1420 and enter the receiving well 1435 in the third layer 1430 (FIG. 14). Larger particles 1417 will remain in the sample well 1415 or be captured in the matrix 1425. In some cases, the material passing through the size selection matrix can be used for downstream analysis, such as immunoassay, or further sample manipulation, such as nucleic acid extraction. In some cases, particles larger than the pore size (i.e., particles 1417) can be enriched on the matrix 1425, and further analysis can be directly applied on the matrix, such as for example, cell counting, cell lysis, and nucleic acid extraction (FIG. 14).

Alternatively, the matrix may contain capture molecules, such as aptamers and ChargeSwitch® materials to concentrate/enrich target molecule. In other cases, the matrix may contain capture molecules to remove target molecules or analytes, such as inhibitors, from the sample solution.

For example, this general method can be applied for plasma separation from whole blood. We designed and optimized a plasma separation module with Pall® vivid plasma separation membrane as the matrix. Approximately 1/50 of atmosphere positive pressure is applied to increase the speed of plasma filtration. This plasma preparation device was able to prepare approximately 10 to 20 µL of cell-free plasma from 100 µL of whole human blood within 60 seconds. Free flow plasma can be collected from the bottom of the device. No blood cells from prepared plasma were observed by using stereoscope.

Alternatively, this SlipChip can be applied for white blood cell enrichment. A membrane of white blood cell isolation (leukosorb) medium can be integrated in the device as matrix. Whole blood can be driven through the matrix by pressure or gravity, and the white blood cells can be trapped in the matrix for downstream analysis.

The device can control the total volume passing through separation matrix by a dead-end filling method instead of using valves, plungers or other fluidic control methods. The total passing volume during sample preparation is defined by the volumes of receiving chambers. Therefore, as long as the process pressure is less than the leaking pressure, the aqueous fluid will be contained without leaking by capillary force. This dead-end filling feature enables the device to process multiple samples in parallel, manipulate single or multiple samples with multistep procedure and process samples in multiple volumes. This method also enables robust and accurate volume control which is defined by the volume of receiving wells.

Sample preparation is a critical step to enable downstream reactions and analysis, such as nucleic acid amplification and immunoassays. Current sample preparation methods generally require multiple instruments, plug-in power supply, and trained personnel, which are less favorable in point-of-care and resource limited settings. The device of the invention can perform sample preparation without complex fluidic manipulation systems, such as pumps, valve, syringe barrels, etc. Such devices can perform sample preparation by relative movement of layers to bring sample solution and different reagents, such as washing and elution buffers, in or out of contact with sample preparation matrix. Relative movement of different plates/layers can be translational, rotational or a combination of both.

A multilayer approach can be used to extend the capability of the device further, such as integration of modules with various functions. Each layer can be designed to move freely (e.g., slip) relative to other layers. For example, in sample preparation, the separation matrix or nucleic acid extraction matrix can be embedded in the intermediate layer, reagent chambers are provided in the top layer, and receiving chambers are provided in the bottom layer. By slipping the intermediate layer, the capture region or matrix is aligned with each set of reagent chamber and receiving chamber, respectively. Receiving chambers with dead-end filling design can be used to control precisely the solution volume passing through the matrix. The speed of oil or lubricant displacement can be controlled by the gap and surface chemistry.

Figure 15:
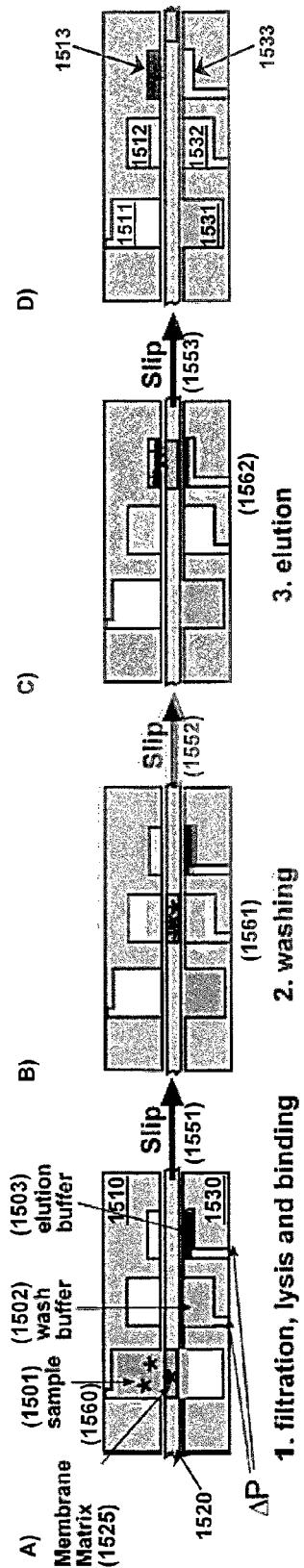
FIGS. 15A-15D provide an exemplary scheme for a representative translational SlipChip for sample preparation. A: The device includes a top layer 1510 including a plurality of chambers 1511-1513 and an inlet 1560, an intermediate layer 1520 including a capture region 1525 (e.g., a membrane matrix), and a bottom layer 1530 including a plurality of chambers 1531-1533. For performing the filtration, lysis, and binding reactions, the chamber in the top layer 1510 includes a sample 1501, and the chambers in the bottom layer 1530 include a wash buffer 1502 and an elution buffer 1503. Fluidic communication between the sample chamber 1511, the membrane matrix 1525, and the sample receiving chamber 1531 allows transport of the sample through the membrane matrix, thereby trapping the analytes (asterisks) in the matrix. B: Relative movement (arrow 1551, e.g., by slipping) connects the wash buffer chamber 1532, the matrix 1525 including the analytes, and the wash buffer receiving chamber 1512. Application of pressure at inlet 1561 for the wash buffer chamber transports the wash buffer through the matrix, which washes the matrix. C: Relative movement (arrow 1552, e.g., by slipping) connects the elution buffer chamber 1533, the matrix 1525 including the analytes, and the elution buffer receiving chamber 1513. Application of pressure at inlet 1562 for the elution buffer chamber transports the elution buffer through the matrix, which elutes the analytes from the matrix and into the chamber 1513. The device can include other structures, such as one or more chambers to transport the analytes to be reacted with one or more reagents for further sample analysis, detection, and/or storage.

For example, in a translational SlipChip design (FIG. 15), the membrane matrix 1525 is first aligned with sample well 1511 in the top layer 1510 and receiving well 1531 in the bottom layer 1530. The sample 1501 containing analytes (asterisks) is pushed (arrow 1560) through the membrane 1525, and the analytes are captured on the membrane matrix 1525. Then, the middle layer 1520 is slipped (arrow 1551) to align the membrane matrix 1525 with washing buffer 1502 in buffer well 1512 and with the respective receiving well 1512. One or multiple washing steps (arrow 1561) can be applied to wash away impurity from membrane. Then, the middle layer is slipped (arrow 1552) to align the membrane matrix 1525 with elution buffer 1503 in the elution well 1513 and with the respective receiving well 1533. One or multiple elution steps (arrow 1562) can be applied to elute analytes from the membrane for downstream analysis.

Figure 16:
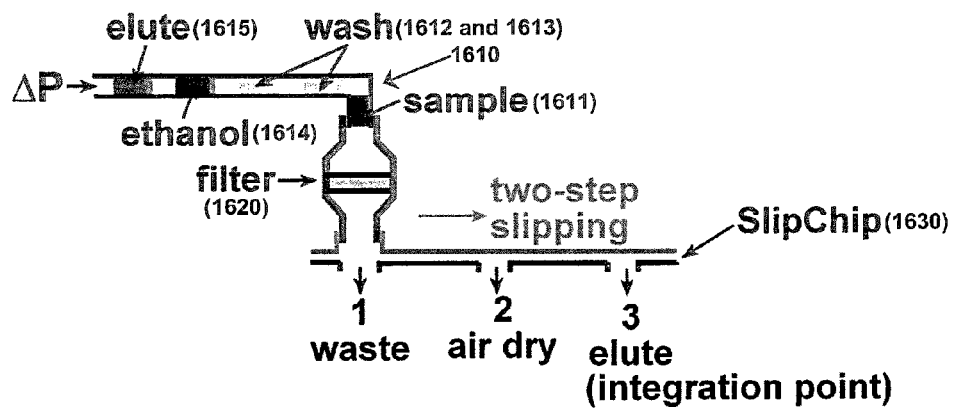
FIG. 16 shows an exemplary scheme for sample preparation in a SlipChip by incorporation of a filter 1620 and a cartridge 1610. The cartridge 1610 includes a sample 1611, one or more wash buffers 1612 and 1613, ethanol 1614, and an elution buffer 1615. The cartridge can be interfaced via a filter 1620 to a SlipChip device 1630, such as any described herein.
Figure 17:
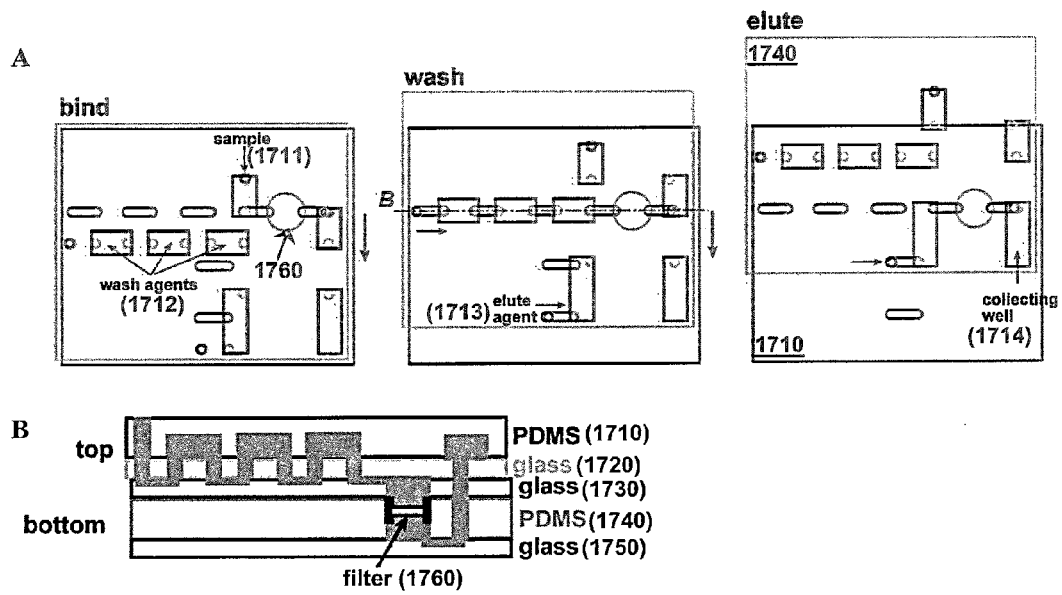
FIGS. 17A-17B show schemes for an exemplary non-limiting SlipChip for sample preparation in plan view (A) and cross-sectional view (B, along dotted line marked "B" in FIG. 17A). A: The device can include one or more structures to contain a sample 1711, wash agents 1712, and elute agents 1713. Relative movement (e.g., by slipping) of the top layer 1710 and the bottom layer 1740 allows for connecting or disconnecting various chambers, filter 1760, and collection well 1714. B: The device can include a first layer 1710 (top PDMS layer), a second layer 1720, a third layer 1730, a fourth layer 1750 (bottom PDMS layer), and a fifth layer 1750.

Alternatively, to integrate the filter-based method with the SlipChip platform, we developed an exemplary pressurization protocol. An array 1610 of agents, lysed sample 1611, washing buffers 1612 and 1613, ethanol 1614, and elution buffer 1615 can be delivered through a separation filter 1620. Filtrants can be collected in portions defined by slipping the layers of the SlipChip device 1630 to different positions. The array 1610 of agents can be pre-formed in a piece of tubing (FIG. 16) or preloaded on a SlipChip (FIG. 17). When the array is formed on a SlipChip device, different reagents can be first preloaded separately. Relative movement (e.g., by slipping) connects the reagents to form an array that is then delivered through the filter. Meanwhile, elution buffer can be loaded. Another relative movement (e.g., by slipping) can disconnect the cartridge from the filter and connects the elution buffer to the filter to elute the sample.

The cartridge based method can also be incorporated in a complete SlipChip device (FIG. 17). In the first binding position (FIG. 17A, left), sample 1711 can be loaded and transferred through the filter 1760 for target binding. By slipping to the washing position (FIG. 17A, center), washing agents 1712 are transferred through the filter while allowing eluting agents to be loaded. By slipping to the elute position (FIG. 17A, right), eluting agent 1713 is transferred through the filter, delivering the target to the collecting well 1714 for further manipulation coupled to target quantification. FIG. 17B provides a cross-section of the device with a filter 1760, a top PDMS layer 1710, a bottom PDMS layer 1740, and various glass layers 1720, 1730, and 1750. In one non-limiting embodiment, the filter is a directly connected, modified filter from QiaAMP MinElute (Qiagen). An exemplary, simplified version of a SlipChip device for nucleic acid extraction is described in FIG. 16 and Example 2 herein. In particular embodiments (e.g., in the manufacturing process), layer 1710 can be of a blister type for reagent storage. In some embodiments (e.g., in the manufacturing process), filter 1760 is fabricated by lamination on a thermoformed chip. In other embodiments (e.g., in the manufacturing process), the device can be fabricated with a cavity, and filter 1760 (e.g., previously fabricated and/or purchased filter) is inserted into the cavity. In yet other embodiments (e.g., in the manufacturing process), the device can be fabricated with a cavity, and filter 1760 can be fabricated by overmolding. The device can include any number of useful layers useful for sample preparation and/or sample preservation, such as two layers (e.g., as described in FIG. 14, where Layer-2 and Layer-3 are fabricated in a single layer), three layers (e.g., as described in FIG. 14, where each of Layer-1, Layer-2, and Layer-3 are fabricated in three separate layer), or multiple layers (e.g., as described in FIGS. 17A-17B).

For example, sample preparation can be used in a rotational multilayer SlipChip design (FIGS. 18A-18B). First, the membrane matrix 1821 (or filter) is first aligned with sample well 1811 in the top layer 1810 and one of the receiving well 1830 in the bottom layer 1830 (FIG. 18B(i)). The sample containing analytes 1811 is pushed through the membrane, and the analytes are captured on the membrane matrix 1821. Additional washing and eluting steps can be accomplished by using a pressure source to push washing reagents 1812 (as in FIG. 18B(ii)) and/or elution reagents 1813 (as in FIGS. 18B(iii)-(iv)) though the membrane matrix 1821 containing the analyte.

As shown in FIG. 18A, the top portion 1801 of device 1800 can rotate with respect to the bottom portion 1802. In this way, the sample 1811 is first aligned with the membrane matrix 1821 to capture analytes within the membrane matrix. Then, the top portion 1801 can be rotated to align the washing chambers 1812 (four such chambers are provided in FIG. 18A) with the membrane matrix 1821 containing the captured analyte. Finally, the top portion 1801 can be rotated to align the eluting chambers 1813 (four such chambers are provided in FIG. 18A) with the membrane matrix 1821. As can be seen in FIGS. 18A-18B, the top portion 1801 or the bottom portion 1802 of the device can rotate, so long as rotation occurs with respect to these two portions. Exemplary, non-limiting prototypes and their use are provided in FIGS. 19A-19B and 20A-20B and Examples 3-7.

In particular embodiments, a cap 2003 (FIGS. 20A-20B) can be put on top of the device and tighten to provide positive pressure; 2) rotate layer 2001 (FIG. 15A) and align the membrane matrix 2010 with washing buffer (e.g., 100 µl each) and receiving well; multiplex washing steps can be applied to wash away impurity from membrane; 3) rotate layer 2001 and align the membrane matrix 2010 with elution buffer (50 µL each); multiple elution steps can be applied to elute analytes from the membrane for downstream analysis. For example, we have designed a third generation device (described in FIG. 20 and Example 4 herein) with a cap that can be used to apply positive or negative pressure to drive solution through the matrix (FIG. 22B). In some cases, by using the cap to decrease the enclosed volume in pressurization chamber, positive pressure can be applied to the whole system; in other cases, by using the cap to increase the enclosed volume in pressurization chamber, negative pressure can be applied to the whole system. Exemplary pressure capping system is provided in FIGS. 33A-33B and Example 8 herein.

Figure 19:
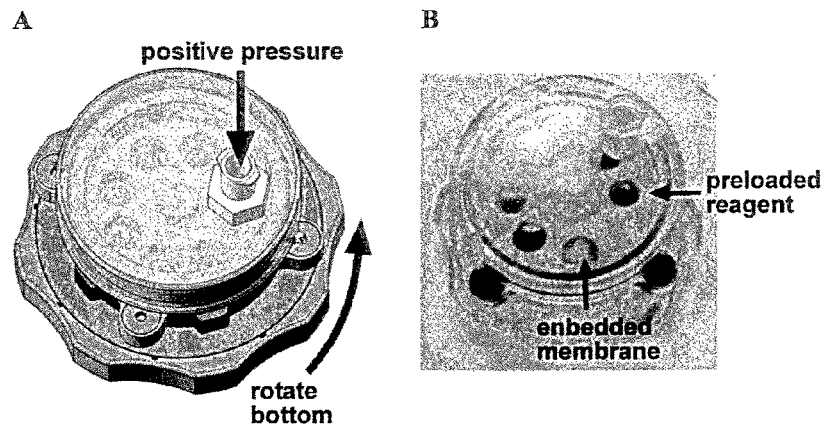
FIGS. 19A-19B provide a device for nucleic acid purification from spiked plasma sample as a scheme (A) and as a prototype (B).
Figure 20:
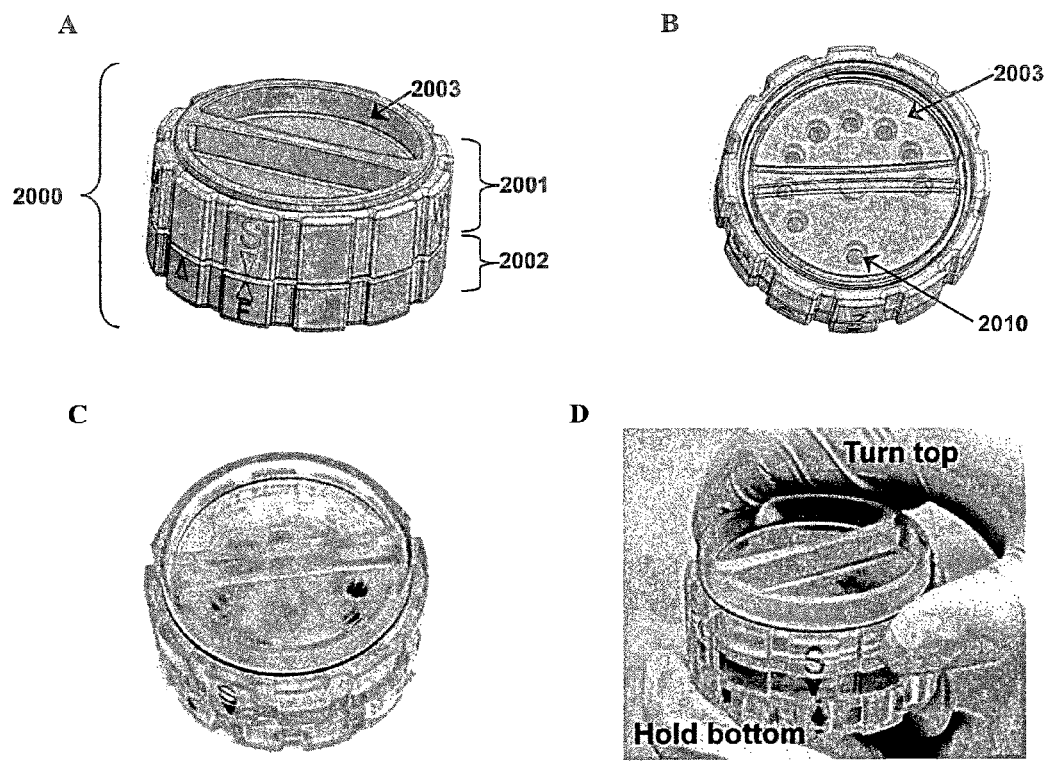
FIGS. 20A-20D provide a device with an integrated pressurization module as a scheme (A, B) and as a photograph (C, D). The device 2000 includes a sample chamber 2010, a housing system having a top portion 2001 and a bottom portion 2002, and a cap 2003 for enclosing the system.
Figure 21:
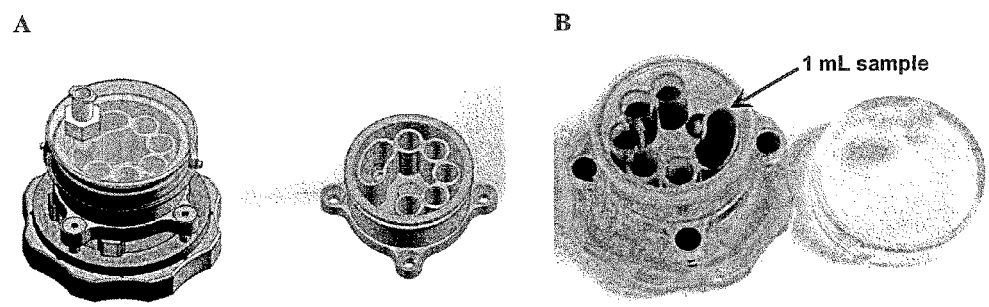
FIGS. 21A-21B provide a SlipChip device for processing a large volume of sample (e.g., more than or equal to about 1 mL of a sample) as a scheme (A) and as a bright field image (B).

This SlipChip platform can be fabricated from a variety of materials, such as glass and plastic (see, e.g., exemplary prototypes provided in FIG. 19-21). We have previously demonstrated a plastic rotational SlipChip with user friendly features by using 3D-printing (see, e.g., FIG. 36). A user simply loads the sample into the sample chamber, close the lid to apply pressure, hold bottom disc and rotate the top portion to perform sample preparation.

The SlipChip platform can be compatible with a large variety of nucleic acid sample preparation methods, such as, for example, a combination of a chaotropic substance and a particle (e.g., any described herein, such as guanidinium thiocyanate with size-fractionated $SiO_2$ particles or with diatomaceous silicas (e.g., Celite®), as described in Boom et al., J. Clin. Microbiol. 28:495-503 (1990)), ChargeSwitch® and FTA (Whatman, GE) Chemistry. For example, SlipChip platform with ChargeSwitch® membrane has been validated with extraction of HIV viral RNA from spiked human plasma sample with efficiency comparable to commercial nucleic acid preparation method (see Examples herein).

SlipChip can integrate temperature control methods suitable for sample lysis for nucleic acid extraction, such as for example, temperature control methods based on simple phase transitions, where temperature is maintained constant during solid-liquid and liquid-solid phase transition, as described in the original application. As another example, SlipChip can be integrated with on-chip initiation mechanisms for temperature control such as initiation by slipping and mixing.

In some other embodiment, the membrane, matrix, or filter can be impregnated with at least one substance for lysing the cells, spores, or microorganisms in the sample, while drying the sample on the membrane, matrix, or filter by heating and/or absorbing moisture with the desiccant (e.g., such as described in U.S. Pat. Nos. 8,247,176 and 6,645,717, which is incorporated hereby by reference in its entirety). The released nucleic acid or other biomarkers can bind to the membrane matrix or filter, and further washing and elution can be applied.

Volume Quantification

The devices and systems of the invention can be used to quantify volumes of a sample, a reagent, or any useful substance (e.g., any described herein). In particular, quantification of volumes can be used in combination with any of the other devices and methods described herein, such as for sample preservation, sample treatment, sample preparation, and/or sample analysis. In particular, such volume quantification techniques can be useful for screening of special populations (such as newborns, infants, or small animals, e.g., for screening inherited metabolic disorders or lysosomal storage disorders, such as Fabry, Gaucher, Krabbe, Niemann-Pick A/B, and Pompe disease; for screening viral infections, such as HIV or CMV; or for screening other disorders using useful diagnostic markers, such as screening for succinylacetone, acylcarnitines, and amino acids to detect tyrosinemia type I (TYR 1) in newborns or infants), for use with a dried blood spot (DBS) sample (e.g., in combination with one or more sample preservation and/or storage devices and methods, as described herein), for screening metabolites (e.g., for pharmacokinetic, pharmacodynamic, toxicokinetic, or other drug monitoring assessments), for use in clinical trials (e.g., for pharmacokinetic or pharmacodynamic assessment of investigational drugs in clinical trials), and for determining adherence with particular drugs (e.g., for pharmacokinetic, pharmacodynamic, toxicokinetic, or other drug monitoring assessments). In particular embodiments, the test sample is a dried blood spot sample. In one non-limiting embodiment, the device including one or more of a membrane, a bridge, a matrix, a capture region, and/or a desiccant (e.g., a device for sample preservation including one or more of a membrane, a bridge, and/or a desiccant) is used, either with or without a collector, and a blood sample is introduced into the device. Next, the blood sample is dried (either partially or completely, e.g., as described herein). In some embodiments, the blood sample is dried onto a cellulose membrane that is optionally in fluidic communication with a desiccant. Then, the dried blood sample is processed and/or analyzed using one or more useful substances or reagents. Exemplary substances or reagents include a buffer (e.g., a wash buffer or an elution buffer, e.g., PBS containing 0.05% Tween 80 and 0.005% sodium azide, or any described herein), such as those used for screening in DBS technology, including amplification (e.g., PCR); detection of a virus, bacteria, protozoa, and/or helminth (e.g., HIV, hepatitis C virus, hepatitis B virus, hepatitis A virus, herpes simplex virus, rubella, measles, MMR (measles, mumps, and rubella), diphtheria, dengue, tetanus antitoxin, cytomegalovirus, human T-cell leukemia/lymphoma virus I or II, *Mycobacterium leprae, Helicobacter pylori, Brucella* sp, *Treponema pallidum, Toxoplasma gondii, Plasmodium falciparum, Trypanosoma cruzi, Giardia lamblia, Leishmania* spp, *Echinococcus granulosus, Schistosoma haematobium*, or *Brugia malayi*); detection of one or more metabolites (e.g., drug metabolites); detection of one or more analytes (e.g., any described herein, and including androstenedione, amino acids (e.g., arginine (Krebs cycle), histidine/urocanic acid, homocysteine, phenylalanine/tyrosine, and/or tryptophan), apolipoprotein (e.g., A-I or B), cortisol, CD4+ lymphocytes, cholesterol (e.g., including total cholesterol or high-density lipoprotein cholesterol (HDL)), C-reactive protein (CRP), dehydroepiandrosterone (DHEA, including its sulfate ester, DHEA-S), Epstein-Barr virus (EBV) antibodies, estradiol, folate, follicle-stimulating hormone (FSH), glucose, hemoglobin (e.g., including glycosylated Hemoglobin or HbA1c), hepatitis antigen/antibodies (e.g., hepatitis A, B, or C), HIV antibodies, homocysteine, IFNg, IGF-I, IGFBP-2, IGFB-3, IL-1b, IL-6, insulin, leptin, luteinizing hormone (LH), lipoprotein (e.g., (a), B/A-1, or β), prostate-specific antigen (PSA), progesterone, prolactin, retinol, sex hormone binding globulin (SHBG), somatomedin-C, testosterone, transferrin receptor, thyrotropin (TSH), thyroxine (T4), thyroglobulin, triglycerides, triiodothyronine (T3), or TNF (e.g., TNFa)); detection of one or more diagnostic markers for special populations, such as a newborn, a neonate, or an infant (e.g., detection of IgG antibodies for diagnosing infections; detection of succinylacetone, acylcarnitines, and amino acids for diagnosing tyrosinemia type I (TYR 1); detection of medium chain acyl CoA dehydrogenase for diagnosing MCAD deficiency; detection of human chorionic gonadotropin (hCG) for diagnosing Down syndrome; detection of glycated hemoglobin for diagnosing insulin-dependent diabetes; detection of trypsin for diagnosing cystic fibrosis; detection of HIV-specific antibodies and/or of HIV virus in combination with PCR; detection of thyroxine (T4) and thyrotropin (TSH) for diagnosing congenital hypothyroidism; detection of one or more enzymes (e.g., acid α-glucocerebrosidase (ABG), acid α-galactosidase A (GLA), lysosomal acid α-glucosidase (GAA), galactocerebroside α-galactosidase (GALC), or acid sphingomyelinase (ASM)) involved in lysosomal metabolism for diagnosing lysosomal storage disorders (e.g., Pompe, mucopolysaccharidosis (e.g., type I), Fabry, Gaucher, or Niemann-Pick type A/B diseases); for DNA analysis in combination with PCR analysis (e.g., for detecting or diagnosing acetylator polymorphism, alcohol dehydrogenase, alpha 1-antitrypsin, cystic fibrosis, Duchenne/Becker muscular dystrophy, glucose-6-phosphate dehydrogenase, hemoglobinopathy A, hemoglobinopathy S, hemoglobinopathy C, hemoglobinopathy E, D-Punjab, beta-thalassemia, hepatitis B virus, HCMV, HIV-1, HTLV-1, Leber hereditary optic neuropathy, MCAD, PKU, *Plasmodium vivax*, sexual differentiation, or 21-deoxycortisol); for detecting certain antigens (e.g., hepatitis B virus or HIV-1); for detecting certain antibodies (e.g., adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani, leptospira*, measles/mumps/rubella *Mycobacterium leprae, Mycoplasma pneumoniae, Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli* vesicular stomatis virus, *Wuchereria bancrofti*, or yellow fever virus); or screening of one or more drug metabolites or drug analytes (e.g., for pharmacokinetic, pharmacodynamic, toxicokinetic, or other drug monitoring assessments in clinical trials, in clinical monitoring, or in determining adherence with particular drugs, where exemplary drugs include anti-cancer drugs such as everolimus or tacrolimus; acetaminophen; investigational new drugs; or others). Further analytes, DBS assays, and methods are described in McDade et al., Demography 44:899-925 (2007); Cassol et al., J. Clin. Microbiol. 29:667-671 (1991); Bellisaro et al., Clin. Chem. 46:1422-1424 (2000); Williams et al., J. Gerontol. B Psychol. Sci. Soc. Sci. 64B(suppl_1): i131-i136 (2009); Parker et al., J. Clin. Pathol. 52:633-639 (1999); Li et al., Biomed. Chromatograph. 24:49-65 (2010);

and De Jesus et al., Clin. Chem. 55:158-164 (2009), each of which is incorporated herein in its entirety.

Combined Sample Preservation, Sample Treatment, Sample Preparation, and/or Volume Quantification Any of the devices and/or methods herein can be combined to achieve multiplexed sample storage, sample preservation, and/or analysis. For instance, the devices herein for sample preservation and/or volume quantification (e.g., including one or more membranes, bridges, and/or desiccants) can be combined with one or more features provided for devices herein for sample treatment and/or sample analysis (e.g., including one or more capture regions). Accordingly, the devices of the invention encompass those having multiple layers, where at least one layer includes a plurality of first chambers, at least one layer includes one or more capture regions, and at least one or more layer includes a membrane or one or more bridges, where at least one of the plurality of first chamber, at least one of the one or more capture regions, and the membrane or at least one of the one or more bridges are able to be connected by relative movement. In further embodiments, the device includes a layer having at least one second chamber (e.g., a plurality of second chambers), where at least one of the plurality of first chamber, at least one of the one or more capture regions, or the membrane or at least one of the one or more bridges are able to be connected by relative movement to at least one second chamber. In a similar manner, such devices can have additional layers (e.g., any described herein, including one or more intermediate layers, deformable layers, and/or membranes), as well as any component (e.g., autonomous controller, housing, cap, system, or lid, of any described herein) or any modification (e.g., one or more coatings) described herein. Furthermore, the devices can include any useful reagent, substance, or sample (e.g., one or more desiccants, matrices, membranes, or any as described herein), and use of the device of any useful method (e.g., as described herein).

Kits for Sample Preservation, Sample Treatment, Sample Preparation, and/or Volume Quantification Any of the devices and/or methods herein can be provided with additional components to facilitate sample storage, sample preservation, and/or analysis. Further exemplary components include a collector (e.g., for collection fluid samples (e.g., blood, saliva, urine, sputum, feces, or tissue, or any described herein), such as a lancet (e.g., a Safety-Lancet, available from SARSTEDT, Nümbrecht, Germany), a capillary (e.g., a Microvette® capillary or a Multivette® capillary, available from SARSTEDT), a needle (e.g., a safety needle in combination with a syringe, such as an S-Monovette® system available from SARSTEDT), a syringe, a swab, a sample tube (e.g., a Monovette® tube, available from SARSTEDT), or a microtube), one or more reagents (e.g., any described herein, including those useful for collecting and/or preserving blood samples, such as heparin, citrate, a gel (e.g., a polyacrylic ester gel), a clotting activator (e.g., a particle, such as silicate particles), or EDTA and those useful for binding, reacting, or preserving one or more analytes of interest, such as any described herein), and/or one or more controls (e.g., one or more standard controls for an analyte of interest and/or one or more negative controls, such as buffer). The kit can optionally include instructions for use, such as providing step-by-step instructions for any method described herein.

Pressure Capping

The systems of the invention can include one more lids or caps to generating pressure for filling a device.

Figure 22:
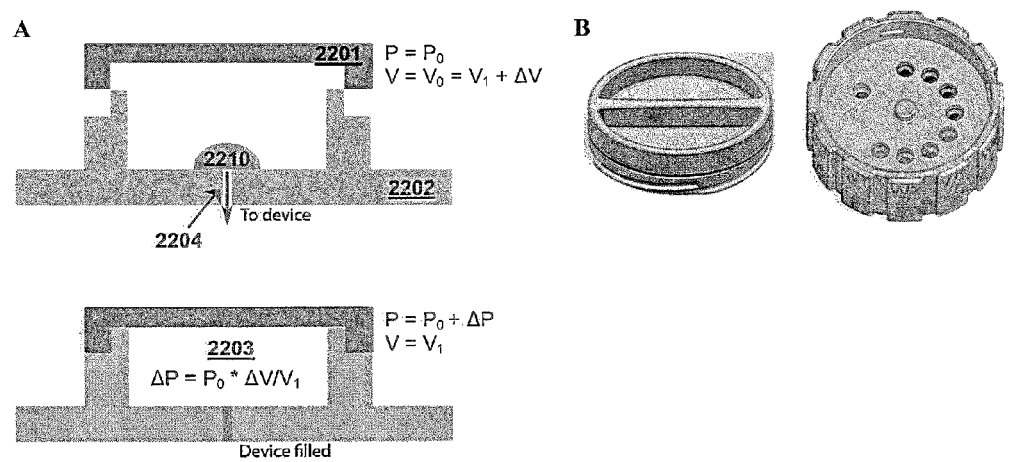
FIGS. 22A-22B provide a proposed system for generating pressure for filling a device. A: The housing system includes a lid 2201 for a device 2202 having a through-hole 2204. Provided are schemes of an open or partially open system (top of FIG. 22A) and a completely closed system (bottom of FIG. 22A). B: To effect this system, the housing system can include a pressurization lid (left) that can be used to apply both positive and negative pressure to the system.

As shown in FIG. 22, the housing system can include a lid 2201 for a device 2202 having a through-hole 2204. In an open or partially open system (top of FIG. 22A), the relevant volume is $V=V_0=V_1+\Delta V$, where $\Delta V$ encompasses any volume difference between a completely closed system (complete closure of the lid) and an open system (without a lid) or a partially open system (partial closure of the lid). In a completely closed system (bottom of FIG. 22A), the relevant volume is $V=V_1$, where $V_1$ is the volume of the cavity 2203 when completely enclosed. The generated pressure P is commensurate with these changes in volume V and presumably the force applied during closing.

Figure 32:
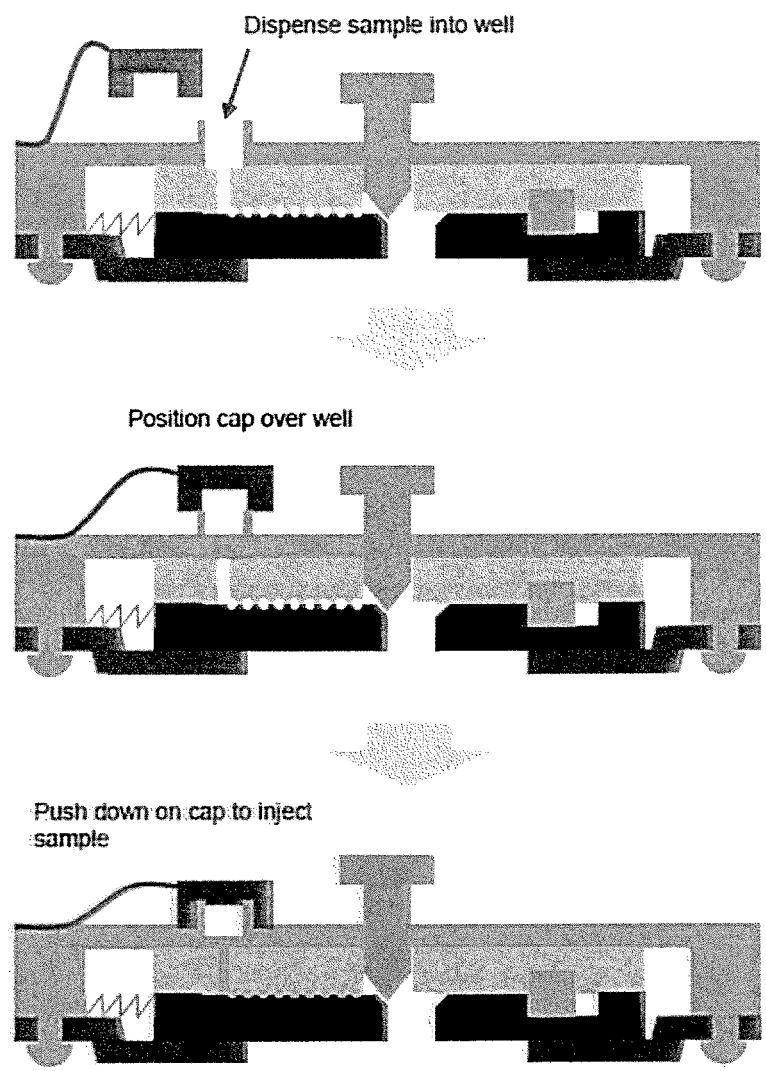
FIG. 32 is an exemplary scheme showing a proposed system for generating pressure for filling a device. In particular, a sample is dispensed into a well, a lid (or cap) is positioned over the well, and then the lid is closed to inject the sample into the device.
Figure 33A:
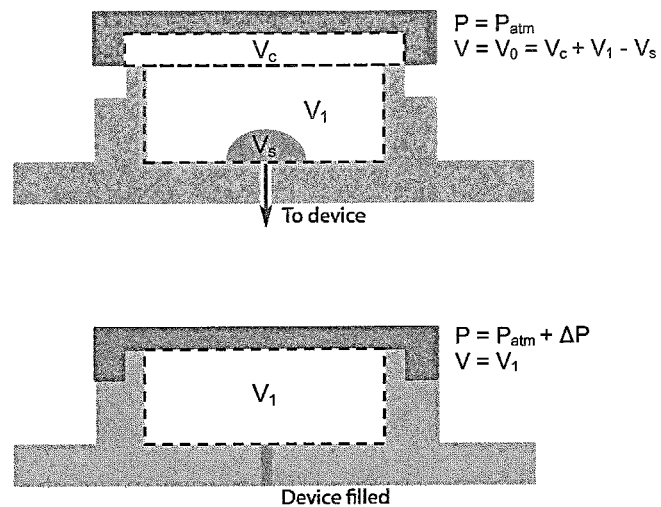
FIGS. 33A-33C provide a system for generating pressure for filling a device. A: Similar to the system of FIGS. 22A-22B, the housing system includes a lid for a device 2 having a through-hole. In a partially open system (top of FIG. 33A), the relevant volume is $V=V_0=V_c+V_1-V_s$, where $V_c$ is the volume of the lid (as shown in FIG. 33A), $V_1$ is the volume of the cavity when completely enclosed, and $V_s$ is the volume encompassed by the sample. In a completely closed system (bottom of FIG. 33A), the relevant volume is $V=V_1$, where $V_1$ is the volume of the cavity when completely enclosed. The generated pressure P is commensurate with these changes in volume V. In an open or partially open system, generated pressure $P=P_{atm}$, which is not sufficient to drive sample 2210 to the device. In a closed system, generated pressure $P=P_{atm}+\Delta P$, where $\Delta P$ reflects the change in volume upon complete closure of the lid. Thus, the volume difference induced by closing the lid generates additional pressure used to fill the device. B: To effect this system, the housing system can include a pressurization lid (left) that can be used to apply both positive and negative pressure to the system. An exemplary system was implemented for a SlipChip device and successfully executed by an untrained six-year old child. C: Provided are step-by-step instructions for forming 1600 nL compartments or droplets within an autonomous SlipChip device.
Figure 33B:
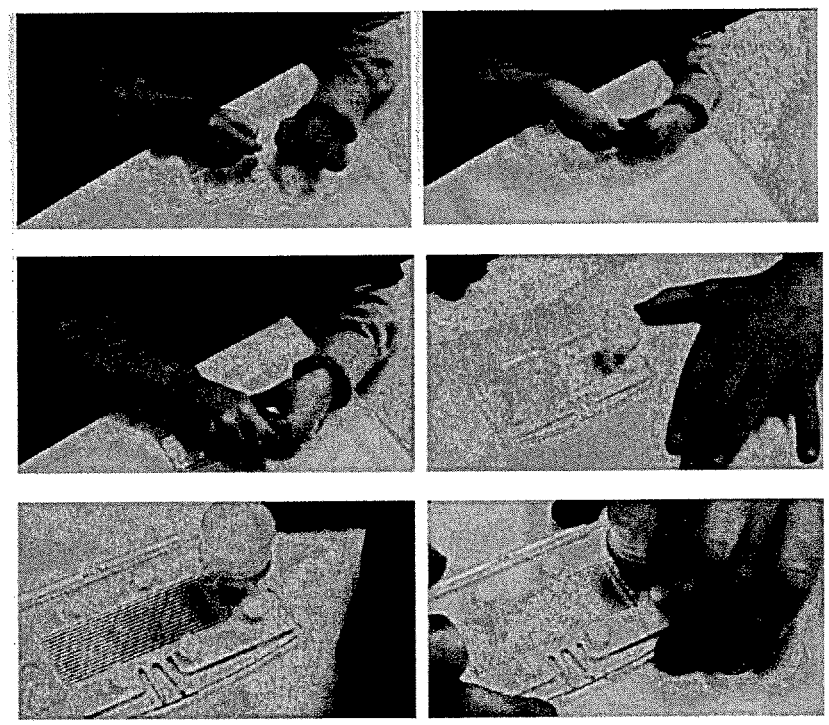
Figure 33C:
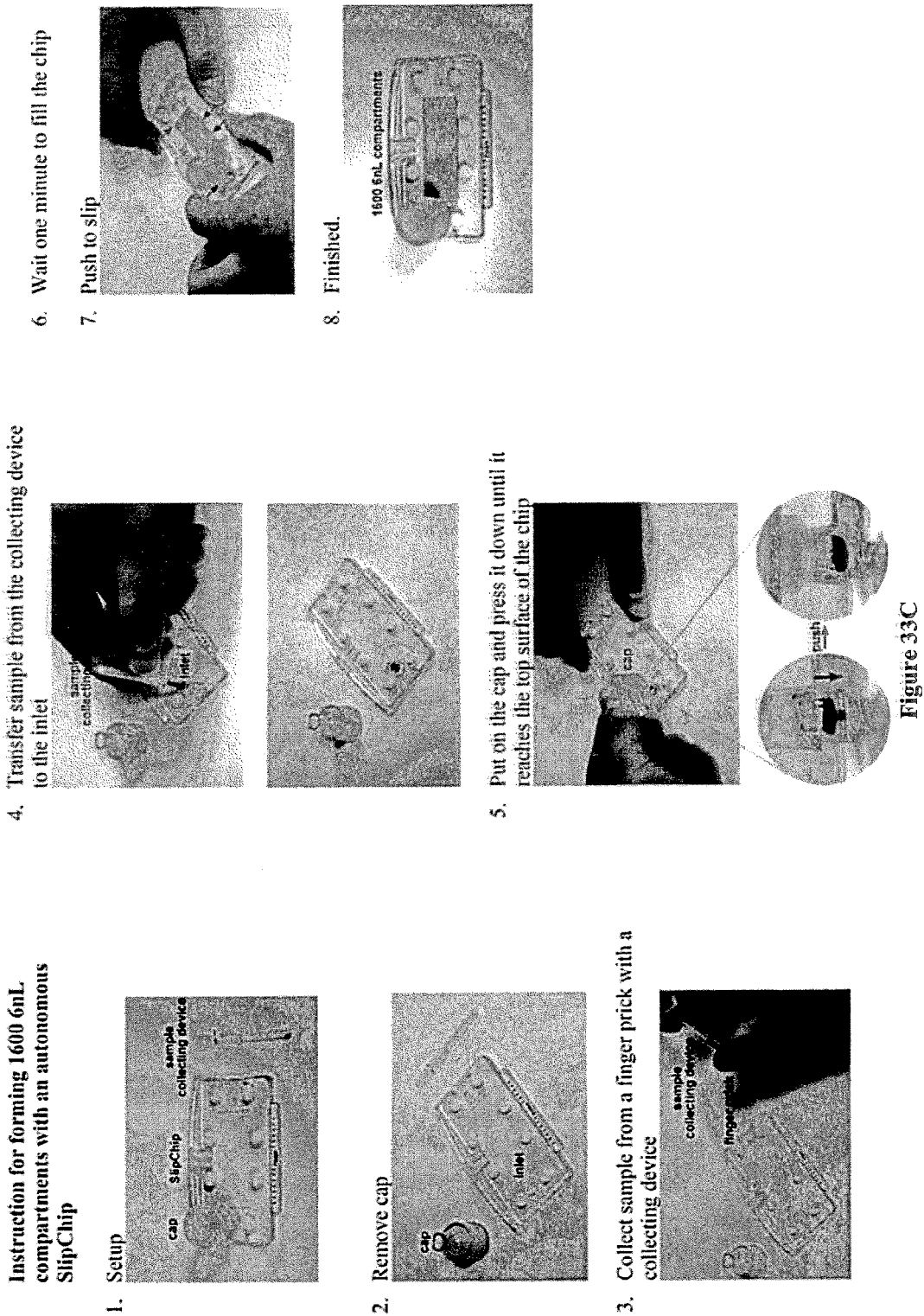

In an open or partially open system, generated pressure $P=P_0$, which is not sufficient to drive sample 2210 to the device. In a closed system, generated pressure $P=P_0+\Delta P$, where $\Delta P=P_0*\Delta V/V_1$. Thus, the volume difference induced by closing the lid generates additional pressure used to fill the device. A positive pressure can be created by pushing rigid cap or lid (FIG. 22B, right) on to the on-chip reservoir or housing system. The cap or lid can be designed so that it cannot be 'half on' but and only be 'fully off' or 'full-on' (FIG. 32). Attaching the cap applies a positive pressure to the well of around 50 mBar which is generated by compressing the gas (e.g., air) in the well. It may be optimal to make the well quite large (conical shape) so that variations in the sample volume do not have a significant effect on the pressure that is generated. (FIGS. 33A-33B, Example 8).

Sample Loading

Loading of a substance may be performed by a number of methods, as described herein. Loading may be performed either to fill the ducts and areas of the device, for example by designing the outlets to increase flow resistance when the substance reaches the outlets. This approach is valuable for volume-limited samples or to flow the excess volume through the outlets, while optionally capturing analyte from the substance. Analytes can be essentially any discrete material which can be flowed through a microscale system. Analyte capture may be accomplished for example by preloading the areas of the device with capture elements that are trapped in the areas (such as particles, beads or gels, retained within areas via magnetic forces or by geometry or with relative sizes of beads and ducts or with a membrane), thus whatever absorbs, adsorbs, or reacts with these beads or gels is also trapped. These areas will then retain an amount or component or analyte of the substances they are exposed to. Retaining of the sample can also be achieved by functionalization of the surface of an area, deposition of a material on an area, attaching a monomer in a polymerization reaction (such as peptide or DNA synthesis) to an area, etc.

In particular embodiments, the loading apparatus loads a reagent, a sample, or a fluid into a device by using an external component or combining one or multiple on-chip components to create either positive or negative pressure. Such pressure can result in a pressure gradient to pump one or multiple reagents, samples, or fluids into a single-layered or multi-layered device. The loading apparatus can include any useful on-chip, off-chip, or a combination of on-chip and off-chip apparatuses that can create a pressure gradient for loading a reagent, a sample, or a fluid into a device. The disclosed apparatus can include a rigid structure, a flexible structure, or a porous structure, as well as other components that can create a pressure gradient in a device.

A loading apparatus can create positive pressure and/or negative pressure to effect fluid flow. Accordingly, apparatuses can be combined to create positive and negative pressure at separate positions in a device for creating any useful pressure gradient. Such apparatuses can control the magnitude of positive or negative pressures or the magnitude of the pressure gradient.

In one non-limiting embodiment, the device includes a receiving chamber for controlling the volume of a reaction fluid and/or a lubricant, if present, in the first and/or second chambers. In further embodiments, the loading apparatus includes a rigid structure to create positive pressure. By designing the rigid structure appropriately, the magnitude of this positive pressure can be controlled. In this method, a modified pipette tip and a stopper is used to load the device (FIG. 30A). When the tip was immersed into a solution to be loaded, pulling the stopper created an instant vacuum that pushed the solution into the tip (FIG. 30B). Due to capillary pressure, a certain amount of solution was contained in the tip (FIG. 30C), which was then inserted into an inlet (FIG. 30D). Pushing back in the stopper first sealed the pipette tip and then a positive pressure was created to drive the solution into the connected fluidic path to load the chip by dead-end filling. Increasing the created pressure (e.g., by simply increasing the depth the stopper can be pushed in) increases the loading speed (FIG. 30E). We designed the stopper such that a controlled volume is compressed, and loading could be finished in one minute without leaking. We developed a SlipChip that an untrained person can use to run a color-change reaction in 5 minutes (FIG. 30F). Optionally, to avoid trapping of air bubble, a female luer lock at the inlet may be incorporated to contain lubricant oil that covers the inlet orifice (FIG. 30D). Optionally, the device can be clamped together with magnets. Magnetic force is proportional to the size of magnets as well as their grades. Two sets of N42 magnets, ⅛ inch (D) by ¼ inch (W) by ½ inch in size, provided enough force to hold the chip (1.5 inches (W) by 2 inches (L)) in close contact, not causing leak during solution loading. The magnets were placed along the width of the chip at the edge so that they did not block the view of reaction wells (FIG. 30G).

Figure 30:
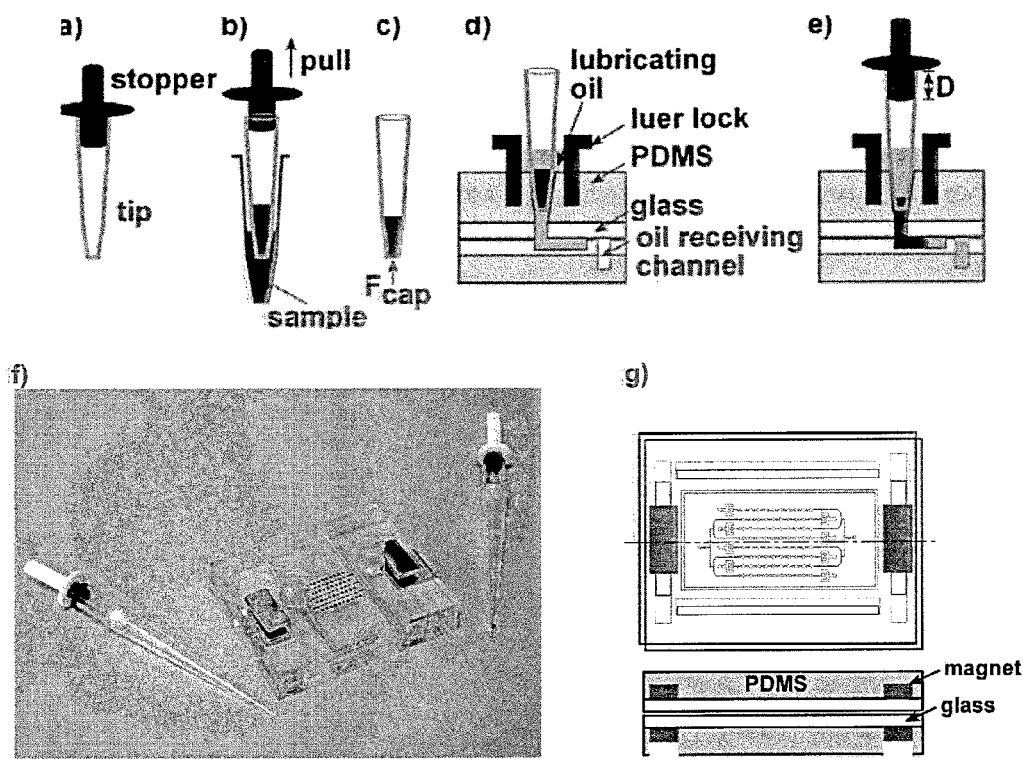
FIGS. 30A-30G provides exemplary schemes for loading a fluid into a device by dead-end filling. A-C: Loading can include use of a tip and a stopper to obtain a sample, where capillary force ($F_{cap}$) retains the sample within the tip. D: The tip can be interfaced with a device filled with a lubricant and having a luer lock and a receiving chamber (e.g., an oil receiving channel). Optionally, a barrier layer (e.g., a lubricant) is provided between the tip and the luer lock to reduce contamination of the sample, to reduce evaporation of the sample, and/or to minimize air bubble formation within the device. E: Insertion of the tip into the luer lock and/or depression of the stopper results in a pressure difference that promotes flow of the sample into the device, as well as displacement of the lubricant into the receiving chamber. F: A SlipChip was used to perform a color change reaction with the components described in FIGS. 30A-30E. G: Magnets can be used to clamp the layers of a SlipChip, where magnets can be embedded in the top layer and additional magnets can be inserted into the bottom layer during assembly.
Figure 31:
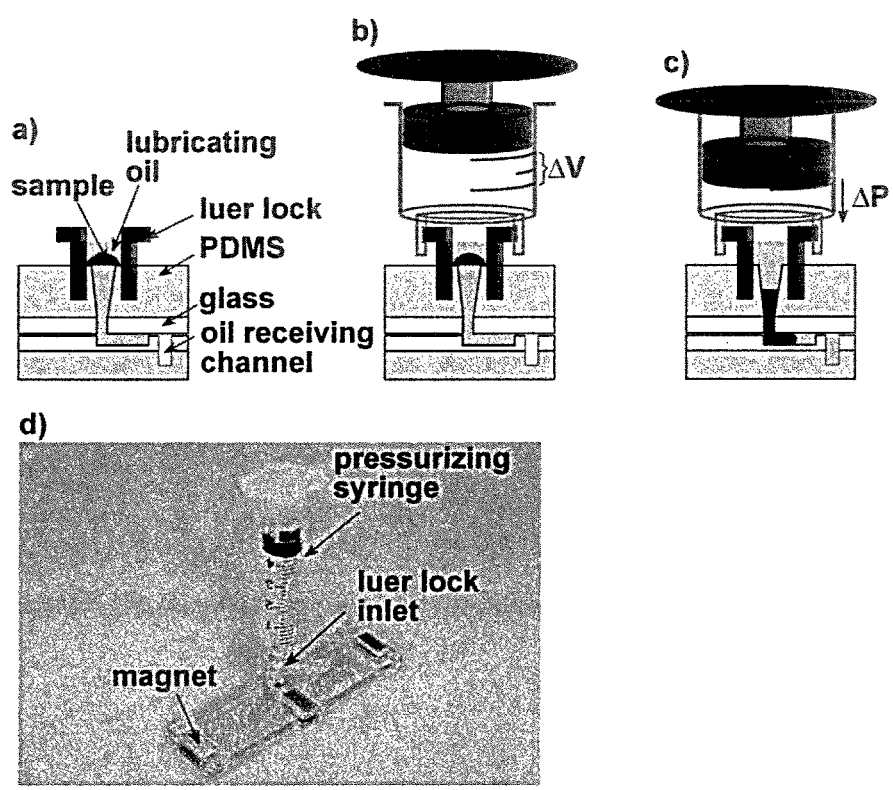
FIGS. 31A-31D provides additional exemplary schemes for loading a fluid into a device by dead-end filling using a modified syringe. A: A sample is pipetted into the inlet reservoir, where the presence of a lubricant reduces contamination of the sample, reduces evaporation of the sample, and/or minimizes air bubble formation within the device. B: A modified syringe including a certain volume is connected to the device via a luer lock. C and D: Pushing the plunger compressed the confined air by $\Delta V$ and created loading pressure $\Delta P$ for automatic dead-end filling of the device, as shown in the scheme (C) and photograph (D).

Similar to the apparatus described in above in FIG. 30, a modified syringe can be used to load solution into a SlipChip (FIG. 31A-31D). A controlled positive pressure is created by decreasing the volume in the closed cavity in the syringe. By pushing down the plunger to a pre-determined stroke, a pre-determined positive pressure can be created and initiate loading.

In dead-end filling, a gap between two layers connects the main filling channels or chambers to the outlets. In this way, the filling liquid (e.g., a sample, a reagent, or any substance described herein) is confined in the channels or chambers, while the immiscible phase (e.g., a lubricant or an oil, as described herein) can be evacuated from the channels to the outlets through the gap. In particular, the devices and methods presented here to control pressure and filing can be used in other applications other than just filling channels. These devices and methods can be used to control pressure to open and close valves (e.g., capillary or hydrophobic valves, or any described herein). Exemplary valves include a hydrophobic valve having a structure (e.g., a decrease in a hydrophobic channel cross-section) that prevents or hinders aqueous fluid flow; a capillary valve having a structure (e.g., an increase in a channel cross-section) that exerts a capillary pressure barrier to prevent or hinder fluid flow; as well as those described in mmadou.eng.uci.edu/research_cd.html, which is incorporated herein by reference. The devices and methods described herein can also be used to control flow rate, such as by considering both applied pressure and flow resistance in the device.

Figure 34:
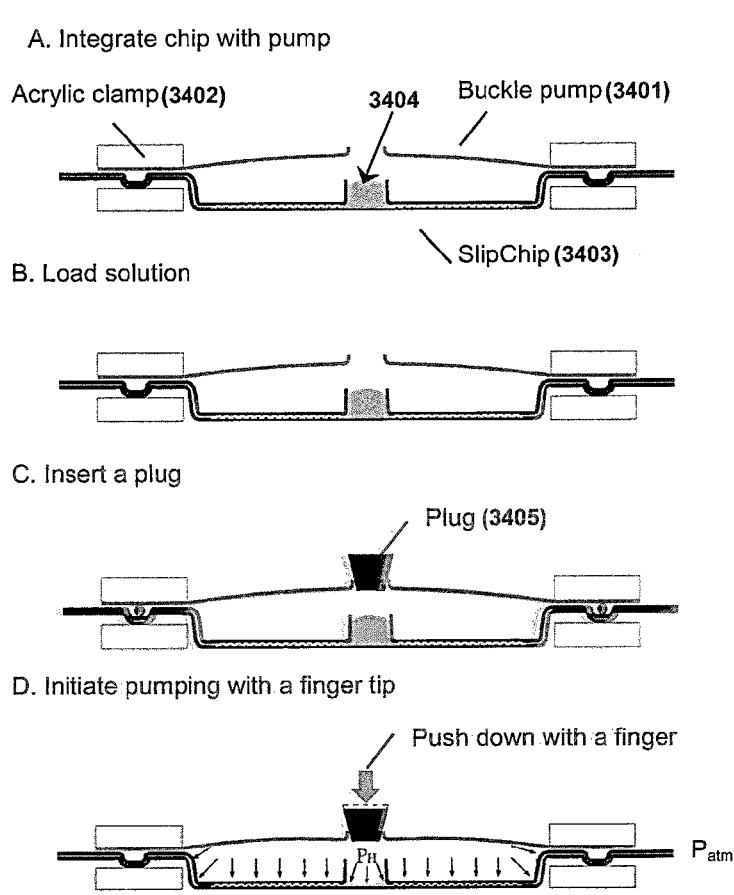
FIGS. 34A-34E provide exemplary illustrations of a thin-film buckle pump. A: A thin-film SlipChip device 3403 can be integrated with a thin-film buckle pump 3401 by using an acrylic clamp 3402. B: A sample 3403 can be loaded through an opening of the buckle pump. C: The cavity can be sealed by inserting a plug 3405. D: Pumping can be initiated by pushing down the buckle pump with a finger tip. E: Provided are a sequence of frames taken from a video clip showing the function of a buckle pump.

In another non-limiting embodiment, the loading apparatus includes a flexible structure to create a magnitude controlled positive pressure. A positive pressure can be created by using a flexible structure; such as using a thin plastic film to serve as a buckle pump (FIG. 34). By using a curved thin plastic film, the curved 3D structure becomes mechanically unstable toward the centre of the curvature. A buckle motion can be easily created by applying an external force, such as a finger tip or a lever. FIG. 34A-34D are conceptual illustrations of integrating the buckle pump 3401 and the SlipChip 3403. A sealed cavity can be created by placing a buckle pump on top of the SlipChip. A positive pressure can be created inside the cavity by applying a force on the buckle pump (FIG. 34D). This concept was verified by using a thin-film buckle pump in combination with a thin-film device. A positive pressure can be created by using a finger tip to deform the thin-film buckle pump, thus creating a sealed cavity between the thin-film buckle pump and the SlipChip. FIG. 34E shows an integrated device by using this apparatus. The geometry of the flexible structure is not limited to a curved structure, and all deformable structures, including a flat thin plastic film, can create similar pumping mechanism by introducing a deformation, should be included.

In one non-limiting embodiment, the loading apparatus includes a rigid structure and a flexible structure to create a magnitude controlled positive pressure. Controlled magnitude of positive pressure can be created by combing a flexible structure against a rigid structure (see, e.g., FIG. 35). The flexible structure can be deformed by moving a rigid structure to first create a sealed cavity between the rigid structure and the device. Further deformation by moving the rigid structure (as in FIG. 35B) can continue to decrease the volume in the sealed cavity, thus creating a positive pressure for pumping the sample into the device. The flexible structure can be attached to the rigid structure (FIG. 35) or on the SlipChip (FIG. 37).

Figure 35:
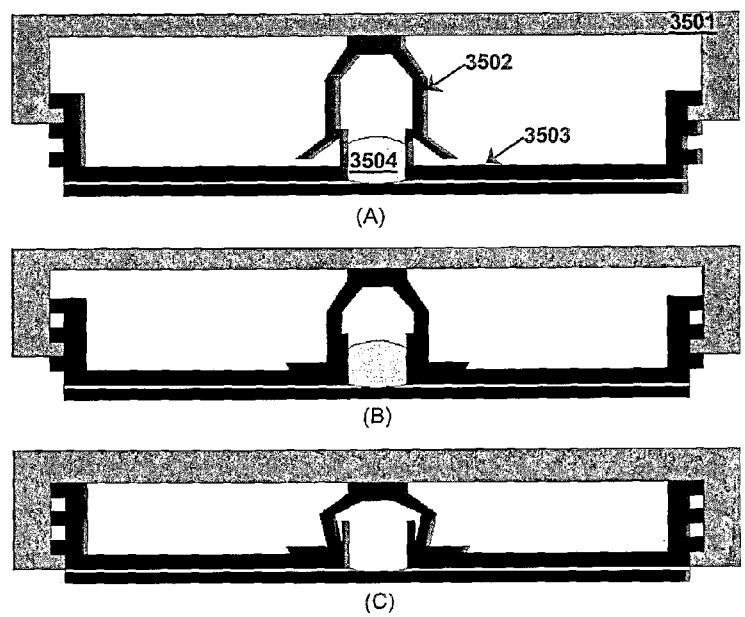
FIGS. 35A-35C provide exemplary illustrations of an apparatus for creating a positive pressure by combining a rigid cap 3501 with an attached flexible pumping cup 3502. A: Closure of the cap brings the pumping cup in contact with the SlipChip 3503. B: A sealed cavity is created by rotating the lid down against the screws. C: Positive pressure is created by further rotating the lid, thereby transporting the loaded solution in the reservoir 3504 into the SlipChip device.
Figure 36:
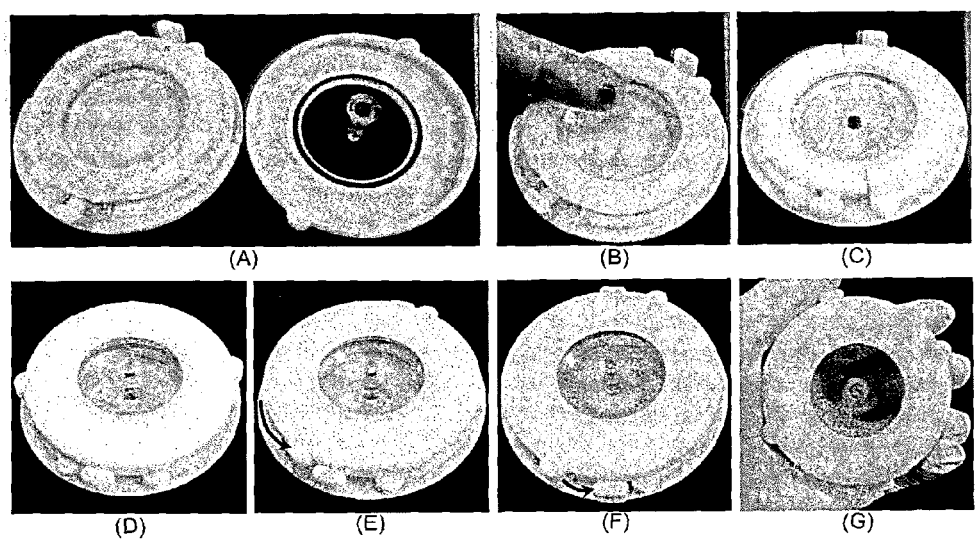
FIGS. 36A-36G are photographs showing an exemplary operation sequence of a SlipChip loading apparatus using a rigid cap attached to a pumping cup. A: The system includes two components: a cap with a pumping cup (right) and a SlipChip device (left). B and C: A sample (e.g., a patient's sample) is introduced in the reservoir on thin-film SlipChip device. D: The cap is closed to protect sample with the pumping cup. E: Pumping and loading are initiated by rotating (arrow) the cap onto the SlipChip. F: Relative movement (e.g., by slipping, as indicated by slide) results in creating a digital droplet (e.g., microdroplet) array in the device. G: The SlipChip device can be removed from the base for further analysis, e.g., quantitative detection.

FIG. 35 is an illustration of combining a flexible structure (pumping cup 3502) and a rigid structure (cap 3501) to control the magnitude of the created positive pressure. The cap and the SlipChip (3503) have screws against each other that allow users to bring the pumping cup to contact the device (A), seal the cavity (B), and then create a positive pressure (C). Each step is controlled by the number of pitches that the cap screwed onto the SlipChip, and the magnitude of positive pressure can be controlled. The sealed cavity is created by the deformed pumping cup against the SlipChip, and the positive pressure is created by further deformation of the pumping cup. FIG. 36 shows an integrated device that using this apparatus to load solution into a thin-film SlipChip.

Figure 37:
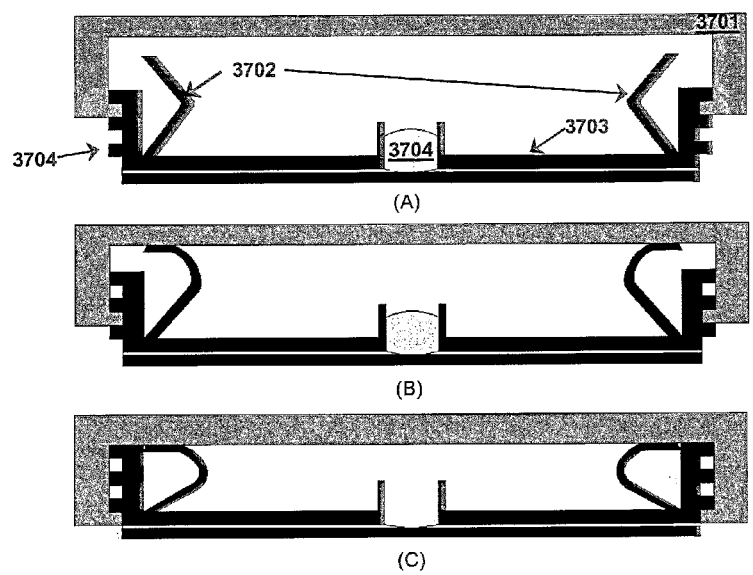
FIGS. 37A-37C provides exemplary, conceptual illustrations of an apparatus for creating a positive pressure by combining a rigid cap 3701 and a flexible pumping cup 3702 on a SlipChip device 3703. A: Closing the cap results in contact with the pumping cup. B: A sealed cavity is created by rotating the lid down against the screws 3704. C: Positive pressure is created by further rotating the cap, thereby transporting the loaded solution in reservoir 3704 into the SlipChip device.

Following a similar concept in FIG. 37, a positive pressure can also be created by attaching a flexible structure on the SlipChip. FIG. 37 illustrates an apparatus using a rigid cap 3701 and a pumping cup 3702 attached to the SlipChip 3703. A sealed cavity can be created by closing the cap 3701 against the screws 3704 on the SlipChip 3703 to bring the cap in contact with the pumping cup 3702 (A), create a sealed cavity between the cap 3701 and the SlipChip 3703 (B), and create a positive pressure by decrease volume in the sealed cavity (C). The loaded solution (3704) in the on-chip reservoir is driven into the SlipChip.

Figure 38:
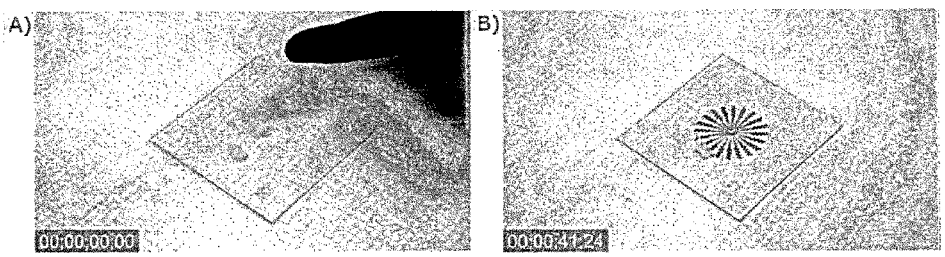
FIGS. 38A-38B provide frames taken from a video showing the vacuum filling of a SlipChip device. A: The device was loaded with a 0.1M solution of $Fe(SCN)_3$ from the tip of a finger onto the sample inlet. The timecode starts as the finger approaches the device. B: The device was completely filled in less than 42 seconds. The sample was placed on the inlet, and a 0.1 atm pressure difference was applied via a syringe connected to the device by Teflon® tubing and a PDMS gasket.

In one non-limiting embodiment, the loading apparatus includes a rigid structure to create a magnitude controlled negative pressure. A gas impermeable sealant is applied between the layers of the device to create a closed cavity for the lubricant. A negative pressure can be created by increasing the volume of a sealed cavity. In this manner, a negative pressure is applied to the oil lubrication layer, thus creating a pressure gradient in the device between the loading apparatus and chambers. FIG. 38 shows an apparatus to load solution into the SlipChip by using a modified syringe (connected to the tubing). A circular channel was designed around the chambers for applying silicone grease to serve as a gasket. Thus, a closed oil cavity is created between the layers, and the only connections to outside world are the solution reservoir and the negative pressure source. Once a negative pressure is provided from the modified syringe (by pulling the plunger with a predefined stroke) solution will be drawn into the chambers in the device. This apparatus works by first reducing the gap between the layers of the device before loading followed by drawing the solution into chambers with created vacuum.

In another non-limiting embodiment, the loading apparatus includes a flexible structure to create a magnitude controlled negative pressure. The flexible structures described herein are not limited to creating positive pressure. For example, a buckle pump can be connected to a device and be deformed by applying an external force. Once releasing the external force, a negative pressure can be created when the flexible buckle pump restores to its original shape. In this manner, a pressure gradient can be created to draw a sample, reagent, or fluid into the device from a solution reservoir.

In one non-limiting embodiment, the loading apparatus includes a rigid structure and a flexible structure to create a magnitude controlled negative pressure. For example, a pumping cup can serve as a sucking cup to create a negative pressure. By increase the cavity in the sealed cavity between the rigid cap and the device (e.g., by simply rotating the cap up from the device), a negative pressure can be applied to the device.

In one non-limiting embodiment, the loading apparatus includes a porous structure to create a magnitude controlled negative pressure. Negative pressure can be created by applying or connecting a porous material to the lubricant between the layers of the device (see, e.g., FIG. 39). A porous material can serve as an absorbent for the lubricant and create a pressure gradient in the device from the solution reservoir. This filling apparatus is distinguished from the previously described apparatuses in that the negative pressure (suction) is created by withdrawing lubricant away from the sealed cavity between layers. The magnitude of negative pressure is controlled to be equal or higher than the pressure necessary to draw solution into the device but to be less than the sealing pressure for preventing leakage of solutions. Negative pressure can be created directly by an oleophilic porous material (for example, a sponge), where suction is created by the lubricant wicking inside the sponge forcing aqueous solution flow into the SlipChip; or by an elastic porous material, where suction is introduced by an increase in volume of the pores in the porous material.

FIG. 39A illustrates the apparatus using a porous material to create negative pressure for loading solutions with dead-end filling. The porous material can be oleophobic, oleophilic, or hydrophilic. Using a hydrophobic porous material, another type of dead-end filling can be achieved. The solution been drawn into the SlipChip device can be stopped as soon as reaching the interface of the porous material since a hydrophobic interface provides a low affinity interface for aqueous solutions (FIG. 39B). FIG. 39C shows a SlipChip device loaded by using an apparatus with embedded porous material.

Automated Analysis with Device

Figure 40:
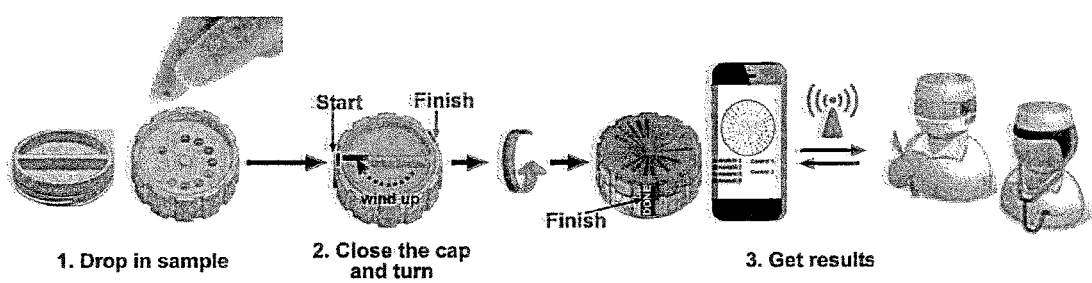
FIG. 40 is a scheme showing sample processing in a device of the invention, use of an automated system to prepare and process the sample, and use of an external cellular phone to analyze the results and transmit the results.

The invention can further include a housing system surrounding the device, where the housing system includes an access port for inserting a sample, and a cap or lid for enclosing the housing system. As described herein, closing the cap results in introducing the sample into the device. To achieve automation, the cap or housing system can include one or more assemblies (e.g., an autonomous controller, such as any described herein) to effect relative movement of the first, second, and/or intermediate layers upon closing the cap. Such exemplary assembles are described herein and can include linear or rotational actuation mechanisms. As shown in FIG. 40, automation can be realized by using a cap to wind up the device, which results in relative movement of the layers for sample preparation. Further autonomous controllers are described herein (e.g., see FIGS. 45-48 and related text).

Cell Phone Detection

The systems of the invention can further includes a detection system for detecting and/or relaying the results of the analysis. As shown in FIG. 40, a cell phone (or equivalent hand held camera) can be used to image a pattern of dots on a SlipChip device, to automatically process the photograph for analysis, and to autonomously send and receive results. To allow for a high level of medical care, results can be transmitted to reference laboratories or remote physicians without user effort. In some embodiments, the device and the cell phone can be provided together for maximum utility in the field.

Integration for Devices and Systems

The devices and systems of the invention can be integrated with other devices to allow multistep processes. For example, the sample preparation modules can be included in the device by exploiting the modularity of SlipChip devices, in order to prepare the sample before storage. Examples include but are not limited to devices for multistep protocols for nucleic acid extraction and filtration elements to separate plasma from whole blood using membranes and/or integrated filtration elements such as geometrical features in the device (for example, restrictions or a gap between the plates). The device can include further optional components useful for use, as described herein.

A component for precise volume quantification can be combined with the device or system of the invention. The total collected volume can be quantified digitally by counting the number of wells that have been filled (see FIG. 26C). Sequential filling, as described herein, can be used to ensure that the wells are filled one by one, so the quantification becomes trivial.

A plasma separation component can be easily integrated with the device or system of the invention. A membrane for plasma separation can be integrated as a top layer for any device described herein. The pressure needed to filter whole blood through a membrane (~10-50 mm Hg) is enough to load the SlipChip device. Preliminary data show that plasma separation and device filling can be achieved at the same time with a single pressure source. This pressure source can be an external device (for example, a pipettor or a glued syringe) or integrated in the device itself (see, e.g., FIG. 22A).

Some of these devices can allow multiplexed, multi-purpose stabilization. Each sample can be split or partitioned into multiple parts and preserved dry in order to store a different analyte (including but not limited to proteins, DNA, RNA). Drying times for digitized volumes (e.g., as in FIG. 29) are considerably shorter than those for bulk solution, so this technology can allow for stabilization of very fragile biomarkers (e.g., HCV viral RNA). Multiple preservation matrices (e.g., any described herein) for the same sample or analyte can also be used (e.g. different chemistries to preserve RNA and protein, or different chemistries just to preserve RNA in different ways).

Some of these devices can enable the collection of several samples in the same device. Parallel collection of several independent samples at the same time can be achieved by using a commensurate array of inlets (see, e.g., FIG. 26A). Contamination-free collection of samples at different timepoints can be achieved by using incommensurate inlets (see, e.g., FIG. 26B).

For any of the devices or systems herein, a sample recovery component can be included. Recovery can be achieved by re-hydration, where a solution (e.g., water or a buffer) can be injected into the device and used to redisperse the dried sample. At first, an immiscible fluid (e.g., such as an oil, a lubricant, or an immiscible aqueous solution) may or may not be injected in the chambers, followed by a known water volume (which may be the same as the starting volume of the preserved solution). Recovery is possible by reinjecting a solution (e.g., water or a buffer) to rehydrate the sample. Applying external pressure, applying an external low vacuum, or exploiting capillary pressure can allow the extraction of the liquid from the device. Recovery can include full or partial recovery, as described herein.

Figure 27:
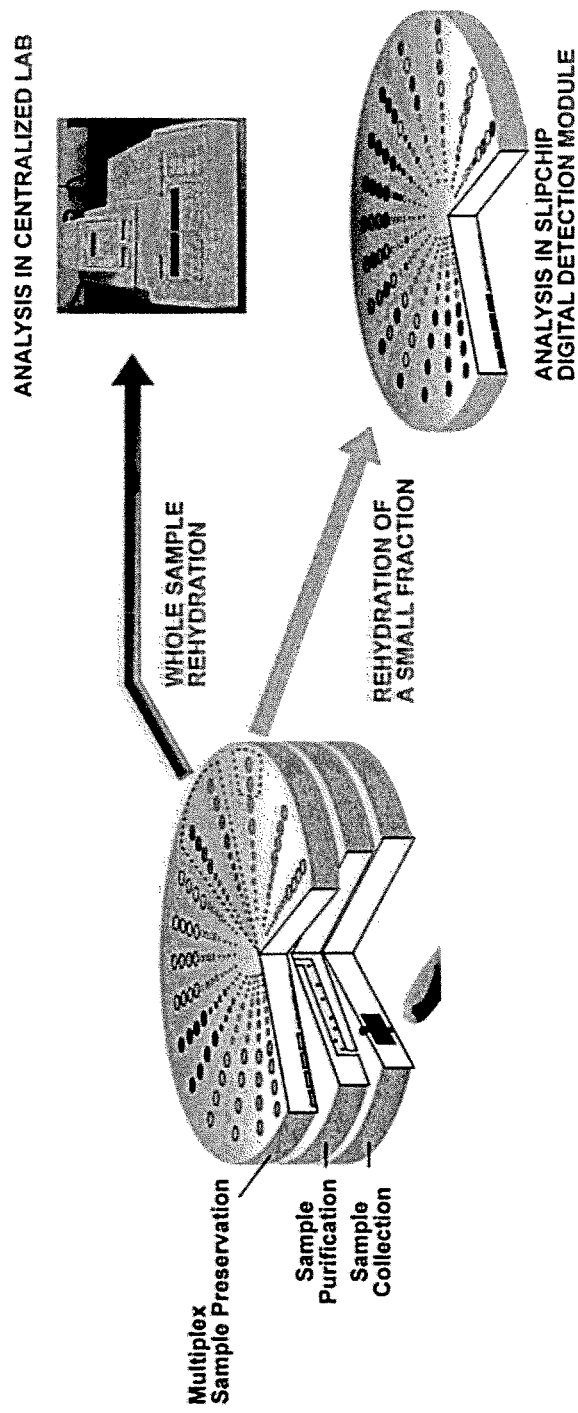
FIG. 27 provides an exemplary scheme for rehydration of a whole sample or rehydration of a small fraction of a sample for analysis in a centralized laboratory and/or on-site.
Figure 28:
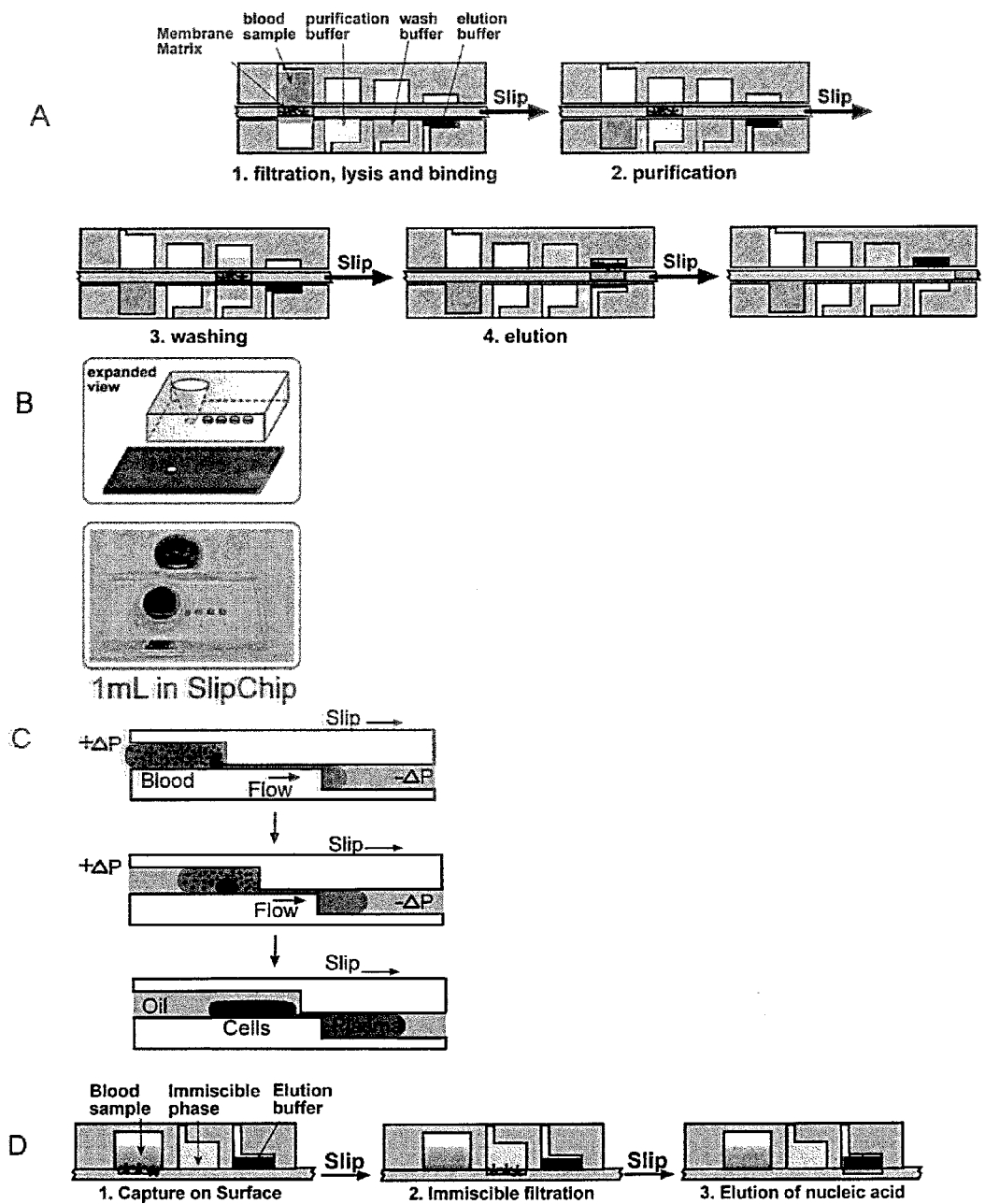
FIGS. 28A-28D provide exemplary uses for sample preparation with SlipChip. A: When the sample is a blood sample (e.g., a whole blood sample), the SlipChip can be designed to include steps for filtering the blood sample, as well as purifying, washing, and eluting the analytes captured in the capture region. These analysis steps can be performed by relative movement of the top and bottom layers of a device. B: SlipChip can also be designed to determine preliminary results for nucleic acid extraction in large volumes (e.g., more than or equal to 1 mL samples. C: SlipChip can be designed to include one or more chambers (e.g., channels of varying cross-sectional dimensions) to promote rapid separation of a sample (e.g., a blood sample) and nucleic acid extraction by membrane filtering and elution. D: SlipChip can be designed to include various analysis steps, including analyte capture, immiscible filtration, and elution.
Figure 29:
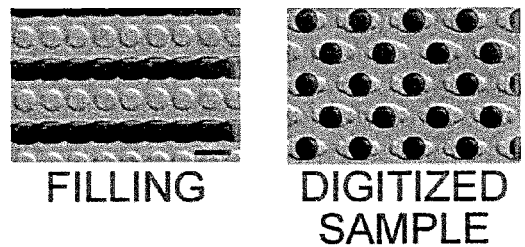
FIG. 29 provides microphotographs showing filling of a SlipChip (left) and digitization via relative movement (e.g., by slipping) after filling. Such digitized samples (or compartmentalized samples or aliquots) can be further processed, transported, analyzed, and/or stored, as described herein.

For any of the devices or systems herein, sample analysis can be performed either on-site (for example, using the SlipChip detection modules) or off-site (for example in a central facility) (see, e.g., FIG. 27). For on-site analysis, a partial recovery may be sufficient (e.g., a total volume of few µL), and the sample can be directly transferred to a detection module for purposes such as digital nucleic acid or protein detection. For analysis in a central facility, a total recovery (e.g., 10-50 µL) may be necessary. In this case, all the chambers containing preserved sample can be rehydrated at the same time, and the total recovered volume can be collected for further analysis.

Any of the devices or systems herein can be integrated with a pressurization apparatus (e.g., any described herein), a loading apparatus (e.g., any described herein), an injection port for serial and/or sequential filling of the chamber(s), a heating element, an on-chip lysis component, or molecular recognition module. For instance, the device can be integrated temperature control methods suitable for sample lysis for nucleic acid extraction, such as for example, temperature control methods based on simple phase transitions, where temperature is maintained constant during solid-liquid and liquid-solid phase transition, as described in the original application. As another example, the device can be integrated with on-chip initiation mechanisms for temperature control, such as initiation by relative movement (e.g., slipping) and mixing.

Any of the devices or systems herein can include electrically conductive material (e.g., one or more electrodes, including arrays thereof). Such electrodes and arrays may be useful for conducting electrochemical reactions for detection, separation (e.g., electrophoretic separation), transport, and/or synthesis. In some embodiments, one or more electrodes are arranged to allow for connection or disconnection upon relative movement of the layers.

The device and methods of the invention may also include a detector, such as an imaging or sensor components to record and/or measure reactions within the device (e.g., by optical, x-ray, MALDI, FP/FCS, FCS, fluorometric, colorimetric, chemiluminescence, bioluminescence, scattering, surface plasmon resonance, electrochemical, electrophoresis, lasers, mass spectrometry, Raman spectrometry, FLIPR™ (Molecular Devices), etc. measurements). Examples of such detectors and imaging devices can be found in U.S. Pub. No. 2009-0010804 and Int. Pub. No. WO 2008/002267, both of which are incorporated herein by reference. The detector may be any detector suitable to detect the may be selected from the group consisting of: a web camera, a digital camera, a digital camera in a mobile phone and a video camera, as described in Int. Pub. No. WO 2008/002267, incorporated by reference herein in its entirety. Alternatively, the detector can be a camera or imaging device which has adequate lighting and resolution for spatially resolving individual signals produced by the device, as described in U.S. Pub. No. 2009-0010804, incorporated by reference in its entirety.

In this regard, an imaging device of the present invention can be any known in the art that is compatible with the various designs and configurations of the instant device. For example, the camera can employ any common solid state image sensor including a charged coupled device (CCD), charge injection device (CID), photo diode array (PDA), or complementary metal oxide semiconductor (CMOS).

The device may optionally incorporate markers, such as lines, dots or visible substances in ducts and/or chambers to enable registration and/or analysis. Registration marks may be included on the device to allow for automatic correction of optical aberrations, or adjustment of the image for the angle and orientation at which the picture was taken. For detecting fluorescent output, chirped excitation/readout can be used. For example, the device can be exposed to blue excitation light for, for example, nanoseconds, then turned off, and fluorescence may be detected, for example, a nanosecond later. Then, ten nanoseconds later, for example, another image is collected (without an initial excitation flash) to produce a background intensity image for subtraction. In this manner, fluorescence can be analyzed even in daylight. For safety, the detector could be designed to recognize the device automatically, for example if the device includes a recognizable pattern, such that the detector would only produce the excitation light when pointed at the device (see Sia et al., Angewandte Chemie Int. Ed. 43:498-502 (2004), incorporated by reference herein, which describes additional means for detecting signals in multifluidic devices, including using pulse modulation to reduce noise). Detection can also be improved by using the polarization of excited/emitted light, as is known to those skilled in the art.

The devices and systems of the invention can include any number of modifications or benefits, including sterile before use (e.g., the device can be assembled in a sterile environment and then packed in a sealed container until sample collection); resistant to interference and contaminants until final analysis (e.g., a lubricant can be provided between the layers and can act as a barrier between the sample and the external world to prevents contamination and avoids leaks of potentially dangerous analytes present in the stored samples); power free usage, where some of these devices may require no power for fluid handling (autonomous biospecimen collection) or drying (no need for heating or ventilation); adaptability for easy digitized storage and rehydration (e.g., the device allows for precise manipulation of many volumes in parallel, where the sample can be split or partitioned into small volumes or aliquots and preserved in a digitized format, and such samples can be selectively, fully, or partially recovery for on-chip or off-chip analysis); ease of manufacturability (e.g., amenable to mass production using inexpensive materials and fabrication techniques); modularity and reconfigurability (e.g., some of these devices allow for the development of separate modules, which can be combined to produce a complete device, and each module can thus be developed separately and then integrated in the platform); ease of use (e.g., samples can be collected by users with minimal training and without any external equipment, where necessary steps from biospecimen collection to sample preservation can be either autonomous or require minimal action from the user (e.g. slipping the plates or pushing a button); adaptability for various sample sizes (e.g., some of these devices allow for easy manipulation of volumes in a wide range (1 nL-1 mL), which includes the typical volume of biospecimen collection in LRS (e.g. the amount of blood obtained from a finger prick); compatibility with commercial dry preservation matrices or desiccants (e.g., multi-target or multi-analyte stabilization can be achieved (including for DNA, RNA, and/or proteins), for instance by using different matrices in different parts of the storage device); upgradability with different matrices or desiccants (e.g., new matrices, desiccants, or drying agents can be easily incorporated in the platform, accommodating integration of new developments in matrix formulation); rapid drying (e.g., drying in less than 10 minutes, which arises from working at small dimensions and can be a critical issue in preserving samples sensitive to degradation); and adaptability for sample re-collection and downstream analysis (e.g., rehydration can be easily achieved on chip in order to recover the preserved sample).

EXAMPLES

Example 1: Device for Biospecimen Preservation

Figure 6:
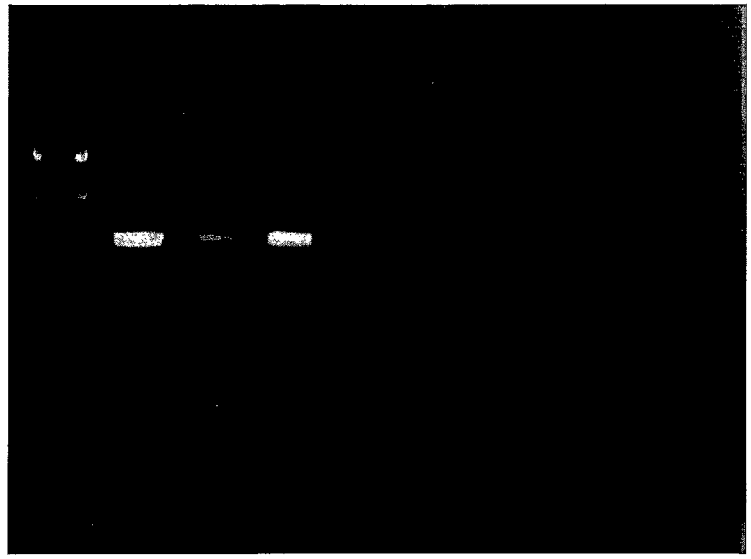
FIG. 6 provides a gel electrophoresis experiment. Provided from left to right include Ladder (lane 1), Control (RNA in tube, stored at −80° C., a typical storage condition, for lane 2), RNA recovered from a SlipChip device (lane 3), and RNA recovered from another SlipChip device (lane 4).

In FIG. 6, we show a preliminary result of an RNA sample mixed with a stabilization matrix RNAstable® produced by Biomatrica, Inc. (San Diego, Calif.) in a bridge device. The RNA sample was injected into two SlipChip devices, the layers of the SlipChips were slipped, and then the samples were recovered without substantial loss. As a control, an RNA sample was stored at −80° C. for one night. Experiments were conducted in two devices, where each was injected with the RNA sample and then dried. After drying, the SlipChip devices were stored at 65° C. for one night. Samples were rehydrated by injecting deionized water and recollected from the device.

As shown in FIG. 6, the electrophoresis gel shows that RNA was not degraded during these experiments. Due to leakage, the quantity of sample loaded in lane 3 was lower than the quantity loaded into the other lanes. No degradation was observed in any of the samples, as indicated by a single sharp band in lanes 3 and 4. As a comparison, a sample stored in a liquid state at the same temperature (65° C.) showed visible degradation after one night.

Example 2: Exemplary Device for Nucleic Acid Extraction

We directly connected a modified filter from QiaAMP MinElute (Qiagen) to a simplified version of SlipChip for nucleic acid extraction. An array of solutions, containing (in order) 675 µL lysed sample, 500 µL wash buffer AW1*, 500 µL wash buffer AW2*, and 500 µL 100% ethanol was then pushed through the filter by pressurization and through waste outlet of the SlipChip with layers arranged in an initial loading position (FIG. 16). The total time elapsed during this step was less than 3 minutes. The chip was then slipped to a second position for filter drying, which took about 2 minutes, and to a third position for elution, which took less than 1 minute. The sample was then collected from a reservoir. In sum, the total time to perform a nucleic acid extraction on a SlipChip can be as low as 6 minutes. The air drying step can be eliminated if extraction protocol does not require drying. Such protocol includes, but is not limited to Life Technologies' ChargeSwitch®.

Example 3: Second Generation Device for Nucleic Acid Extraction

The nucleic acid purification SlipChip (NA-SlipChip) contained a modified ChargeSwitch® membrane, which can bind nucleic acids at a low pH and release nucleic acids at a high pH. Sample solution, washing buffer, and elution buffers were pushed sequentially from the chambers on the top layer through the membrane into the receiving wells in the bottom layer. This is achieved by pressurizing the top layer and rotating the bottom grip disc, which is internally connected with the membrane layer. We tested the ChargeSwitch® membrane because it works with a variety of sample types, and it does not require ethanol or other organic solvents, which may compromise downstream applications such as PCR.

The second generation device (FIG. 19) was capable of performing the nucleic acid purification protocol with the ChargeSwitch® membrane. Further modification can include integration of the second-generation device with pressurization, heating, on-chip lysis, or molecular recognition modules.

Example 4: Third Generation Device for Nucleic Acid Extraction

We have designed a third generation device (FIG. 20) with a cap that can be used to apply positive or negative pressure to drive solution through the matrix. In some cases, by using the cap to decrease the enclosed volume in pressurization chamber, positive pressure was applied to the whole system. In some other cases, by using the cap to increase the enclosed volume in pressurization chamber, negative pressure was applied to the whole system.

Example 5: Large Volume Device

The SlipChip can also be applied to handle large volume of sample and concentrate analytes into small volume at a higher concentration for downstream analysis. For example, a SlipChip device that can handle 1 mL total sample volume and 200 µL of washing and elution buffers has been designed and fabricated in plastic by 3D printing (FIG. 21).

Example 6: Quantitative PCR

We have validated nucleic acid analysis in a SlipChip (NA-SlipChip) by achieving sample preparation from human plasma spiked with HIV RNA at ~70% efficiency. The efficiency of sample preparation was quantified by using real-time qPCR and digital RT-LAMP. HIV RNA was purified by using a Qiagen miniprep kit from AcroMetrix® HIV-1 Panel (5×10⁶ copies/mL). The sample solution contained 32 µL of viral lysis buffer, 2 µL of RNAse Inhibitor (New England BioLabs), 1 µL of carrier RNA (Qiagen), 5 µL of human plasma (George King Bio-Medical, Inc.), 5 µL of HIV RNA, and 10 µL of binding buffer (Life Technologies). Two washing buffers of 100 µL each and three elution buffers of 50 µL each were preloaded in the device. Viral lysis buffer, binding buffer, and washing buffer were purchased from Life Technologies as ChargeSwitch® EasyPlex™ Viral RNA/DNA Kit. Filter was modified from ChargeSwitch®-Pro Plasmid Miniprep Kit. Elution buffer was obtained from ChargeSwitch® Total RNA Cell Kit. The entire protocol took approximately 10 minutes.

Figure 23A:
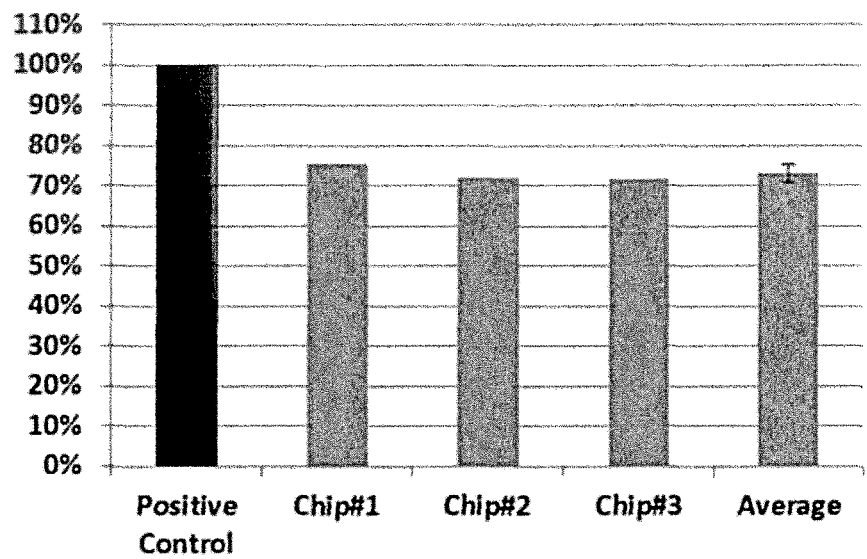
FIGS. 23A-23B provide real-time qPCR for quantification of recovery efficiency of sample preparation on a second generation device from human plasma spiked with HIV RNA. HIV RNA sample preparation from human plasma spiked with HIV RNA (~70% efficiency, FIG. 23A) was achieved on a rotational SlipChip (as shown in FIG. 19). The efficiency of sample preparation was quantified by using real-time qPCR and digital RT-LAMP.
Figure 23B:
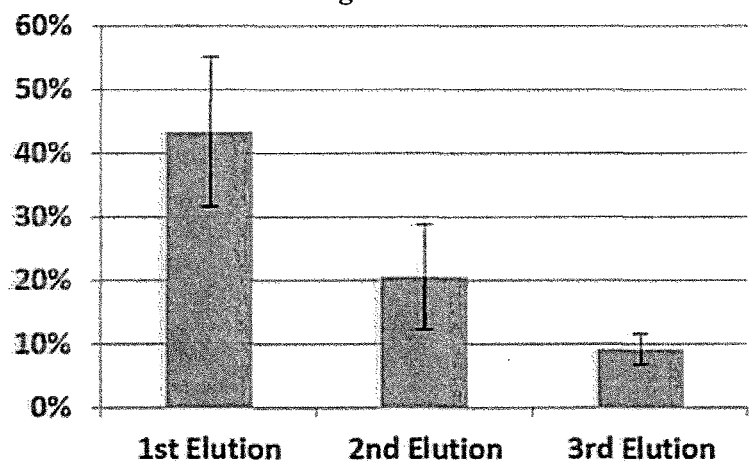

In qPCR experiments, three elutions (50 µL each) were performed and quantified by using an Illumina real-time qPCR instrument. Three sample preparation experiments were performed on the NA-SlipChip, and more than 70% recovery efficiency was achieved by combining RNA in three eluents (FIGS. 23A-23B). The recovery efficiency for the first eluent was 43±12%, the recovery efficiency for the second eluent was 20±8%, and the efficiency for the third eluent was 9±3%. Further optimization, such as elution volume, pH of elution buffer, temperature, and other buffer component, can potentially increase the recovery efficiency in the first eluent.

Example 7: Digital RT-LAMP

Figure 24:
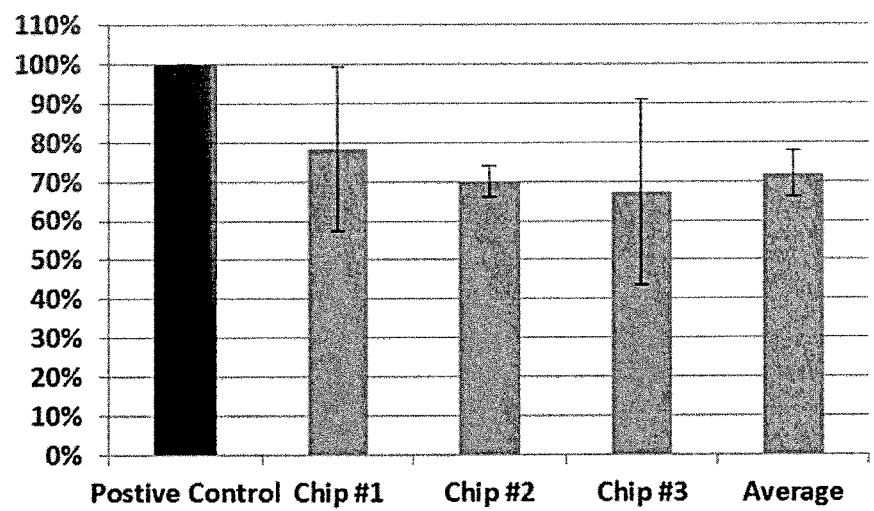
FIG. 24 provides digital RT-LAMP data for HIV RNA purified from human plasma spiked with HIV RNA. Error bars represent the standard deviation of digital RT-LAMP for each on chip sample preparation.

We also validated the compatibility of HIV RNA prepared by NA-SlipChip (as shown in FIG. 19) with downstream digital RT-LAMP (FIG. 24). The digital RT-LAMP protocol was described in detail in Sun et al., Anal. Chem. 85: 1540-1546 (2013). Briefly, digital RT-LAMP experiments were performed on glass devices with product recovered from NA-SlipChip. Material recovered from the first and second elutions was combined as template for digital RT-LAMP. At least two digital RT-LAMP experiments were performed to obtain the HIV RNA concentration. Three sample preparation experiments were performed on NA-SlipChip with human plasma spiked with HIV RNA, and the average recovery rate was above 70% (FIG. 24).

Example 8: Sample Loading and Pressure Capping Systems

Figure 39:
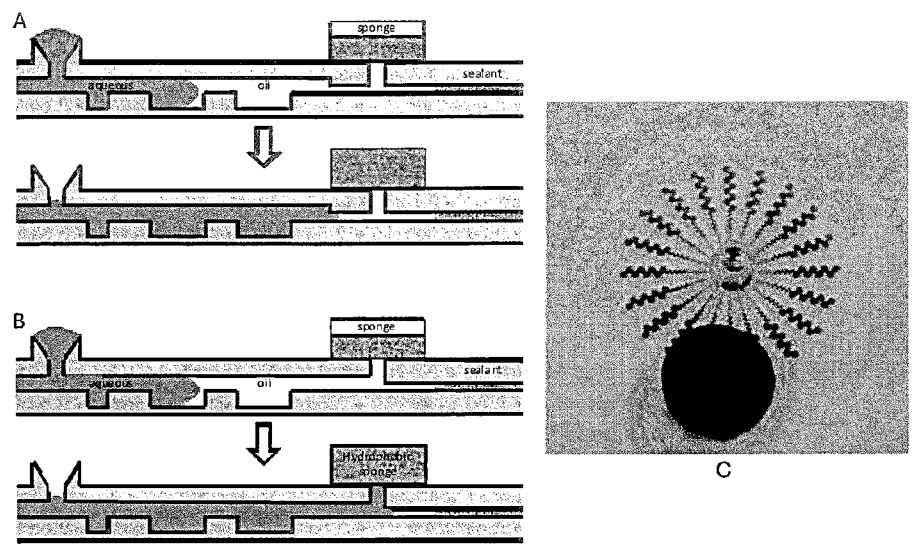
FIGS. 39A-39C provide dead-end filling of a SlipChip device by negative pressure created by a sponge. A: Dead-end filling can be promoted by using a lubricant (e.g., an oil plug), where filling of an aqueous solution in the device was terminated by the sealing pressure. B: Dead-end filling can be promoted by using a of hydrophobic sponge, where filling of an aqueous solution in the device is terminated by the hydrophobic sponge itself. C: An image of a SlipChip device loaded by using an apparatus embedded with porous material.

A housing system was designed with the following parameters, which are show in FIG. 33A: sample volume ($V_s$)=20 µL, volume of the inlet ($V_1$)=500 µL, volume inside cap head ($V_c$)=50 µL, absolute pressure generated by closing cap=1000 mbar×(500−20+50)/(500−20)=1104 mBar (=104 mbar gauge pressure), absolute pressure after 20 µL of sample has flowed out of the well=1104 mbar×(500−20+50)/(500+50)=1064 mBar (=64 mbar gauge pressure), and 1104 mBar×(500−20)/500=1060 mBar (=60 mbar gauge pressure). This method was implemented by a 6 year old child (FIG. 33B). To indicate whether the cap is fully pressed, an audible click may be provided by it or a visual indicator such as shape distortion, or tactile feedback, or any combination can be used. Other systems were also used to load and fill a device, including a buckle pump (FIG. 34), a pumping cup (FIG. 36), vacuum filling (FIG. 38), and use of a porous material (FIG. 39).

Example 9: Guiding System to Control Relative Movement

Figure 41:
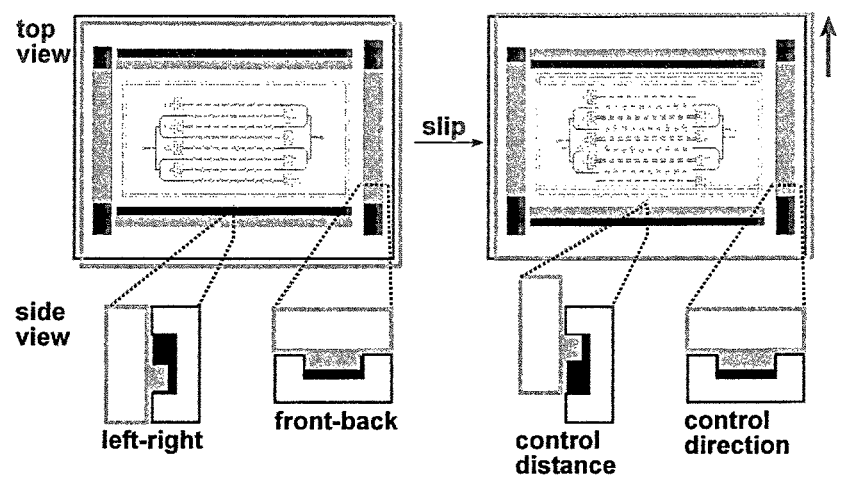
FIG. 41 provides an exemplary scheme showing two sets of internal post-groove structures in a SlipChip device to guide relative movement (e.g., slipping). One set of structures is used to control the slipping distance (side view from left to right), and another set is used to control slipping direction (side view from front to back).

Relative movement can be controlled in any useful manner. In one device, slipping was made unidirectional and autonomous by using two sets of post-groove structures to control the direction of slipping as well as the extent of slipping from a defined starting position (FIG. 41). The structures were fabricated by multi-layer wet etching technique. The first set of post and groove were fabricated at and parallel to the edge of the width to define the direction of slipping, to be always along the width. The post (~20 µm in height) was rectangle in shape and located within the groove of the sample shape (~60 µm in depth). The groove was slightly wider to prevent jams and much longer to accommodating slipping distance. The post was fabricated shorter than the depth of the groove to guarantee the tight contact between the two plates of the device. The second set of rectangular post and groove was fabricated at and parallel to the edge of the length, which controlled the slipping distance. The groove was longer than the post to prevent jams. More importantly, the post was narrower than the groove and the difference in the slipping distance. When the post is flush with one edge of the groove along the length, the chip is in a loading mode when all fluidic paths are connected respectively. One layer of the chip can then only be moved in one direction and will stop moving when the post is flush with the other edge of the groove when the chip is in reaction mode (i.e., the fluidic paths were disconnected and wells from opposite plates overlapped pair wise). Evaporation of lubricant was prevented by grease sealing. We applied silicone vacuum grease around the edges of the chip, and the chips survived a flight trip between Chicago and Los Angeles and one week storage. Successful experiments were performed on both chips.

Example 10: Integration with a Thermal Cycler

Figure 42:
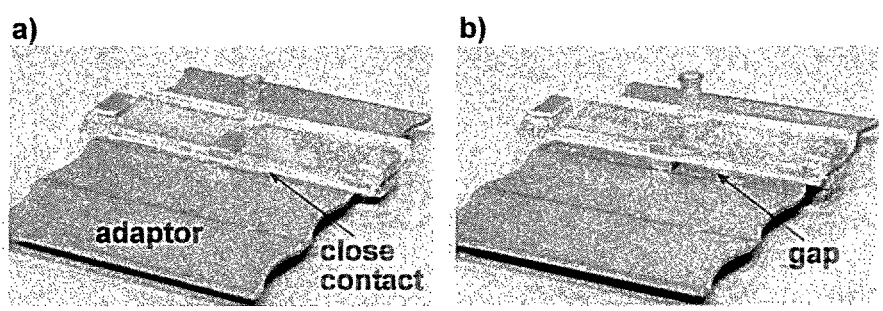
FIGS. 42A-42B show removal of middle magnet to create close contact for efficient heat transfer during thermal cycling. A: A digital PCR SlipChip was designed to contact a thermal adaptor without a gap. B: A magnet can be used to create a gap between the device and the adaptor but can prevent efficient heat transfer.

Two sets of magnets can be used on the edge of the device. For integrating the device with a thermal cycler, a third set of magnets can be used in the middle of the device. This third set prevented leaking but also prevented contact of the bottom layer of the device with the adaptor for thermal cycling (FIG. 42A). After loading and slipping, we removed one of the middle magnets to allow for contact between the device and the thermal cycler (FIG. 42B). Such contact with the adaptor would allow for more efficient heat transfer, and two sets of magnets were sufficient to clamping the layers during thermal cycling.

Further, we have developed a SlipChip for digital PCR. Plastics are not ideal for bottom plates due to their low thermal conductivity. Using a thin film, solving the heat transfer problem introduced another problem of water loss due to permeation through some polymers (such as PC), especially at elevated temperature during thermal cycling. A glass bottom layer was used to maximize heat transport, which can optionally be replaced with a metal layer or coated with a metal for effective heat transport or be replaced with a paramagnetic material (such as iron) to directly attach the top layer with embedded magnets. For the top layer, plastics can still be used by incorporating the loading feature and arrangement of magnets developed here. Such a plastic layer also provides imaging access.

Example 11: Injection Molded Devices

Figure 43:
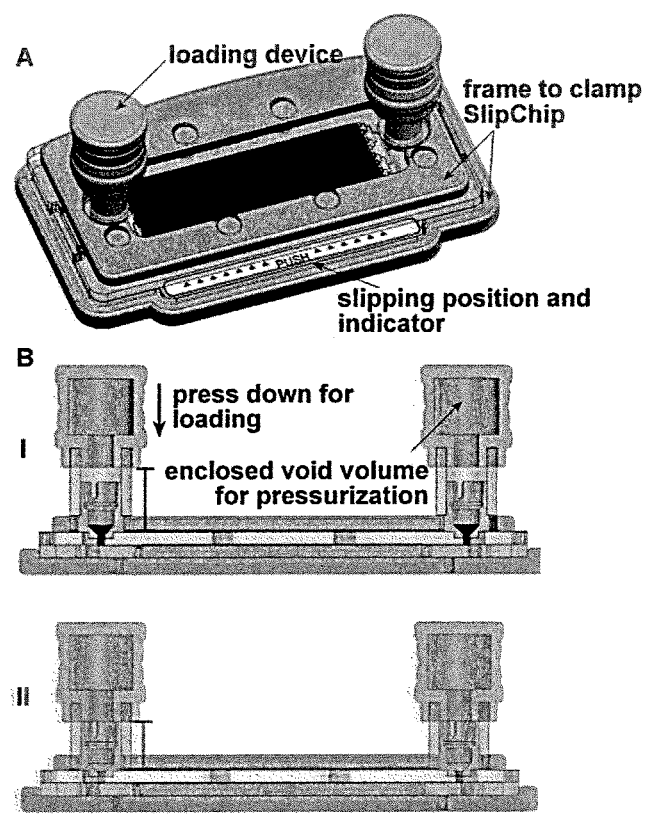
FIGS. 43A-43B provide exemplary schemes for a SlipChip device. A: A cross-sectional view of the device demonstrates loading for a device. B: Side view of the device provide a capping system to generate pressure for dead-end filling of a device.

Plastic devices were fabricated using injection molding of polycarbonate (PC). Each part could be made within a minute of processing time. The manufactured part was then surface modified by using silanization with a plasma enhanced chemical vapor deposition process (PECVD), rendering the PC surface hydrophobic surface. The plastic chip was then assembled and clamped by a pair of frames (FIG. 43A).

The loading component for the SlipChip device included transferring a sample to the inlet, such as by using any sample collection device (e.g., a collector), such as the SARSTEDT device and MICROSAFE blood collection and dispensing tubes (Safe-Tee, Inc.). A cap with expanded void volume served for both closure of sample or reagents for storage and pressurization for dead-end filling of the chip, as described herein. The bulk part of a cap was fabricated by 3-D printing and connected to PVC tubing (¼ inch inner diameter and ⅜ inch outer diameter) to provide a combined volume of 2 mL. The cap enclosed the inlet reservoir, flush with the top edge of bottom part of the reservoir that has an outer diameter of 7.2 mm. The reservoir was fabricated by machining polycarbonate and it was attached to the SlipChip devices by glue. The height of the bottom layer was 1 mm. Filling the chip was accomplished by pressing down the cap, which created a positive pressure of about 4,400 Pa (FIG. 43B).

Figure 44:
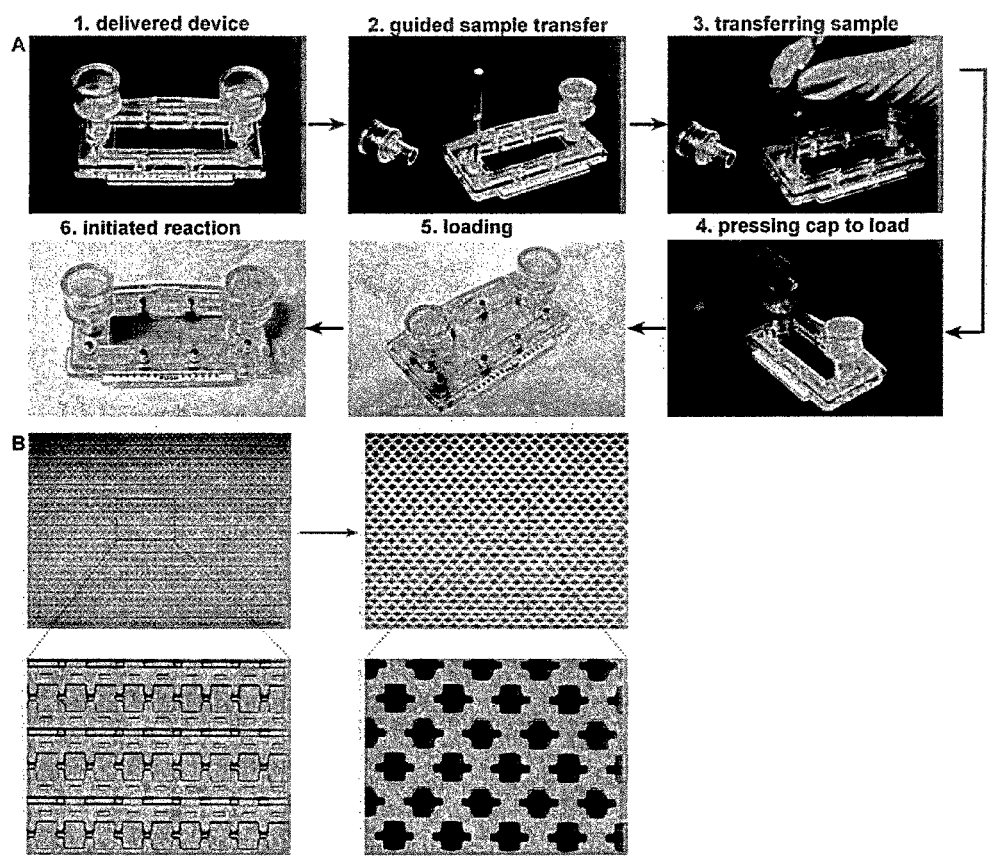
FIGS. 44A-44B provide photographs showing user-friendly operation of a SlipChip device in a step-by-step demonstration (A) to perform 1,600 nanoliter-scale experiments simultaneously after relative movement of the layers in the device (B).

A color change reaction was carried out in the plastic chips (FIG. 44). A 10 µL yellow dyed solution, containing The lid provided $V_{TOT}$=2 mL, and a PDMS ring provided $V_{RING}$=0.15 mL, so the expected pressure was ~0.075 atm (76 mBar). Using this approach, we were able to load SlipChip devices using different fluids, as reported in Table 1. Fluids included a solution containing 85% glycerol (having a viscosity on the order of ~110 mPa s, see Segur et al., Indus. Eng. Chem. 43:2117-2120 (1951)) and a solution of 0.4 mM of bovine serum albumin (BSA), having a surface energy of ~7 mN/m, see Guzman, et al., Proceedings of the 2nd Electron. Conf. Pham. Sci., 1-31 May 2012; Sciforum Electronic Conferences Series, 2012). The applied pressure decreased upon loading of the sample in the device, as did the flow rate. Total loading times for a volume of 50 µL were below two minutes for all liquids, and down to 4-5 seconds for DI water, corresponding to an average flow rate of 10-12.5 µL/s.

TABLE 1

Summary of loading speed for different fluids

| Aqueous Phase | Aqueous Viscosity (mPa s) | Continuous phase | Continuous Phase Viscosity (mPa s) | Surface Tension (mN/m) | Pressure (mBar) | Loading volume (µL) | Total time | Average flow rate (µL/s) |
|---|---|---|---|---|---|---|---|---|
| Water | 1 | Air | ~0 | ~50 | 76 | 50 | 4 s | 12.5 |
| Water | 1 | Air | ~0 | ~50 | 76 | 50 | 5 s | 10 |
| 85% Glycerol 15% Water | 110 | Air | ~0 | ~50 | 76 | 50 | 35 s | 1.4 |
| 85% Glycerol 15% Water | 110 | Air | ~0 | ~50 | 76 | 50 | 2 min | 0.4 |
| Water + 0.4 mM BSA | 1 | Air | ~0 | ~7 | 76 | 50 | 18 s | 2.8 |

0.3 M KSCN, mimicking a reagent, was preloaded in the inlet reservoir and capped for storage. A green dyed solution, containing 0.1 M Fe(NO$_3$)$_3$, mimicking a sample, was first collected in a MICROSAFE tube. A user then transferred the sample to the inlet (FIG. 44A, step 3). A guiding feature on the inlet allowed better aiming and prevented spilling (FIG. 44A, step 2). Once the sample was transferred into the inlet, the cap was reinstalled. The cap could only be inserted to a point where the vent was just covered; as a result, no pressurization was initiated and it could not be further inserted without a substantially stronger force due to the presence of interference (larger diameter). Filling was achieved by pushing both caps further down until they touched the top surface of the SlipChip (FIG. 43B and FIG. 44A, step 4). Both solutions were loaded automatically (FIG. 44A, step 5). Once the filling was done, the user slipped the chip by squeezing the plates at the indicated position. Then, 1,600 color change reactions happened simultaneously (FIG. 44A, step 6, and FIG. 44B).

Example 12: Loading of the Sample Preservation Module

Figure 49:
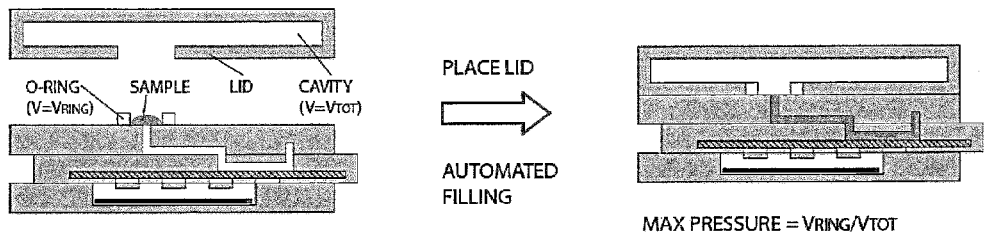
FIG. 49 provides an exemplary scheme of a device for sample preparation. Left: The device includes a flexible o-ring ($V=V_{RING}$) and liquid sample placed on the inlet hole. The lid has a cavity with empty volume $V_{TOT}$. Right: Automated filling can be achieved by placing the lid on the device, and creating a tight seal with the flexible o-ring. The maximum pressure generated depends on the cavity and o-ring geometry. In particular embodiments, the device shown in this figure is loaded with dead-end filling and can be used for dry sample preservation.

We developed and validated a power-free pumping method for a sample storage module. The only operations required to fill the device were to place the liquid sample in the inlet and then place the lid on the device. The lid is designed so that it has an empty cavity and can only be placed in one position on the device. At this position, a tight seal is created using a flexible o-ring, as shown in FIG. 49.

Sealing ensured that a controlled overpressure was created in the lid, and this overpressure was the driving force for loading the device. Without wishing to be limited by theory, the maximum applied pressure depends on the cavity and the o-ring volumes ($V_{TOT}$ and $V_{RING}$, respectively), according to this relation:

$$V_{MAX} = V_{RING}/V_{TOT} \quad \text{(Eq. 1)}$$

Example 13: Volume Quantification in a Sample Preservation Module

We have demonstrated automated loading and precise volume quantification in a dry sample storage module. We designed and produced a prototype module for sample preservation in the dry state. This storage module is intended for untrained users, as it requires only three simple steps to be operated: (1) placing the sample, (2) placing the lid (thus activating automated filling), and (3) slipping (thus activating automated drying). Key features of this approach include robustness of filling and the precise quantification of the sample volume stored in the device.

Figure 50:
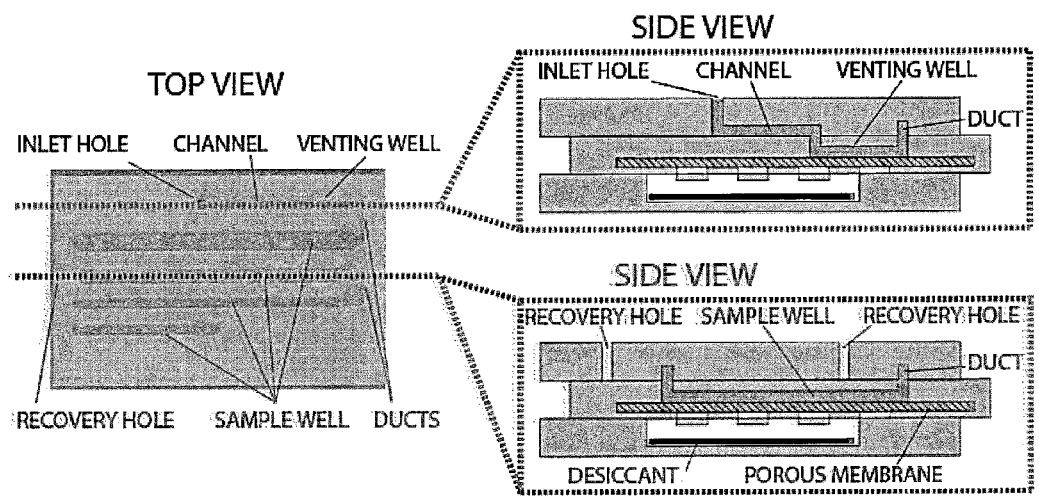
FIG. 50 provides a non-limiting exemplary scheme for volume quantification in a device of the invention. Left: Provided is a top view photograph of a dry sample preservation module loaded with food dye, which shows the shape and location of the different parts of the device. The lid and o-ring were omitted for clarity. Right: Provided are side view schemes for the same module in loading position. The top scheme (along the first horizontal dashed line) provides the inlet hole, inlet channel, venting well, and a duct. The bottom scheme (along the second horizontal dashed line) shows one sample well, ducts, and recovery holes. In both schemes, the o-ring and lid were omitted for clarity.

Filling was achieved by using the overpressure created when the lid is placed on the device, as described in FIG. 50. We designed the device to be loaded in dead-end filling mode, including a total of five wells: four wells were intended for sample storage (volumes are 20 µL, 15 µL, 10 µL, and 5 µL, with a total volume 50 µL), while an extra venting well was used to control the loading. A top view photograph of the storage module is shown in FIG. 50, which includes two side view schemes.

Figure 51:
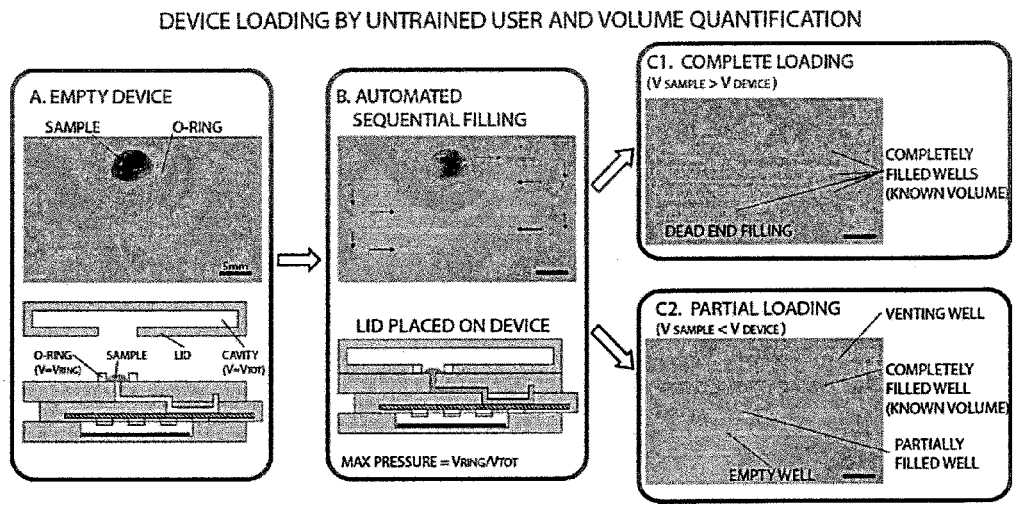
FIGS. 51A-51C provide a non-limiting exemplary scheme for automated loading for dry sample preservation module. A: An empty device with sample (water and food dye solution) was placed at the inlet. B: Sequential filling is shown. After the lid is placed on the device, sequential filling of the device happens automatically. The wells are filled one by one along the path shown by the black arrows. C1: Complete loading is shown. If the sample volume is higher than the total device volume, then loading stops automatically due to dead-end filling. C2: Partial loading is shown. If the sample volume is lower than the total device volume, then loading stops automatically once air enters in the venting well. The first well is completely loaded, and its volume is known. The second well is only partially loaded, and its content can be quantified by image analysis of the fraction filled with sample.

The injected volumes were precisely controlled without requiring any action by the user. FIG. 51 shows the loading process for complete and partial filling of the storage module. The well geometry was designed so that loading is sequential, where each well was completely filled before the sample enters the next well (FIG. 51B). If the sample volume placed on the device by the user is more than 50 µL, then filling stops automatically when all the wells are full (FIG. 51C1). Alternatively, if the sample volume is smaller than the total capacity of the device, then filling stops automatically as soon as air is injected in the venting well. Any extra pressure is released through the membrane below the venting well. Sequential filling ensures that precise sample quantification is possible, simply by counting the completely filled wells (FIG. 51C2).

We evaluated the robustness of filling by using different sample volumes and injecting them in different devices. Each condition was tested with at least three devices, and devices were filled up to three times each. For all volumes above 50 µL, the devices were completely filled, and filling stopped automatically. When loading smaller volumes, filling stopped as soon as the air entered the venting well, and all devices showed the expected number of completely filled wells.

Figure 52:
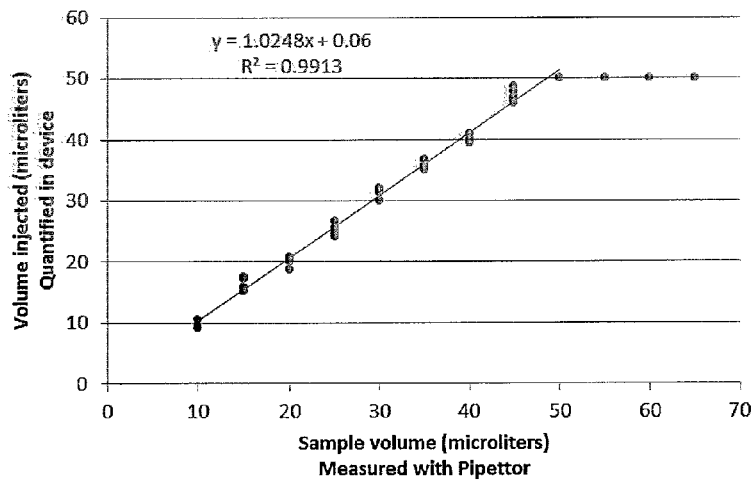
FIG. 52 provides a graph showing the volume injected in the device versus sample volume placed at the inlet. Complete filling was observed for sample volumes greater than 50 µL the device is completely filled. If the sample volume is below 50 µL, then a linear relation is observed between the sample volume and the injection volume in the device.

We tested the filling robustness even further by measuring the actual injected volume in the partially filled wells. Images of the device were acquired after loading with a colored solution (water and food dye) (see, e.g., FIG. 51). We then measured the fraction of the wells containing the solution and used the device dimensions to calculate the injected volume. FIG. 52 shows a graph of the sample volume (measured in the device) versus the expected sample volume (measured with a pipettor). These results show a precise correlation between the two volumes.

Example 14: Storage of RNA in Membrane Devices

Figure 13:
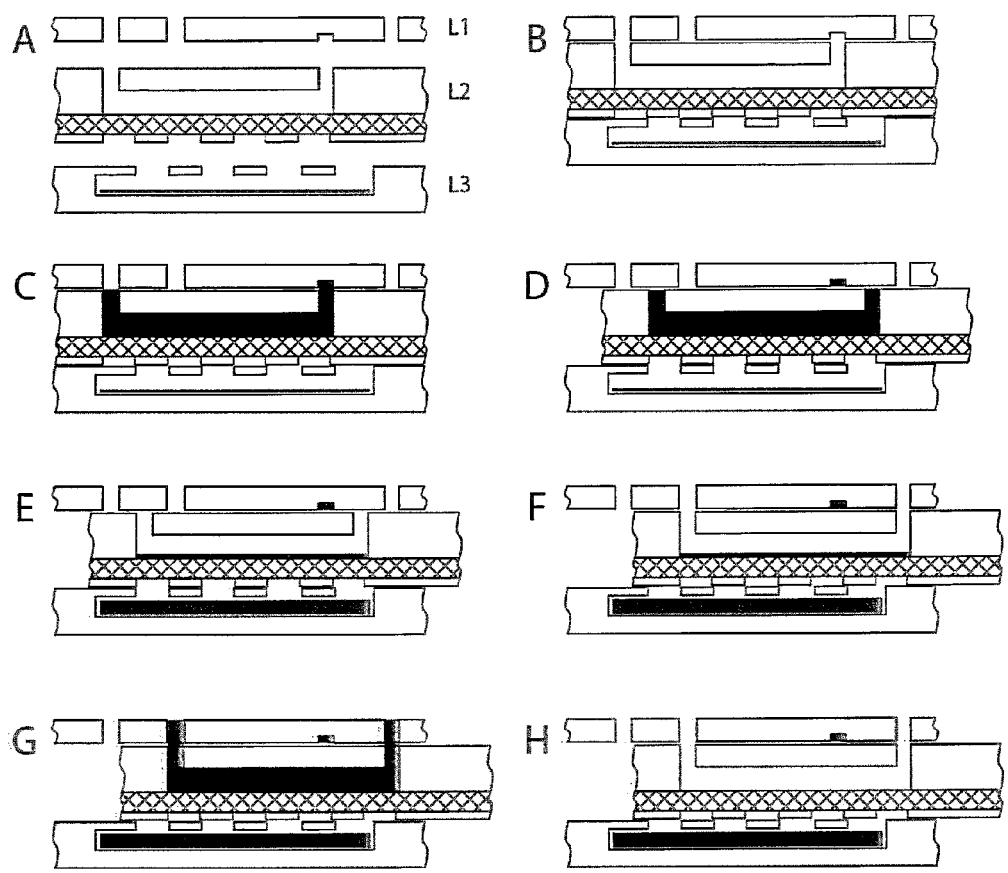
FIGS. 13A-13H provide an exemplary scheme for a three layer device for drying and recovery. A: The device includes three layers: L1 includes via holes for loading/recovery and chambers for sequential loading (not shown) as described in FIG. 11A-11H or 12A-12F; L2 includes via holes, chambers, and a porous membrane (cross-hatched); and L3 includes a desiccant. B: The assembled devices includes layers L1-L3 and, as shown, are in the loading position. C: A sample can be loaded into the chamber of layer L2. D: Relative movement of layer L2 (e.g., by slipping) provides the device in a drying position. E: Drying (e.g., after 30 minutes) results in a dried, preserved sample and a hydrated desiccant. F: Relative movement of layer L2 (e.g., by slipping) provides the device in a recovery position. G: injection of a solvent (e.g., water or buffer) provides a rehydrated sample. H: Using any useful method or apparatus (e.g., a pipettor tip), the sample is recollected from the device. The device can be loaded with dead-end filling, as described herein.

We tested the storage of RNA in devices including a commercially available stabilization matrix. A device, as shown in FIG. 13, was used for storage of RNA. Devices were loaded using a standard pipettor or using the pressure generated by a lid, as described in FIG. 49. Molecular sieves were used as a drying agent in all experiments. Drying was activated by slipping the device to the "Drying position" (as in FIG. 13E). Recovery was performed by slipping the central layer of the device to the "Recovery position" (as in FIG. 13F) and by introducing deionized water in each channel using a standard pipettor. Samples were recollected with a pipettor, and the channel was washed three times to dissolve all the dried analyte. The volumes were then normalized for all aliquots and all storage conditions in order to obtain the same concentration of analyte in all aliquots for detection by electrophoresis or PCR, as described below.

In one experiment, a high concentration of RNA was stored under various conditions. In brief, RNA (80 ng/µL) was mixed with RNAstable® stabilization matrix (available from Biomatrica, Inc., San Diego, Calif.). RNAstable® is a proprietary mixture that works by forming a glass-like shell around RNA samples using principles of anhydrobiosis and vitrification. This mixture includes <10% of TRADE SECRET 068136, <5% of TRADE SECRET 073750, <5% of ethylenediaminetetraacetic acid disodium dehydrate (EDTA), and <0.1% of phenol red. Aliquots of the RNA and RNAstable® solution were stored in three different ways: 1) frozen in a microcentrifuge tube at −80° C.; 2) loaded in a membrane storage device and dried, which was then stored at 50° C.; and 3) loaded in a microcentrifuge tube, which was then stored in a liquid state at 50° C. After four days, the preserved samples were rehydrated and recollected from the device. Electrophoresis was performed using an Agilent Bioanalyzer (RNA nanokit).

Figure 54:
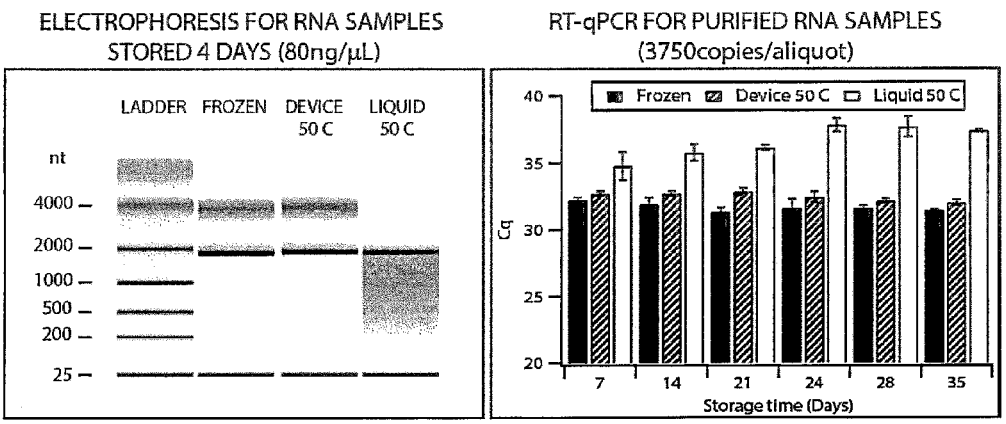
FIG. 54 provides Reverse Transcription Quantitative Polymerase Chain Reaction (RT-qPCR) in a membrane device as shown in FIG. 13. Left: Provided is an electrophoresis characterization of control RNA (80 ng/mL) that was mixed with a stabilization matrix (RNAstable®, Biomatrica) and stored for four days. Aliquots were stored either in microcentrifuge tubes in a −80° C. freezer ("Frozen"), in a membrane device in a preserved state at 50° C. ("Device 50C"), or in microcentrifuge tubes in a liquid state at 50° C. ("Liquid 50C"). Aliquots stored in the preserved state in the membrane device at 50° C. showed no difference from the aliquots stored frozen in a freezer, while the aliquots stored in the liquid state at 50° C. show visible degradation. Right: Quantitative analysis was performed using RT-qPCR. RNA was purified from inactivated HIV-1 viral particles. Aliquots containing ~3750 copies of RNA were stored either in microcentrifuge tubes in a −80° C. freezer ("Frozen"), in a membrane device in a preserved state at 50° C. ("Device 50C"), or in microcentrifuge tubes in a liquid state at 50° C. ("Liquid 50C"). RT-qPCR was performed at different time points, showing no significant variation between the samples stored frozen or in the device, even after 35 days of storage. Aliquots stored at high temperature in the liquid state show visible degradation after 7 days, and the difference in Cq progressively increased over time.

As shown in FIG. 54 (left), samples stored in the frozen state were comparable to those stored in the preserved or dried state in a membrane device at 50° C. In contrast, samples stored in the liquid state at 50° C. showed visible degradation.

In another experiment, a purified viral RNA was stored under various conditions. In brief, RNA was purified from inactivated HIV-1 viral particles in plasma (AcroMetrix® HIV-1 Panel, copies/mL, available from Life Technologies Corp., Carlsbad, Calif.). The purified RNA was mixed with RNAstable® stabilization matrix, described above. RNA was stored under various conditions. Aliquots containing ~3750 copies of RNA were stored either in microcentrifuge tubes in a −80° C. freezer ("Frozen"), in a membrane device in a dry state at 50° C. ("Device 50C"), or in microcentrifuge tubes in a liquid state at 50° C. ("Liquid 50C"). At desired time points, the preserved aliquots were rehydrated and recovered from the device. Different storage conditions were compared by quantifying the RNA using RT-qPCR and comparing the measured Cq (three aliquots for each condition). RT-qPCR was performed at different time points, showing no significant variation between the samples stored frozen or in the device, even after 35 days of storage. Results showed no significant difference between the aliquots stored in the dry state in the device and stored in the frozen state. Aliquots stored at a higher temperature of 50° C. in the liquid state showed visible degradation after 7 days, and the difference in Cq progressively increased over time.

Example 15: Volume Quantification for Sample Collection

We characterized dead-end filling of various substances (e.g., solutions and blood) in a device. First, we tested whether we can collect solutions quickly (e.g., less than 10 seconds to collect a 50 µL sample with a flow rate of 5 µL/sec). In particular, this shortened time scale could facilitate point-of-care testing, which benefit from rapid results obtained in real time. For this purpose, we assumed that flow rate was determined by the dissipation of lubricant oil through the gap due to its much higher flow resistance (as compared to other aqueous reagents or samples). Based on this assumption, flow resistance Rh was determined as follows:

$$Rh \approx \frac{12 \times \mu \times L}{w \times h^3 \times \left(1 - 0.630 \times \frac{h}{w}\right)} \quad \text{(Eq. 2)}$$

where $\mu$ is the viscosity of flowing fluid; L is the path length traveled by the fluid; w is the width of the fluid; and h is the depth of the fluid, where h<w. Consequently, the flow rate was on the scale of 1-10 nL/sec. In order to increase the flow rate, we designed a collection device to reduce flow resistance in the gap between the layers. Specifically, we decreased the length through which the lubricant dissipates and increased the width as chamber or well. As a result, the resistance in the gap was comparable to the flow resistance of an aqueous solution being loaded in the fluidic path, and both solution loading and lubricant dissipation contributed to the overall flow rate. In this manner, we increased the flow rate to hundreds of nL/sec (Table 2).

TABLE 2

Summary of collection speed of the collection SlipChip.

| Aqueous phase[a-c] | Aqueous viscosity (cp) | Lubricant phase[d-e] | Lubricant viscosity (cp) | Surface tension (mN/m) | Channel size Width (μm) | Channel size Height (μm) | Channel size Gap (μm) | Loading volume (μL) | Average flow rate (nL/sec) |
|---|---|---|---|---|---|---|---|---|---|
| iron dye | 1 | FC-3283 | 1.4 | ~50 | 1648 | 74 | 3 | 10 | 160 |
| iron dye | 1 | FC-3283 | 1.4 | ~50 | 1648 | 74 | 3 | 20 | 250 |
| iron dye | 1 | Air | ~0 | ~50 | 1648 | 74 | 3 | 20 | 292 |
| iron dye | 1 | Air | ~0 | ~50 | 1158 | 148 | ~1 | 27 | 15709 |
| iron dye | 1 | FC-40 | 3.4 | ~50 | 1648 | 74 | | 10 | 187 |
| iron dye + 20% PEG 8K | 20 | FC-3283 | 1.4 | ~50 | 1648 | 74 | 3 | 10 | 29 |
| iron dye + 20% PEG 8K | 20 | FC-3283 | 1.4 | ~50 | 1648 | 74 | 3 | 20 | 23 |
| iron dye + 0.25% SDS | 1 | FC-3283 | 1.4 | ~15 | 1648 | 74 | 3 | 20 | 197 |

[a] the iron dye was a red solution formed by combining 0.1M Fe(SCN)$_3$ and 0.3M KNO$_3$.
[b] PEG8K is poly(ethylene glycol) having an average molecular weight of 8,000.
[c] SDS is sodium dodecyl sulfate.
[d] FC-3283 includes perfluoro compounds (primarily compounds with 9 carbons) (CAS No. 86508-42-1, available from 3M, St. Paul, MN).
[e] FC-40 is includes perfluoro compounds (primarily compounds with 12 carbons) (CAS No. 86508-42-1, available from 3M, St. Paul, MN).

In this scenario, the viscosity of the aqueous sample had an effect on the flow rates, indicating the significance of flow resistance in the fluidic path. Thus, we further increased the dimension of the fluidic path. In addition, we replaced the lubricant with air to render the resistance in the gap insignificant, such that increasing the gap does not change the loading speed. As a result, we increased the flow rate to over 15 μL/sec and reduced the collection time to less than two seconds to collect a 27 μL volume. In this manner, a skilled artisan would be able to modify the methods (e.g., by choosing various lubricants of varying viscosity, by replacing a lubricant with air, and/or by designing devices having particular cross-sectional dimensions, as described herein to accommodate desired flow rates, collection times, and/or collection volumes).

Figure 55:
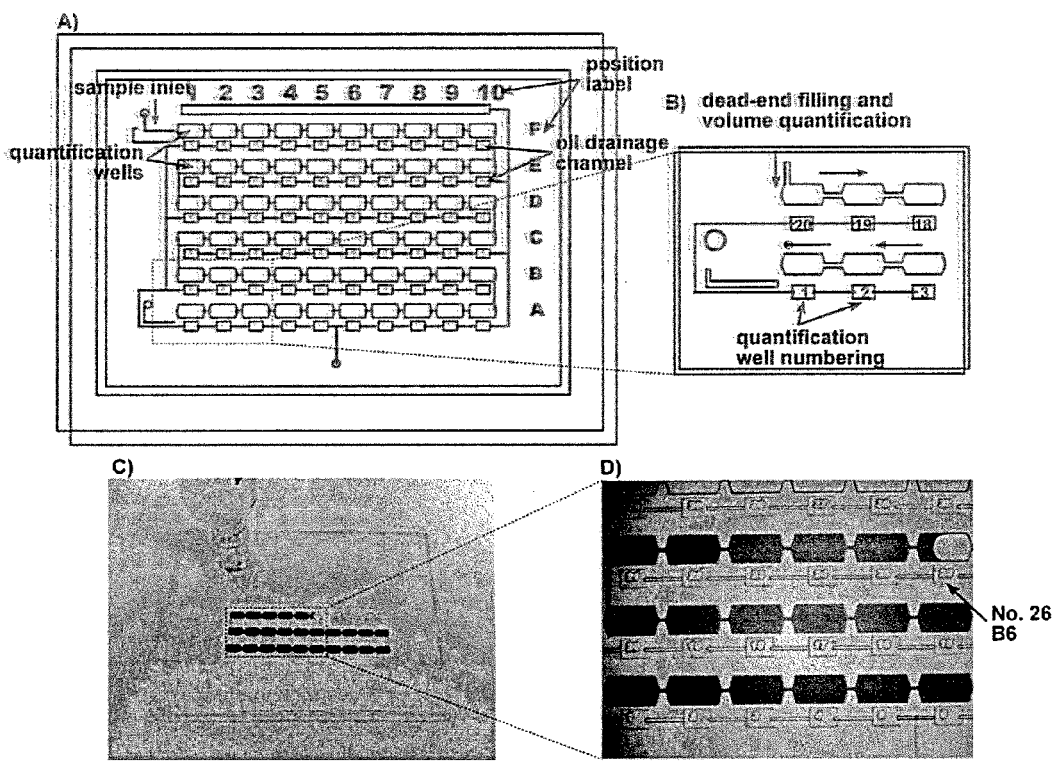
FIGS. 55A-55D provides a non-limiting SlipChip device for sample quantification. Provided is a scheme showing the layout of the chip in plan view (A) and a close-up view (B), as well as a microphotograph of the device quantifying 9.87 µL of whole blood (C) and a close-up image of the last filled well (number 26), which corresponds to a volume 9.8 µL and demonstrates a volume ratio of 99.1% (D).

Next, we characterized the accuracy of the collection device. The chip included quantification wells connected by short and narrow channels (or necks) (FIG. 55A). Each well and connecting neck has a known volume defined by their dimensions. We used the dead-end filling technique described above, so once loading was complete, the wells were always filled completely and sequentially. In this manner, quantification of the volume of a collected sample was reduced to the task of counting the number of filled wells. We labeled the wells numerically in the order of filling (FIG. 55B). Upon identifying the number of the last filled well (FIGS. 55C-55D), the volume of sample was determined by multiplying that number with the sum of the volume of one well and one neck. We determined the accuracy of the collection device by characterizing the volume ratio (i.e., the ratio of indicated volume to actual volume) and the standard deviation of each actual volume measured in duplicate or triplicate (Table 3).

Figure 56:
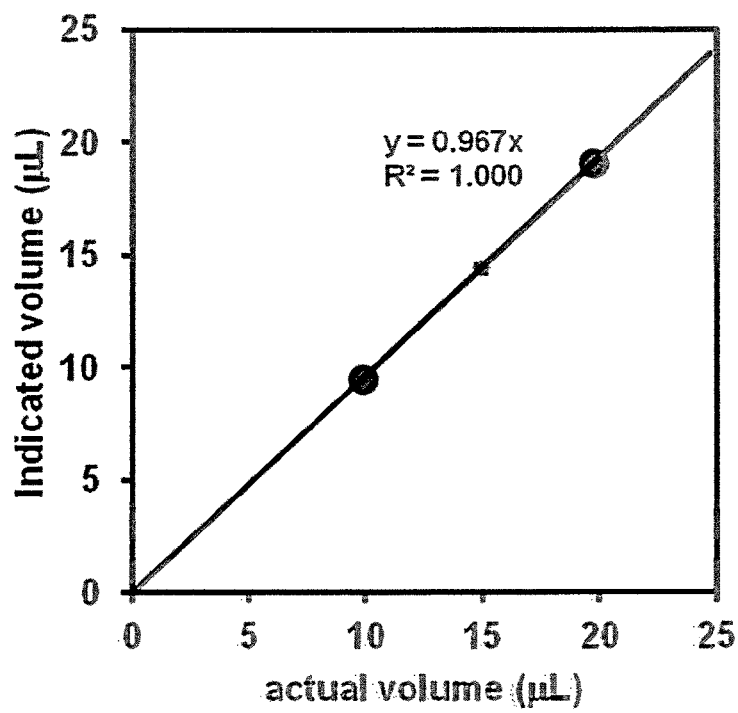
FIG. 56 is a graph showing volume quantification using an exemplary collection SlipChip. The calibration curve (diamonds) indicates a volume ratio of 96.7% and precision of better than +/−5%. The red circles indicate experiments with whole blood.

We used a red solution (0.1M Fe(SCN)$_3$+0.3 M KNO$_3$) to perform the characterization. This solution has a viscosity of 1 cp, and its surface tension is about 50 mN/m with the lubricant oils and air. We changed the viscosity of the solution by adding PEG 8000, and we changed its surface tension by adding a water soluble surfactant, SDS. The volume ratio was over 95% regardless of the viscosity or surface tension of the loaded solution, or the viscosity of the lubricant oil. Furthermore, in all cases, the volume determined by the collection device was consistent, with the volume ratios all over 95% except in one case, indicating an accuracy of over 95% (Table 3, FIG. 56). In the current design, we have 60 wells, with each well and neck having a combined volume of ~360 mL, and the quantification protocol we implemented here does not take into account how completely the last well is filled. The precision of quantification is less than 360 mL, corresponding to less than 4% of 10 μL. However, if for any application higher precision is required, the number of wells can be increased and their volumes correspondingly decreased.

Figure 57:
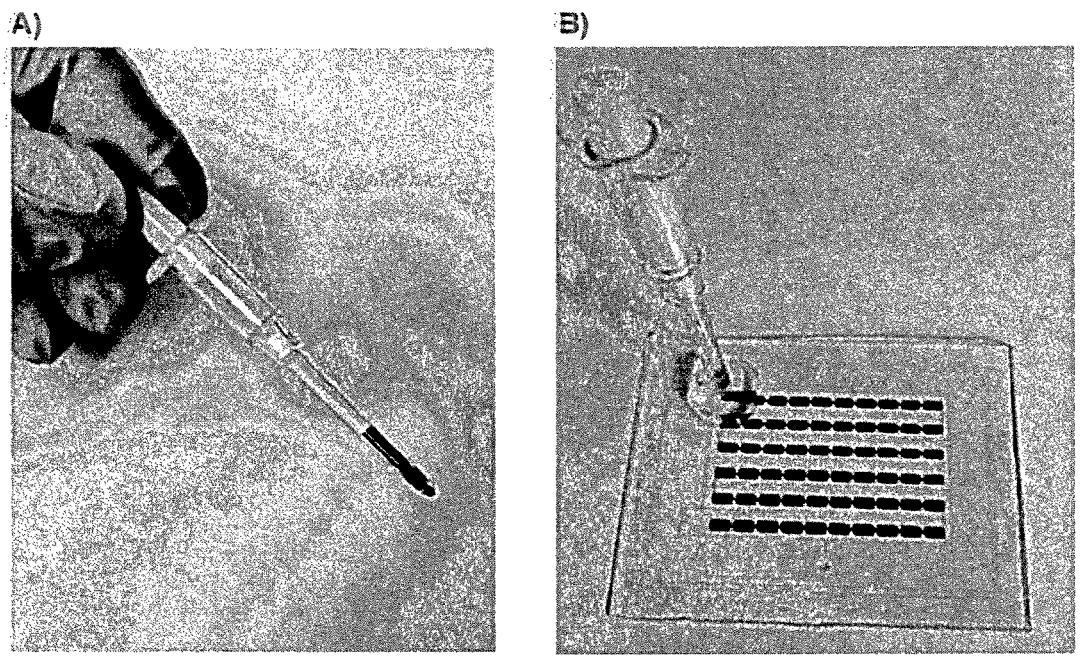
FIGS. 57A-57B provide photographs of the integrated use of quantification SlipChip with a commercially available blood collection device. A: A whole blood sample was collected using a SARSTEDT minivette. B: The minivette was interfaced to SlipChip for sample quantification, where the indicated volume was 17.3 µL.

We then quantified the collection device using a blood sample. First, we confirmed that the volume ratio was over 95% (Table 3, FIG. 56). Then, we used a commercially available blood collection device to collect blood from finger pricks (FIG. 57A). This blood sample was loaded into the SlipChip collection device for volume quantification (FIG. 57B). The volumes of the compartmentalized samples were successfully quantified.

TABLE 3

Volume quantification by using the collection SlipChip.

| Collected solution[a-c] | Aqueous Viscosity (cp) | Lubricant phase[d-e] | Lubricant viscosity (cp) | Surface tension (mN/m) | Actual volume (μL) | Indicated volume (μL) | Standard Deviation (%) | Recovery (%) |
|---|---|---|---|---|---|---|---|---|
| iron dye | 1 | FC-3283 | 1.4 | ~50 | 9.87 | 9.53 | 4.5 | 96.5 |
| iron dye | 1 | FC-3283 | 1.4 | ~50 | 14.89 | 14.42 | 1.5 | 96.8 |
| iron dye | 1 | FC-3283 | 1.4 | ~50 | 19.74 | 19.08 | 2.4 | 96.6 |
| iron dye | 1 | Air | ~0 | ~50 | 9.87 | 9.41 | 0 | 95.3 |
| iron dye | 1 | Air | ~0 | ~50 | 19.74 | 19.22 | 0 | 97.4 |
| iron dye | 1 | FC-40 | 3.4 | ~50 | 9.87 | 9.66 | 2.2 | 97.8 |

TABLE 3-continued

Volume quantification by using the collection SlipChip.

| Collected solution[a-c] | Aqueous Viscosity (cp) | Lubricant phase[d-e] | Lubricant viscosity (cp) | Surface tension (mN/m) | Actual volume (μL) | Indicated volume (μL) | Standard Deviation (%) | Recovery (%) |
|---|---|---|---|---|---|---|---|---|
| iron dye + 20% PEG 8K | 20 | FC-3283 | 1.4 | ~50 | 9.87 | 9.41 | 0 | 95.3 |
| Iron dye + 20% PEG 8K | 20 | FC-3283 | 1.4 | ~50 | 19.74 | 19.22 | 0 | 97.4 |
| iron dye + 0.25% SDS | 1 | FC-3283 | 1.4 | ~15 | 9.87 | 9.78 | 0 | 99.1 |
| iron dye + 0.25% SDS | 1 | FC-3283 | 1.4 | ~15 | 19.74 | 19.22 | 0 | 97.4 |
| whole blood | ~10 | FC-3283 | 1.4 | — | 9.87 | 9.53 | 2.3 | 96.6 |
| whole blood | ~10 | FC-3283 | 1.4 | — | 19.74 | 19.08 | 2.4 | 96.6 |

[a] the iron dye was a red solution formed by combining 0.1M Fe(SCN)$_3$ and 0.3M KNO$_3$.
[b] PEG8K is poly(ethylene glycol) having an average molecular weight of 8,000.
[c] SDS is sodium dodecyl sulfate.
[d] FC-3283 includes perfluoro compounds (primarily compounds with 9 carbons) (CAS No. 86508-42-1, available from 3M, St. Paul, MN).
[e] FC-40 is includes perfluoro compounds (primarily compounds with 12 carbons) (CAS No. 86508-42-1, available from 3M, St. Paul, MN).

Example 16: Sample Preservation Activated by Slipping, Rehydration, and Recovery We tested an exemplary SlipChip device to preserve (e.g., dry) a sample on-chip, followed by rehydration and recovery of the preserved sample (FIGS. 62A-62D and 63A-63D).

Figure 62:
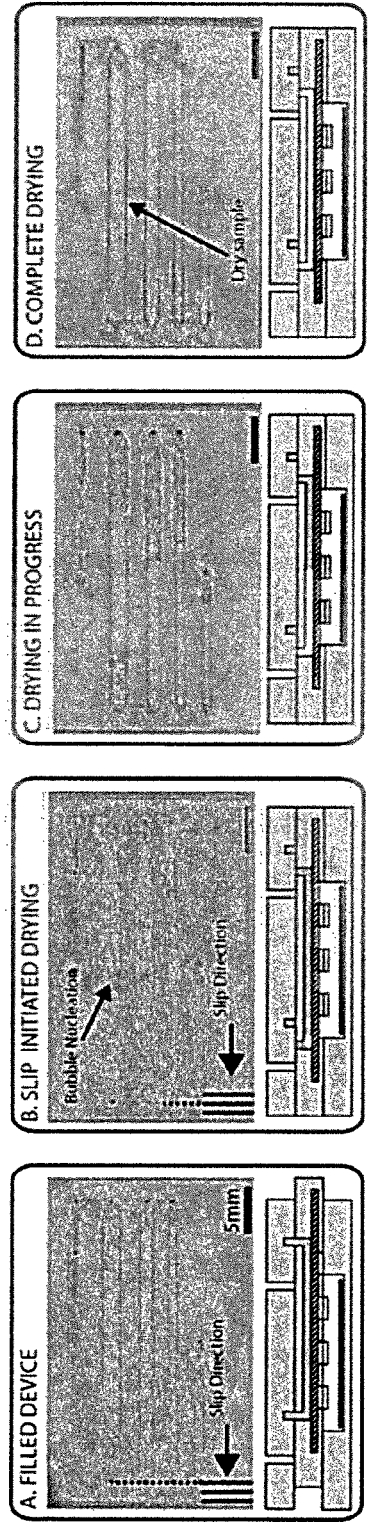
FIGS. 62A-62D provide photographs and schemes for sample drying that is activated by slipping. Provided are photographs (top) and schemes of a side view along a sample chamber (bottom). A: A device was filled with sample (in this case aqueous solution containing dye). B: Slip-initiated drying was initiated. One slip separates the aliquots and places the sample in vapor contact with the desiccant, thus activating the drying process. Drying starts with bubble nucleation. C: As drying progresses, the bubble grows while the sample gets more and more concentrated in the liquid phase. D: After complete drying, only a solid residue is present in the chambers.

A device was filled with a sample (aqueous solution with dye, FIG. 62A). The layers of the device were slipped to place the sample in vapor contact with the desiccant, thus activating the drying process (FIGS. 62B-62C). After complete drying, a solid residue was present in the wells (FIG. 62D). By controlling the drying process (e.g., the drying time) and the type of desiccant or matrix, this device and method can be modified to preserve the sample in a liquid or dried, solid state.

Figure 63:
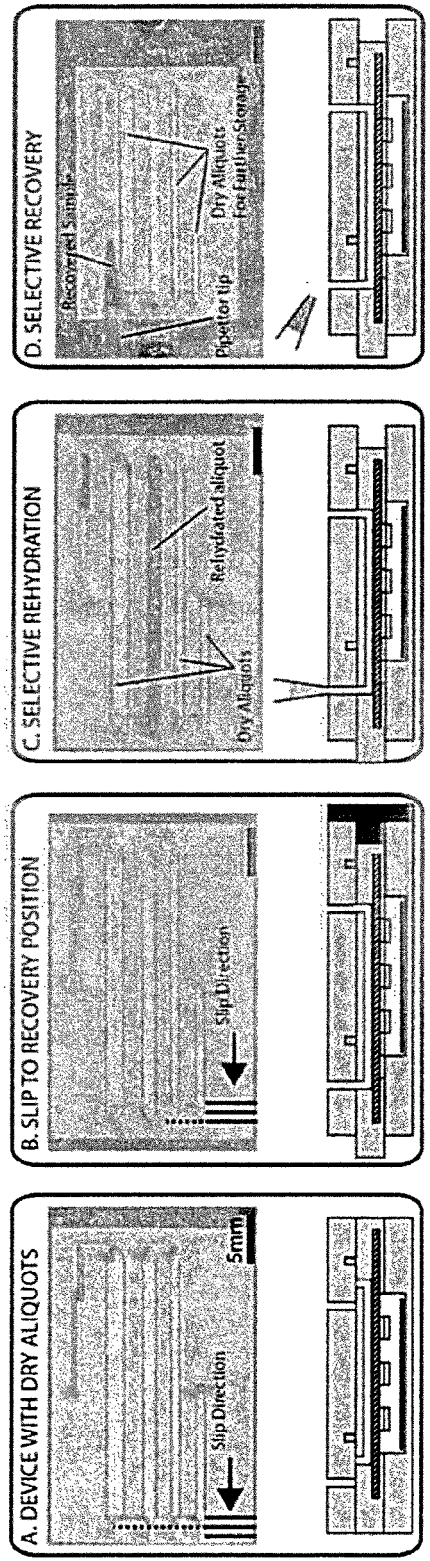
FIGS. 63A-63D provide photographs and schemes for sample rehydration and recovery. Provided are photographs (top) and schemes of a side view along a sample chamber (bottom). A: A device including a dried sample (e.g., as described in FIGS. 62A-62D) is provided. B: A slip moves the device to the recovery position. In particular embodiments, slipping can be achieved with an external tool to reduce accidental overslipping by untrained users or mishandling. C: Using selective rehydration, water or other solutions (e.g., buffers) can be injected with a pipettor in one well. A sample is rehydrated only in that chamber. D: Using selective recovery, a rehydrated sample is recovered from the device with a standard pipettor and ready to process with standard laboratory techniques.

A preserved sample within a device can be selectively rehydrated and recovered. The layers of the device were slipped to the recovery position (FIG. 63A-63B) to allow introduction of a fluid (e.g., water, a buffer, or any useful solution) into the selected well (FIG. 63C). Then, the rehydrated sample is recovered from the device with a standard pipettor (FIG. 63D) and can be used for optional further process with standard laboratory techniques.

Example 17: Sample Concentration

Figure 64:
FIGS. 64A-64C provide a description of sample concentration by evaporation. A: The device can be loaded with a sample, where the circle on the right indicates an open inlet. B: Drying can be activated by exposing the left channel ("drying region") to the desiccant. Flow can be generated by drying, which introduced the sample into the device. C: The sample is concentrated in the drying region.
Figure 64:
Figure 64:

We tested an exemplary SlipChip device to concentrate sample by evaporation on-chip. As shown in FIGS. 64A-64C, a test sample was introduced into a device. Drying was activated, which resulted in generating flow and introducing additional sample into the device. The resultant concentrated sample is provided in FIG. 64C.

On-chip drying or sample concentration may result in nucleation of an air bubble within one or more chambers. Formation of such air bubbles could be minimized by any useful strategy, including but not limited to designing one or more features that minimize nucleation in the device (e.g., by providing a region that promotes captures vapor or gas, such as a chamber having a desiccant, a matrix, or a membrane) or promote nucleation in one or more particular regions of the device. Exemplary strategies include promoting nucleation in a specific position (e.g., one extremity of a chamber) so that drying concentrates the sample towards the other extremity or providing one or more nucleation sites in a chamber (e.g., in multiple places in the chamber) so that the sample is distributed uniformly in various regions.

OTHER EMBODIMENTS

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents and patent applications are herein incorporated by reference in their entirety to the same extent as if each individual publication, patent or patent application was specifically and individually indicated to be incorporated by reference in its entirety.

What is claimed is:

1. A device for preservation or storage of a sample comprising:
   (i) a first layer comprising a plurality of first chambers configured to hold the sample;
   (ii) a second layer comprising one or more second chambers and comprising one or more desiccants in at least one of said one or more second chambers;
   (iii) an intermediate layer disposed between said first layer and said second layer, wherein said intermediate layer comprises a porous membrane; and
   wherein at least one of said plurality of first chambers configured to hold the sample, at least one of said one or more second chambers comprising one or more desiccants, and said porous membrane are configured to be connected by relative movement thereby permitting the one or more desiccants to absorb or adsorb solvent from the sample.

2. The device of claim 1, further comprising one or more reagents for said preservation of a sample.

3. The device of claim 1, wherein said device is a microfluidic device.

4. The device of claim 3, wherein at least one of said plurality of first chambers, or at least one feature of said membrane has a dimension of 1,000 μm or less.

5. The device of claim 1, wherein at least two of said plurality of first chambers and said membrane are able to be connected by relative movement.

6. The device of claim 1, wherein said intermediate layer comprises a continuous membrane.

7. The device of claim 1, wherein said first layer, said intermediate layer, or said second layer is planar or non-planar.

8. The device of claim 1, wherein said first layer, said intermediate layer, or said second layer, or a portion thereof, is differentially wetted.

9. The device of claim 1, further comprising a deformable layer between said first layer and said intermediate layer and/or between said second layer and said intermediate layer.

10. The device of claim 9, further comprising a coating on one or more of said first layer, said intermediate layer, said second layer, or said deformable layer.

11. The device of claim 10, wherein said coating comprises a fluoropolymer.

12. The device of claim 1, wherein said first layer, said second layer, and/or said intermediate layer translates longitudinally.

13. The device of claim 1, said first layer, said second layer, and/or said intermediate layer rotates axially.

14. The device of claim 1, further comprising a third layer comprising one or more third chambers, wherein said third layer is beneath said second layer, and wherein at least one of said plurality of first chambers, at least one of said one or more second chambers, at least one of said one or more third chambers, and said membrane are able to be connected by relative movement.

15. The device of claim 14, further comprising a lubricant between said first layer and said intermediate layer and/or between said second layer and said intermediate layer and/or between said second layer and said third layer.

16. The device of claim 1, wherein one or more of said plurality of first chambers or at least one of said one or more second chambers comprise a sample, a washing buffer, an elution buffer, a lysis agent, a reagent, a dye, a stabilizer, a protein, a nucleic acid, a filter, a membrane, or a marker.

17. The device of claim 1, wherein one or more of said plurality of first chambers or at least one of said one or more second chambers is a well, a microchannel, or a duct.

18. The device of claim 1, further comprising an injection port for serial and/or sequential filling of said plurality of first chambers or at least one of said one or more second chambers.

19. The device of claim 1, further comprising a receiving chamber for controlling the volume of one or more fluids in said plurality of first chambers or at least one of said one or more second chambers.

20. A method of storing and/or preserving a sample, said method comprising:
(i) providing a device of claim 1;
(ii) introducing a test sample to said device; and
(iii) moving said first layer, said intermediate layer, and/or said second layer, if present, thereby resulting in sample storage and/or preservation.

21. The method of claim 20, wherein said sample storage and/or preservation comprises one or more of the following steps: partitioning said test sample into separate aliquots, drying one or more of said aliquots, recovering one or more of said aliquots, and/or quantifying the volume of said one or more aliquots after partitioning, before drying, after drying, or after recovering.

22. The method of claim 20, wherein said sample storage and/or preservation comprises filtering, lysing, dehydrating, rehydrating, binding, washing, eluting, assaying, and/or detecting said test sample.

23. The method of claim 20, wherein said sample storage and/or preservation comprises nucleic acid extraction, nucleic acid purification, nucleic acid enrichment, concentrating of a nucleic acid, protein extraction, protein purification, protein enrichment, concentrating of a protein, cell separation, sample enrichment, nucleic acid amplification, nucleic acid detection, and/or protein detection.

24. The method of claim 20, wherein step (iii) results in sample analysis prior to said sample storage and/or preservation.

25. The method of claim 24, further comprising relaying results from said sample analysis with a cell phone.

26. The method of claim 20, wherein said test sample comprises blood, plasma, serum, sputum, urine, fecal matter, sweat, spinal fluid, amniotic fluid, interstitial fluid, tear fluid, bone marrow, a swab, a tissue sample, a buccal mouthwash sample, an aerosol, a nucleic acid, a cell, a protein, and/or an enzyme.

27. A kit comprising:
(i) a device of claim 1; and
(ii) a collector for collecting a sample for use with said device.

28. The kit of claim 27, wherein said device further comprises one or more of a sample, a washing buffer, an elution buffer, a lysis agent, a reagent, a dye, a stabilizer, a protein, a nucleic acid, a filter, a membrane, or a marker.

* * * * *

UNITED STATES PATENT AND TRADEMARK OFFICE
CERTIFICATE OF CORRECTION

PATENT NO. : 9,808,798 B2
APPLICATION NO. : 13/868009
DATED : November 7, 2017
INVENTOR(S) : Rustem F. Ismagilov Page 1 of 1

It is certified that error appears in the above-identified patent and that said Letters Patent is hereby corrected as shown below:

In the Specification

On Column 1, after the heading STATEMENT REGARDING FEDERALLY SPONSORED RESEARCH, replace the paragraph on Lines 14-19 with the following paragraph:
-- This invention was made with government support under grant numbers OD003584 and EP012946 awarded by the National Institutes of Health and contract number HR0011-11-2-0006 awarded by the Defense Advanced Research Projects Agency. The government has certain rights in the invention. --

Signed and Sealed this
First Day of January, 2019

Andrei Iancu
*Director of the United States Patent and Trademark Office*